United States Patent [19]

Schwartz et al.

[11] Patent Number: 5,925,564

[45] Date of Patent: Jul. 20, 1999

[54] EXPRESSION VECTOR SYSTEMS AND METHOD OF USE

[75] Inventors: Robert J. Schwartz; Franco J. DeMayo; Bert W. O'Malley, all of Houston, Tex.

[73] Assignee: Baylor College of Medicine, Houston, Tex.

[21] Appl. No.: 08/472,809

[22] Filed: Jun. 7, 1995

Related U.S. Application Data

[63] Continuation-in-part of application No. 08/209,846, Mar. 9, 1994, Pat. No. 5,756,264, and a continuation-in-part of application No. 07/789,919, Nov. 6, 1991, Pat. No. 5,298,422.

[51] Int. Cl.$^6$ .............................. C12N 5/16; C12N 15/63
[52] U.S. Cl. ........................................ 435/325; 435/320.1
[58] Field of Search .............................. 435/320.1, 172.3, 435/325

[56] References Cited

U.S. PATENT DOCUMENTS

| | | | |
|---|---|---|---|
| 4,783,405 | 11/1988 | Kovacevic et al. | 435/69.4 |
| 5,082,783 | 1/1992 | Ernst et al. | 435/69.1 |
| 5,093,317 | 3/1992 | Lewis et al. | 514/12 |
| 5,298,422 | 3/1994 | Schwartz et al. | 435/320.1 |

FOREIGN PATENT DOCUMENTS

| | | |
|---|---|---|
| 0174608 | 3/1986 | European Pat. Off. . |
| 0336155 | 10/1989 | European Pat. Off. . |
| 9111522 | 8/1991 | WIPO . |
| 9112329 | 8/1991 | WIPO . |

OTHER PUBLICATIONS

Gallie et al. RNA pseudoknot domain of tabacco mosaic virus can functionally substitute for a poly (A) tail in plant and amimal cells. Genes and Development vol. 4 pp. 1149–1157, 1990.

Chow et al. A combination of closely associated positive and negative cis–acting promoter elements regulates transcription of the skeletal alpha–actin gene. Mol. and Cell. Biol. vol. 10 pp. 528–538, 1990.

Jansen et al. Sequence of cDNA encoding human insulin–like growth factor I precursor. Nature vol. 306 pp. 609–611, 1983.

Lowe Biological effects of the insulin–like growth factors. In:Insulin–like growth factors:Molecular and cellular aspects. LeRoith Ed. CRC Press, Boca Raton pp. 49–85, 1991.

Boulter et al., "Isolation and Sequence of cDNA Clones Coding for the Precursor to the γ Subunit of Mouse Muscle Nicotinic Acetylcholine Receptor," 16 *J. Neuroscience Res.* 37, 1986.

Brinster et al., "Factors Affecting the Efficiency of Introducing Foreign DNA into Mice by Microinjecting Eggs," 82 *Proc. Natl. Acad. Sci. USA* 4438, 1985.

Buonanno et al., "A Universal Oligonucleotide Probe for Acetylcholine Receptor Genes," 261 *J. Biol. Chem.* 16451, 1986.

Carroll et al., "A 29–Nucleotide DNA Segment Containing an Evolutionarily Conserved Motif Is Required in cis for Cell–Type–Restricted Repression of the Chicken α–smooth Muscle Action Core Promoter," 8 *Mol. Cell. Biol.* 241, 1988.

Catanzaro et al., "Human Cardiac Myosin Heavy Chain Genes, Isolation of a Genomic DNA Clone and Its Characterization and of a Second Unique Clone Also Present in the Human Genome,"59 *Circulation Research* 655, 1986.

Chan et al., "Molecular Genetics of the Plasma Apolipoproteins," 10 *Mol. Biol. Cardiovascular System,* S. Chien, Ed., Lea & Febiger, Philadelphia, 183, 1990.

Chang et al., "The Complete Sequence of the Chicken α–Cardiac Actin Gene; A Highly Conserved Vertebrate Gene," 13 *Nuc. Acids Res.* 1223, 1985.

Chang et al., "Isolation and Characterization of Six Different Chick Actin Genes," 4 *Mol. Cell. Biol.* 2498, 1984.

Cheung et al., "Nucleotide Sequence of Cloned cDNA of Human Apolipoprotein A–I," 11 *Nuc. Acids Res.* 3703, 1983.

Chow et al., "A Combination of Closely Associated Positive and Negative cis–Acting Promoter Elements Regulates Transcription of the Skeletal α–Actin Gene," 10 *Mol. Cell. Biol.* 528, 1990.

Cooke et al., "Human Prolactin cDNA Structural Analysis and Evolutionary Comparisons," 356 *J. Biol. Chem.* 4007, 1981.

DeNoto et al., "Human Growth Hormone DNA Sequence and mRNA Structure: Possible Alternative Splicing," 9 *Nuc. Acids Res.* 3719, 1981.

DeVol et at., "Activation of Insulin–Like Growth Factor Gene Expression During Work–Induced Skeletal Muscle Growth," *American Physiological Society* E89–E95, 1990.

Dhawan, "Delivery of Human Growth Hormone by Injection of Genetically Engineered Myoblasts,"254 *Science* 1509, 1991.

Dobersen et al., "Herpes Simplex Virus Type 2 Induced Pyrimidine Nucleoside Kinase Enzymatic Basis for the Selective Antiherpetic Effect of 5–Halogenated Analogues of Deoxycytidine," 17 *Biochemistry* 920, 1978.

(List continued on next page.)

*Primary Examiner*—Nancy Degen
*Assistant Examiner*—John S. Brusca
*Attorney, Agent, or Firm*—Lyon & Lyon LLP

[57] ABSTRACT

This invention relates to gene therapy by using vectors which encode stable MRNA and methods of using such vectors. In particular, this invention relates to vectors which establish controlled expression of recombinant genes within tissues at certain levels. The vector includes a 5' flanking region which includes necessary sequences for expression of a nucleic acid cassette, a 3' flanking region including a 3' UTR and/or 3' NCR which stabilizes mRNA expressed from the nucleic acid cassette, and a linker which connects the 5' flanking region to a nucleic acid sequence. The linker has a position for inserting a nucleic acid cassette. The linker does not contain the coding sequence of a gene that the linker is naturally associated with. The 3' flanking region is 3' to the position for inserting the nucleic acid cassette. The expression vectors of the present invention can also be regulated by a regulatory system and/or constructed with a coating.

3 Claims, 30 Drawing Sheets

OTHER PUBLICATIONS

Eldridge et al., "Nucleotide Sequence of the Chicken Cardiac Alpha Actin Gene: Absence of Strong Homologies in the Promoter and 3'–Untranslated Regions with the Skeletal Alpha Actin Sequence," 36 *Gene* 55, 1985.

Fleischman, "Southwestern Internal Medicine Conference: Human Gene Therapy," 301 *Am. J. Med. Sci.* 353, 1991.

Florini, "Hormonal Control of Muscle Growth," 10 *Muscle & Nerve* 577, 1987.

Florini et al., "Highly Specific Inhibition of IGF–I–stimulated Differentiation by an Antisense Oligodeoxyribonucleotide to Myogenin mRNA," 265 *J. Biol. Chem.* 13435, 1990.

Fornwald et al., "The Complete Nucleotide Sequence of the Chick α–Actin Gene and Its Evolutionary Relationship to the Actin Gene Gamily," 10 *Nuc. Acids Res.* 3861, 1982.

French et al., "Analysis of a CR1 (Chicken Repeat) Sequence Flanking the 5' End of the Gene Encoding a–Skeletal Actin," 88 *Gene* 173, 1990.

Friedmann, "Progress Toward Human Gene Therapy," 244 *Science* 1275, 1989.

Garver et al., "Clonal Gene Therapy: Transplanted Mouse Fibroblast Clones Express Human α1–Antitrypsin Gene In Vivo," 347 *Science* 762, 1987.

Gehnrich et al., "Liver (B–type) Hosphofructokinase mRNA," 263 *J. Biol. Chem.* 11755, 1988.

Gillespie et al., "The 3'–Untranslated Sequence of Human Skeletal Muscle α–Actin mRNA," 5 *J. Muscle Res. Cell Motility* 457, 1984.

Grant, "Mammalian Nonsarcomeric Myosin Regulatory Light Chains Are Encoded by Two Differentially Regulated and Linked Genes," 111 *J. Cell Biol.* 1127, 1990.

Greaves et al., "Human CD2 3'–Flanking Sequences Confer High–Level, T Cell–Specific, Position–Independent Gene Expression in Transgenic Mice," 56 *Cell* 979, 1989.

Grichnik et al., "Tissue Restricted and Stage Specific Transcription is Maintained Within 411 Nucleotides Flanking the 5' End of the Chicken α–Skeletal Actin Gene," 14 *Nuc. Acids Res.* 1683, 1986.

Grosveld et. al., "Position–Independent, High–Level Expression of the Human β–Globin Gene in Transgenic Mice," 51 *Cell* 975, 1987.

Gubler et al., "Cloning and Sequence Analysis of cDNA for the Precursor of Human Growth Hormone–Releasing Factor, Somatocrinin," 80 *Proc. Natl. Acad. Sci. USA* 4311, 1983.

Gunning et al., "A Human β–Actin Expression Vector System Directs High–Level Accumulation of Antisense Transcripts," 84 *Proc. Natl. Acad. Sci. USA* 4831, 1987.

Gunning et al., "Chromosomal Location of the Co–Expressed Human Skeletal and Cardiac Actin Genes," 84 *Proc. Natl. Acad. Sci. USA* 1813, 1984.

Gunning et al., "Isolation and Characterization of Full–Length cDNA Clones for Human α–, β–, and γ–Actin mRNAs: Skeletal but Not Cytoplasmic Actins Have an Amino–Terminal Cysteine that is Subsequently Removed," 3 *Mol. Cell. Biol.* 787, 1983.

Hallauer et al., "Expression of a Quail Troponin I Gene in Transgenic Mice," M275 *Cellular a Mol. Biol. Muscle Dev.* 370.

Hamada et al., "Molecular Structure and Evolutionary Origin of Human Cardiac Muscle Actin" 79 *Proc. Natl. Acad. Sci. USA* 5901, 1982.

Hastings et al., "Generation of Troponin T Isoforms by Alternative RNA Splicing in Avian Skeletal Muscle, Conserved and Divergent Features in Birds and Mammals," 260 *J. Biol. Chem.* 13699, 1985.

Helfman et al., "Isolation and Sequence of a cDNA Clone That Contains the Entire Coding Region for Chicken Smooth–muscle α–Tropomyosin," 259 *J. Biol. Chem.* 14136, 1984.

Hentze, "Determinants and Regulation of Cytoplasmic mRNA Stability in Eukaryotic Cells," 1090 *Biochim. Biophys. Acta* 281, 1991.

Hoffman, "Putting New Muscle Into Gene Therapy," 254 *Science* 1455, 1991.

Hossle et al., "The Primary Structure of Chicken B–Creatine Kinase and Evidence for Heterogeneity of Its mRNA," 14 *Nuc. Acids Res.* 1449, 1986.

Hsu et al., "Conserved and Unique Sequences in the 3'–Untranslated Region of Rate Smooth–Muscle Alpha–Actin mRNA," 69 *Gene* 345, 1988.

Hu et al., "The Complete Sequence of the Mouse Skeletal α–Actin Gene Reveals Several Conserved and Inverted Repeat Sequences Outside of the Protein–Coding Region," 6 *Mol. Cell. Biol.* 15, 1986.

Jaenicke et al., "The Complete Sequence of the Human β–Myosin Heavy Chain Gene and a Comparative Analysis of Its Product," 8 *Genomics* 194, 1990.

Jansen et al., "Sequence of cDNA Encoding Human Insulin–Like Growth Factor I Precursor," 306 *Nature* 609, 1983.

Jin et al., "Isolation and Characterization of cDNA Clones Encoding Embryonic and Adult Isoforms of Rat Cardiac Troponin T," 264 *J. Biol. Chem.* 14471, 1989.

Jones, "Muscle Cell Differentiation and the Prospects for Genetic Engineering," 36 *Br. Med. Bull.* 173, 1980.

Kamada et al., "Structure of 3'–Downstream Segment of the Human Smooth Muscle (Aortic–Type) α–Actin–Encoding Gene and Isolation of the Specific DNA Probe," 84 *Gene* 455, 1989.

Lee et al., "Activation of Skeletal α–Actin Gene Transcription: The Cooperative Formation of Serum Response Factor–Binding Complexes over Positive cis–Acting Promoter Serum Response Elements Displaces a Negative–Acting Nuclear Factor Enriched in Replicating Myoblasts and Nonmyogenic Cells," 11 *Mol. Cell. Biol.* 5090, 1991.

Lee et al., "Displacement of BrdUrd–induced YY1 by Serum Response Factor Activates Actin Transcription in Embryonic Myoblasts," 89 *Proc. Natl. Acad. Sci. USA* 9814, 1992.

Lomedico et al., "The Structure and Evolution of the Two Nonallelic Rat Preproinsulin Genes," 18 *Cell* 545, 1979.

Zhu et al., "Phorbol Esters Selectively Downregulate Contractile Protein Gene Expression in Terminally Differentiated Myotubes Through Transcriptional Repression and Message Destabilization," 115 *J. Cell Biol.* 745, 1991.

Acsadi et al., "Direct Gene Transfer and Expression in Cardiac and Skeletal Muscle," 29 (4 part of 2) *Ped. Res.* 126A, 1991.

Andreadis et al., "Splicing of Mutually Exclusive Exons of Troponin T in Transfected Cells," L 502 *J. Cell. Biochem.* Alan R. Liss, Inc. New York, 119, 1987.

Applehans et al., "Characterization of a Human Genomic DNA Fragment Coding for a Myosin Heavy Chain," 65 *Hum. Genet.* 1983, 1983.

Arnold et al., "Regulated Expression of Transfected Muscle Specific Genes," L206 *Journal of Cellular Biochemistry*, Alan R. Liss, Inc., New York, 66, 1987.

Aviv et al., "Biosynthesis and Stability of Globin mRNA in Cultured Erythroleukemic Friend Cells," 503 *Cell* 495.

Baker et al., "Cloning and Expression of Full–Length cDNA Encoding Human Vitamin D Receptor," 85 *Proc. Natl. Acad. Sci. USA* 3294, 1988.

Barr et al, "Systemic Delivery of Recombinant Proteins by Genetically Modified Myoblasts," 254 *Science* 1507, 1991.

Bergsma et al., "Delimitation and Characterization of cis–Acting DNA Sequences Required for the Regulated Expression and Transcriptional Control of the Chicken Skeletal α–Actin Gene," 6 *Mol. Cell. Biol.* 2462, 1986.

VITAMIN D REGULATED SKELETAL ACTIN PROMOTER

Serum Response Factor

| DNA binding domain | Transactivation domain |

Vitamin D Receptor

| Vit D binding & DNA binding domain | Transactivation domain |

Construct Chimeric Transcription Factor by Swapping Domains.

| Vit D binding & DNA binding domain | Serum Response Transactivation Domain |

Replace the second SRE in the Skeletal actin promoter with the Vitamin D regulatory element.

SRE3 —— SRE2 —— SRE1 —— ATAAA ——

SRE3 —— VDRE —— SRE1 —— ATAAA ——

Transcription from the modified Skeletal actin/VDRE promoter is under the regulation of the Vitamin D Receptor/Serum Response Factor Chimera and Vitamin D Levels.

Fig.12

| | | | | | |
|---|---|---|---|---|---|
| 1 | AGCTTATCGA | TACCGTCGAC | CTCGAGGGGG | GGCCCGGTAC | CCAGCTTTTG |
| | TCGAATAGCT | ATGGCAGCTG | GAGCTCCCCC | CCGGGCCATG | GGTCGAAAAC |
| 51 | TTCCCTTTAG | TGAGGGTTAA | TTTCGAGCTT | GGCGTAATCA | TGGTCATAGC |
| | AAGGGAAATC | ACTCCCAATT | AAAGCTCGAA | CCGCATTAGT | ACCAGTATCG |
| 101 | TGTTTCCTGT | GTGAAATTGT | TATCCGCTCA | CAATTCCACA | CAACATACGA |
| | ACAAAGGACA | CACTTTAACA | ATAGGCGAGT | GTTAAGGTGT | GTTGTATGCT |
| 151 | GCCGGAAGCA | TAAAGTGTAA | AGCCTGGGGT | GCCTAATGAG | TGAGCTAACT |
| | CGGCCTTCGT | ATTTCACATT | TCGGACCCCA | CGGATTACTC | ACTCGATTGA |
| 201 | CACATTAATT | GCGTTGCGCT | CACTGCCCGC | TTTCCAGTCG | GGAAACCTGT |
| | GTGTAATTAA | CGCAACGCGA | GTGACGGGCG | AAAGGTCAGC | CCTTTGGACA |
| 251 | CGTGCCAGCT | GCATTAATGA | ATCGGCCAAC | GCGCGGGGAG | AGGCGGTTTG |
| | GCACGGTCGA | CGTAATTACT | TAGCCGGTTG | CGCGCCCCTC | TCCGCCAAAC |
| 301 | CGTATTGGGC | GCTCTTCCGC | TTCCTCGCTC | ACTGACTCGC | TGCGCTCGGT |
| | GCATAACCCG | CGAGAAGGCG | AAGGAGCGAG | TGACTGAGCG | ACGCGAGCCA |
| 351 | CGTTCGGCTG | CGGCGAGCGG | TATCAGCTCA | CTCAAAGGCG | GTAATACGGT |
| | GCAAGCCGAC | GCCGCTCGCC | ATAGTCGAGT | GAGTTTCCGC | CATTATGCCA |
| 401 | TATCCACAGA | ATCAGGGGAT | AACGCAGGAA | AGAACATGTG | AGCAAAAGGC |
| | ATAGGTGTCT | TAGTCCCCTA | TTGCGTCCTT | TCTTGTACAC | TCGTTTTCCG |
| 451 | CAGCAAAAGG | CCAGGAACCG | TAAAAAGGCC | GCGTTGCTGG | CGTTTTTCCA |
| | GTCGTTTTCC | GGTCCTTGGC | ATTTTTCCGG | CGCAACGACC | GCAAAAAGGT |
| 501 | TAGGCTCCGC | CCCCCTGACG | AGCATCACAA | AAATCGACGC | TCAAGTCAGA |
| | ATCCGAGGCG | GGGGGACTGC | TCGTAGTGTT | TTTAGCTGCG | AGTTCAGTCT |
| 551 | GGTGGCGAAA | CCCGACAGGA | CTATAAAGAT | ACCAGGCGTT | TCCCCCTGGA |
| | CCACCGCTTT | GGGCTGTCCT | GATATTTCTA | TGGTCCGCAA | AGGGGGACCT |
| 601 | AGCTCCCTCG | TGCGCTCTCC | TGTTCCGACC | CTGCCGCTTA | CCGGATACCT |
| | TCGAGGGAGC | ACGCGAGAGG | ACAAGGCTGG | GACGGCGAAT | GGCCTATGGA |
| 651 | GTCCGCCTTT | CTCCCTTCGG | GAAGCGTGGC | GCTTTCTCAT | AGCTCACGCT |
| | CAGGCGGAAA | GAGGGAAGCC | CTTCGCACCG | CGAAAGAGTA | TCGAGTGCGA |
| 701 | GTAGGTATCT | CAGTTCGGTG | TAGGTCGTTC | GCTCCAAGCT | GGGCTGTGTG |
| | CATCCATAGA | GTCAAGCCAC | ATCCAGCAAG | CGAGGTTCGA | CCCGACACAC |
| 751 | CACGAACCCC | CCGTTCAGCC | CGACCGCTGC | GCCTTATCCG | GTAACTATCG |
| | GTGCTTGGGG | GGCAAGTCGG | GCTGGCGACG | CGGAATAGGC | CATTGATAGC |
| 801 | TCTTGAGTCC | AACCCGGTAA | GACACGACTT | ATCGCCACTG | GCAGCAGCCA |
| | AGAACTCAGG | TTGGGCCATT | CTGTGCTGAA | TAGCGGTGAC | CGTCGTCGGT |

Fig.15

| | | | | | |
|---|---|---|---|---|---|
| 851 | CTGGTAACAG GACCATTGTC | GATTAGCAGA CTAATCGTCT | GCGAGGTATG CGCTCCATAC | TAGGCGGTGC ATCCGCCACG | TACAGAGTTC ATGTCTCAAG |
| 901 | TTGAAGTGGT AACTTCACCA | GGCCTAACTA CCGGATTGAT | CGGCTACACT GCCGATGTGA | AGAAGGACAG TCTTCCTGTC | TATTTGGTAT ATAAACCATA |
| 951 | CTGCGCTCTG GACGCGAGAC | CTGAAGCCAG GACTTCGGTC | TTACCTTCGG AATGGAAGCC | AAAAAGAGTT TTTTTCTCAA | GGTAGCTCTT CCATCGAGAA |
| 1001 | GATCCGGCAA CTAGGCCGTT | ACAAACCACC TGTTTGGTGG | GCTGGTAGCG CGACCATCGC | GTGGTTTTTT CACCAAAAAA | TGTTTGCAAG ACAAACGTTC |
| 1051 | CAGCAGATTA GTCGTCTAAT | CGCGCAGAAA GCGCGTCTTT | AAAAGGATCT TTTTCCTAGA | CAAGAAGATC GTTCTTCTAG | CTTTGATCTT GAAACTAGAA |
| 1101 | TTCTACGGGG AAGATGCCCC | TCTGACGCTC AGACTGCGAG | AGTGGAACGA TCACCTTGCT | AAACTCACGT TTTGAGTGCA | TAAGGGATTT ATTCCCTAAA |
| 1151 | TGGTCATGAG ACCAGTACTC | ATTATCAAAA TAATAGTTTT | AGGATCTTCA TCCTAGAAGT | CCTAGATCCT GGATCTAGGA | TTTAAATTAA AAATTTAATT |
| 1201 | AAATGAAGTT TTTACTTCAA | TTAAATCAAT AATTTAGTTA | CTAAAGTATA GATTTCATAT | TATGAGTAAA ATACTCATTT | CTTGGTCTGA GAACCAGACT |
| 1251 | CAGTTACCAA GTCAATGGTT | TGCTTAATCA ACGAATTAGT | GTGAGGCACC CACTCCGTGG | TATCTCAGCG ATAGAGTCGC | ATCTGTCTAT TAGACAGATA |
| 1301 | TTCGTTCATC AAGCAAGTAG | CATAGTTGCC GTATCAACGG | TGACTCCCCG ACTGAGGGGC | TCGTGTAGAT AGCACATCTA | AACTACGATA TTGATGCTAT |
| 1351 | CGGGAGGGCT GCCCTCCCGA | TACCATCTGG ATGGTAGACC | CCCCAGTGCT GGGGTCACGA | GCAATGATAC CGTTACTATG | CGCGAGACCC GCGCTCTGGG |
| 1401 | ACGCTCACCG TGCGAGTGGC | GCTCCAGATT CGAGGTCTAA | TATCAGCAAT ATAGTCGTTA | AAACCAGCCA TTTGGTCGGT | GCCGGAAGGG CGGCCTTCCC |
| 1451 | CCGAGCGCAG GGCTCGCGTC | AAGTGGTCCT TTCACCAGGA | GCAACTTTAT CGTTGAAATA | CCGCCTCCAT GGCGGAGGTA | CCAGTCTATT GGTCAGATAA |
| 1501 | AATTGTTGCC TTAACAACGG | GGGAAGCTAG CCCTTCGATC | AGTAAGTAGT TCATTCATCA | TCGCCAGTTA AGCGGTCAAT | ATAGTTTGCG TATCAAACGC |
| 1551 | CAACGTTGTT GTTGCAACAA | GCCATTGCTA CGGTAACGAT | CAGGCATCGT GTCCGTAGCA | GGTGTCACGC CCACAGTGCG | TCGTCGTTTG AGCAGCAAAC |
| 1601 | GTATGGCTTC CATACCGAAG | ATTCAGCTCC TAAGTCGAGG | GGTTCCCAAC CCAAGGGTTG | GATCAAGGCG CTAGTTCCGC | AGTTACATGA TCAATGTACT |
| 1651 | TCCCCCATGT AGGGGGTACA | TGTGCAAAAA ACACGTTTTT | AGCGGTTAGC TCGCCAATCG | TCCTTCGGTC AGGAAGCCAG | CTCCGATCGT GAGGCTAGCA |

Fig.15A

| | | | | | |
|---|---|---|---|---|---|
| 1701 | TGTCAGAAGT<br>ACAGTCTTCA | AAGTTGGCCG<br>TTCAACCGGC | CAGTGTTATC<br>GTCACAATAG | ACTCATGGTT<br>TGAGTACCAA | ATGGCAGCAC<br>TACCGTCGTG |
| 1751 | TGCATAATTC<br>ACGTATTAAG | TCTTACTGTC<br>AGAATGACAG | ATGCCATCCG<br>TACGGTAGGC | TAAGATGCTT<br>ATTCTACGAA | TTCTGTGACT<br>AAGACACTGA |
| 1801 | GGTGAGTACT<br>CCACTCATGA | CAACCAAGTC<br>GTTGGTTCAG | ATTCTGAGAA<br>TAAGACTCTT | TAGTGTATGC<br>ATCACATACG | GGCGACCGAG<br>CCGCTGGCTC |
| 1851 | TTGCTCTTGC<br>AACGAGAACG | CCGGCGTCAA<br>GGCCGCAGTT | TACGGGATAA<br>ATGCCCTATT | TACCGCGCCA<br>ATGGCGCGGT | CATAGCAGAA<br>GTATCGTCTT |
| 1901 | CTTTAAAAGT<br>GAAATTTTCA | GCTCATCATT<br>CGAGTAGTAA | GGAAAACGTT<br>CCTTTTGCAA | CTTCGGGGCG<br>GAAGCCCCGC | AAAACTCTCA<br>TTTTGAGAGT |
| 1951 | AGGATCTTAC<br>TCCTAGAATG | CGCTGTTGAG<br>GCGACAACTC | ATCCAGTTCG<br>TAGGTCAAGC | ATGTAACCCA<br>TACATTGGGT | CTCGTGCACC<br>GAGCACGTGG |
| 2001 | CAACTGATCT<br>GTTGACTAGA | TCAGCATCTT<br>AGTCGTAGAA | TTACTTTCAC<br>AATGAAAGTG | CAGCGTTTCT<br>GTCGCAAAGA | GGGTGAGCAA<br>CCCACTCGTT |
| 2051 | AAACAGGAAG<br>TTTGTCCTTC | GCAAAATGCC<br>CGTTTTACGG | GCAAAAAGG<br>CGTTTTTTCC | GAATAAGGGC<br>CTTATTCCCG | GACACGGAAA<br>CTGTGCCTTT |
| 2101 | TGTTGAATAC<br>ACAACTTATG | TCATACTCTT<br>AGTATGAGAA | CCTTTTTCAA<br>GGAAAAAGTT | TATTATTGAA<br>ATAATAACTT | GCATTTATCA<br>CGTAAATAGT |
| 2151 | GGGTTATTGT<br>CCCAATAACA | CTCATGAGCG<br>GAGTACTCGC | GATACATATT<br>CTATGTATAA | TGAATGTATT<br>ACTTACATAA | TAGAAAAATA<br>ATCTTTTTAT |
| 2201 | AACAAATAGG<br>TTGTTTATCC | GGTTCCGCGC<br>CCAAGGCGCG | ACATTTCCCC<br>TGTAAAGGGG | GAAAAGTGCC<br>CTTTTCACGG | ACCTAAATTG<br>TGGATTTAAC |
| 2251 | TAAGCGTTAA<br>ATTCGCAATT | TATTTTGTTA<br>ATAAAACAAT | AAATTCGCGT<br>TTTAAGCGCA | TAAATTTTTG<br>ATTTAAAAAC | TTAAATCAGC<br>AATTTAGTCG |
| 2301 | TCATTTTTTA<br>AGTAAAAAAT | ACCAATAGGC<br>TGGTTATCCG | CGAAATCGGC<br>GCTTTAGCCG | AAAATCCCTT<br>TTTTAGGGAA | ATAAATCAAA<br>TATTTAGTTT |
| 2351 | AGAATAGACC<br>TCTTATCTGG | GAGATAGGGT<br>CTCTATCCCA | TGAGTGTTGT<br>ACTCACAACA | TCCAGTTTGG<br>AGGTCAAACC | AACAAGAGTC<br>TTGTTCTCAG |
| 2401 | CACTATTAAA<br>GTGATAATTT | GAACGTGGAC<br>CTTGCACCTG | TCCAACGTCA<br>AGGTTGCAGT | AAGGGCGAAA<br>TTCCCGCTTT | AACCGTCTAT<br>TTGGCAGATA |
| 2451 | CAGGGCGATG<br>GTCCCGCTAC | GCCCACTACG<br>CGGGTGATGC | TGAACCATCA<br>ACTTGGTAGT | CCCTAATCAA<br>GGGATTAGTT | GTTTTTTGGG<br>CAAAAAACCC |
| 2501 | GTCGAGGTGC<br>CAGCTCCACG | CGTAAAGCAC<br>GCATTTCGTG | TAAATCGGAA<br>ATTTAGCCTT | CCCTAAAGGG<br>GGGATTTCCC | AGCCCCGAT<br>TCGGGGCTA |

Fig.15B

| | | | | | |
|---|---|---|---|---|---|
| 2551 | TTAGAGCTTG<br>AATCTCGAAC | ACGGGGAAAG<br>TGCCCCTTTC | CCGGCGAACG<br>GGCCGCTTGC | TGGCGAGAAA<br>ACCGCTCTTT | GGAAGGGAAG<br>CCTTCCCTTC |
| 2601 | AAAGCGAAAG<br>TTTCGCTTTC | GAGCGGGCGC<br>CTCGCCCGCG | TAGGGCGCTG<br>ATCCCGCGAC | GCAAGTGTAG<br>CGTTCACATC | CGGTCACGCT<br>GCCAGTGCGA |
| 2651 | GCGCGTAACC<br>CGCGCATTGG | ACCACACCCG<br>TGGTGTGGGC | CCGCGCTTAA<br>GGCGCGAATT | TGCGCCGCTA<br>ACGCGGCGAT | CAGGGCGCGT<br>GTCCCGCGCA |
| 2701 | CCCATTCGCC<br>GGGTAAGCGG | ATTCAGGCTG<br>TAAGTCCGAC | CGCAACTGTT<br>GCGTTGACAA | GGGAAGGGCG<br>CCCTTCCCGC | ATCGGTGCGG<br>TAGCCACGCC |
| 2751 | GCCTCTTCGC<br>CGGAGAAGCG | TATTACGCCA<br>ATAATGCGGT | GCTGGCGAAA<br>CGACCGCTTT | GGGGGATGTG<br>CCCCCTACAC | CTGCAAGGCG<br>GACGTTCCGC |
| 2801 | ATTAAGTTGG<br>TAATTCAACC | GTAACGCCAG<br>CATTGCGGTC | GGTTTTCCCA<br>CCAAAAGGGT | GTCACGACGT<br>CAGTGCTGCA | TGTAAAACGA<br>ACATTTTGCT |
| 2851 | CGGCCAGTGA<br>GCCGGTCACT | ATTGTAATAC<br>TAACATTATG | GACTCACTAT<br>CTGAGTGATA | AGGGCGAATT<br>TCCCGCTTAA | GGAGCTCCAC<br>CCTCGAGGTG |
| 2901 | CGCGGTGGCG<br>GCGCCACCGC | GCCGCTCTAG<br>CGGCGAGATC | AACTAGTGGA<br>TTGATCACCT | TCCTCTAGAG<br>AGGAGATCTC | TCTGCCTGCC<br>AGACGGACGG |
| 2951 | CCCTGCCTGG<br>GGGACGGACC | CACAGCCCGT<br>GTGTCGGGCA | ACCTGGCCGC<br>TGGACCGGCG | ACGCTCCCTC<br>TGCGAGGGAG | ACAGGTGAAG<br>TGTCCACTTC |
| 3001 | CTCGAAAACT<br>GAGCTTTTGA | CCGTCCCCGT<br>GGCAGGGGCA | AAGGAGCCCC<br>TTCCTCGGGG | GCTGCCCCCC<br>CGACGGGGGG | GAGGCCTCCT<br>CTCCGGAGGA |
| 3051 | CCCTCACGCC<br>GGGAGTGCGG | TCGCTGCGCT<br>AGCGACGCGA | CCCGGCTCCC<br>GGGCCGAGGG | GCACGGCCCT<br>CGTGCCGGGA | GGGAGAGGCC<br>CCCTCTCCGG |
| 3101 | CCCACCGCTT<br>GGGTGGCGAA | CGTCCTTAAC<br>GCAGGAATTG | GGGCCCGGCG<br>CCCGGGCCGC | GTGCCGGGGG<br>CACGGCCCCC | ATTATTTCGG<br>TAATAAAGCC |
| 3151 | CCCCGGCCCC<br>GGGGCCGGGG | GGGGGGGCCC<br>CCCCCCCGGG | GGCAGACGCT<br>CCGTCTGCGA | CCTTATACGG<br>GGAATATGCC | CCCGGCCTCG<br>GGGCCGGAGC |
| 3201 | CTCACCTGGG<br>GAGTGGACCC | CCGCGGCCAG<br>GGCGCCGGTC | GAGCGCCTTC<br>CTCGCGGAAG | TTTGGGCAGC<br>AAACCCGTCG | GCCGGGCCGG<br>CGGCCCGGCC |
| 3251 | GGCCGCGCCG<br>CCGGCGCGGC | GGCCCGACAC<br>CCGGGCTGTG | CCAAATATGG<br>GGTTTATACC | CGACGGCCGG<br>GCTGCCGGCC | GGCCGCATTC<br>CCGGCGTAAG |
| 3301 | CTGGGGGCCG<br>GACCCCCGGC | GGCGGTGCTC<br>CCGCCACGAG | CCGCCCGCCT<br>GGCGGGCGGA | CGATAAAAGG<br>GCTATTTTCC | CTCCGGGGCC<br>GAGGCCCCGG |
| 3351 | GGCGGCGGCC<br>CCGCCGCCGG | CACGAGCTAC<br>GTGCTCGATG | CCGGAGGAGC<br>GGCCTCCTCG | GGGAGGCGTC<br>CCCTCCGCAG | TCTGCCAGCG<br>AGACGGTCGC |

Fig.15C

| | | | | | |
|---|---|---|---|---|---|
| 3401 | GCCCGACGCG CGGGCTGCGC | CAGTCAGCAC GTCAGTCGTG | AGGTAGGTGG TCCATCCACC | GCACCGCGCC CGTGGCGCGG | GTGCCGTGCC CACGGCACGG |
| 3451 | GTGCCGTGCC CACGGCACGG | GCCCGGCGCC CGGGCCGCGG | CCTTCGCGGG GGAAGCGCCC | GCCGTCGTGT CGGCAGCACA | GGGCCCTCCG CCCGGGAGGC |
| 3501 | TGGGCCCCGC ACCCGGGGCG | CGTCACCCTG GCAGTGGGAC | AGCCTCACGG TCGGAGTGCC | CCCCGTGCCC GGGGCACGGG | CGCAGACAGC GCGTCTGTCG |
| 3551 | CAGCACCATG GTCGTGGTAC | GGAAAAATCA CCTTTTTAGT | GCAGTCTTCC CGTCAGAAGG | AACCCAATTA TTGGGTTAAT | TTTAAGTGCT AAATTCACGA |
| 3601 | GCTTTTGTGA CGAAAACACT | TTTCTTGAAG AAAGAACTTC | GTGAAGATGC CACTTCTACG | ACACCATGTC TGTGGTACAG | CTCCTCGCAT GAGGAGCGTA |
| 3651 | CTCTTCTACC GAGAAGATGG | TGGCGCTGTG ACCGCGACAC | CCTGCTCACC GGACGAGTGG | TTCACCAGCT AAGTGGTCGA | CTGCCACGGC GACGGTGCCG |
| 3701 | TGGACCGGAG ACCTGGCCTC | ACGCTCTGCG TGCGAGACGC | GGGCTGAGCT CCCGACTCGA | GGTGGATGCT CCACCTACGA | CTTCAGTTCG GAAGTCAAGC |
| 3751 | TGTGTGGAGA ACACACCTCT | CAGGGGCTTT GTCCCCGAAA | TATTTCAACA ATAAAGTTGT | AGCCCACAGG TCGGGTGTCC | GTATGGCTCC CATACCGAGG |
| 3801 | AGCAGTCGGA TCGTCAGCCT | GGGCGCCTCA CCCGCGGAGT | GACAGGCATC CTGTCCGTAG | GTGGATGAGT CACCTACTCA | GCTGCTTCCG CGACGAAGGC |
| 3851 | GAGCTGTGAT CTCGACACTA | CTAAGGAGGC GATTCCTCCG | TGGAGATGTA ACCTCTACAT | TTGCGCACCC AACGCGTGGG | CTCAAGCCTG GAGTTCGGAC |
| 3901 | CCAAGTCAGC GGTTCAGTCG | TCGCTCTGTC AGCGAGACAG | CGTGCCCAGC GCACGGGTCG | GCCACACCGA CGGTGTGGCT | CATGCCCAAG GTACGGGTTC |
| 3951 | ACCCAGAAGG TGGGTCTTCC | AAGTACATTT TTCATGTAAA | GAAGAACGCA CTTCTTGCGT | AGTAGAGGGA TCATCTCCCT | GTGCAGGAAA CACGTCCTTT |
| 4001 | CAAGAACTAC GTTCTTGATG | AGGATGTAGG TCCTACATCC | AAGACCCTCC TTCTGGGAGG | TGAGGAGTGA ACTCCTCACT | AGAGTGACAT TCTCACTGTA |
| 4051 | GCCACCGCAG CGGTGGCGTC | GATCCCCCGG CTAGGGGCC | GCTGCAGGAA CGACGTCCTT | TTCGATGGCC AAGCTACCGG | CATCCATTGT GTAGGTAACA |
| 4101 | CCACCGTAAA GGTGGCATTT | TGCTTCTAAA ACGAAGATTT | CATGTTTACA GTACAAATGT | TGATCACTTT ACTAGTGAAA | GCCAACCACA CGGTTGGTGT |
| 4151 | CTCAGGATGA GAGTCCTACT | CAATCTTGTA GTTAGAACAT | GGTTCCAGGC CCAAGGTCCG | TGCTGAGGAC ACGACTCCTG | CTGCACCAGC GACGTGGTCG |
| 4201 | CATGCAACTT GTACGTTGAA | TCTATTTTGT AGATAAAACA | AACAATTTCT TTGTTAAAGA | GGTTACTGTT CCAATGACAA | GCTGCAAAGC CGACGTTTCG |

Fig.15D

| | | | | | |
|---|---|---|---|---|---|
| 4251 | TCCATGTGAC<br>AGGTACACTG | ACAGTGTATG<br>TGTCACATAC | TAAAGTGTAC<br>ATTTCACATG | ATAAATTAAT<br>TATTTAATTA | TTATTTTACC<br>AATAAAATGG |
| 4301 | TCGTTTTGTT<br>AGCAAAACAA | TGTTTTTAAA<br>ACAAAAATTT | ACCAATGCCC<br>TGGTTACGGG | TGTGGAAGGA<br>ACACCTTCCT | AACATAAAAC<br>TTGTATTTTG |
| 4351 | TTCAAGAAGC<br>AAGTTCTTCG | ATTAAATCAT<br>TAATTTAGTA | CAGTCATTCT<br>GTCAGTAAGA | GTCACACCCC<br>CAGTGTGGGG | TAATGCAGTT<br>ATTACGTCAA |
| 4401 | GTTTCTGTCA<br>CAAAGACAGT | TCATTTCCCT<br>AGTAAAGGGA | GGGCTCTTCC<br>CCCGAGAAGG | ATCTCTGCT<br>TAGAGAGCGA | GACCTGGGAC<br>CTGGACCCTG |
| 4451 | TGGGTGCTGG<br>ACCCACGACC | GGCTGGGAGC<br>CCGACCCTCG | AGGGGTTGGG<br>TCCCCAACCC | GCTCTCCAGG<br>CGAGAGGTCC | GAGAGATGGC<br>CTCTCTACCG |
| 4501 | ATGGGGAGAG<br>TACCCCTCTC | TGATGGGATA<br>ACTACCCTAT | CTGCTGGGGG<br>GACGACCCCC | GGGGGGACTC<br>CCCCCCTGAG | ACCCTGCTGT<br>TGGGACGACA |
| 4551 | GGGCTGCAGG<br>CCCGACGTCC | AAGCCCATTG<br>TTCGGGTAAC | GTGCAGAGAG<br>CACGTCTCTC | CAGCCTGGGA<br>GTCGGACCCT | TGCCCATGAC<br>ACGGGTACTG |
| 4601 | ACGGGCACCC<br>TGCCCGTGGG | ACTGCACCGT<br>TGACGTGGCA | GTTTCTCCCA<br>CAAAGAGGGT | TGCCCAGTAG<br>ACGGGTCATC | GGAAAGGGTT<br>CCTTTCCCAA |
| 4651 | ACGAGCGCCG<br>TGCTCGCGGC | TTCATTCTCA<br>AAGTAAGAGT | GCTTGTGAAG<br>CGAACACTTC | GATTTTGTTG<br>CTAAAACAAC | GGCTCAGCCT<br>CCGAGTCGGA |
| 4701 | GCCAGAGCAG<br>CGGTCTCGTC | TAGCCAGGCA<br>ATCGGTCCGT | TGCCTGTGCA<br>ACGGACACGT | GCTCCGAGCT<br>CGAGGCTCGA | GTGATGGACA<br>CACTACCTGT |
| 4751 | GAGGCAAGGC<br>CTCCGTTCCG | TGCAGCTGAG<br>ACGTCGACTC | GCCAGGTGGT<br>CGGTCCACCA | GGGCACAGGT<br>CCCGTGTCCA | TAAATTAAGA<br>ATTTAATTCT |
| 4801 | GCTTTCCACT<br>CGAAAGGTGA | CCACTTATGG<br>GGTGAATACC | AAAGCCCTCC<br>TTTCGGGAGG | TGCACTCACC<br>ACGTGAGTGG | CTGTCCCTGG<br>GACAGGGACC |
| 4851 | GGCTGGGGGC<br>CCGACCCCCG | AGCCAGGGCC<br>TCGGTCCCGG | ACTTCCTCAC<br>TGAAGGAGTG | CCCACCTGAC<br>GGGTGGACTG | ACACAAGGCT<br>TGTGTTCCGA |
| 4901 | TTGCCTGCAC<br>AACGGACGTG | AGCCAGGACC<br>TCGGTCCTGG | TCCTGTGGCC<br>AGGACACCGG | ACAGACTCTT<br>TGTCTGAGAA | ATAGATTCGC<br>TATCTAAGCG |
| 4951 | TGTGCCCTAG<br>ACACGGGATC | GAGACCAGGG<br>CTCTGGTCCC | GGCTTTCCCT<br>CCGAAAGGGA | GCCTGGCCTT<br>CGGACCGGAA | CTGGCCCCGG<br>GACCGGGGCC |
| 5001 | CGACACTGCA<br>GCTGTGACGT | GGAGCTGCCC<br>CCTCGACGGG | TATCTGCCTC<br>ATAGACGGAG | CTCTTAGATG<br>GAGAATCTAC | GTCCTGGCAG<br>CAGGACCGTC |
| 5051 | GAAGGCTGCA<br>CTTCCGACGT | CTTGGCTTGG<br>GAACCGAACC | GGCTGATCCA<br>CCGACTAGGT | TATTACCACT<br>ATAATGGTGA | GCAGTAGGGA<br>CGTCATCCCT |

Fig.15E

| | | | | | |
|---|---|---|---|---|---|
| 5101 | CAGCACTGCT | GGAAGAAAAG | ATGATTTTCA | ACTGAACTTA | CTATCCAGGC |
| | GTCGTGACGA | CCTTCTTTTC | TACTAAAAGT | TGACTTGAAT | GATAGGTCCG |
| 5151 | AGGTTATTGC | TTTATTGTGA | TGGTGCTAAG | AGTGCGTTCT | TTCTCACTGT |
| | TCCAATAACG | AAATAACACT | ACCACGATTC | TCACGCAAGA | AAGAGTGACA |
| 5201 | AATGATTTTG | CCCTCATGTG | TGAATACACT | TTCCAATAAC | AGCACAGCCT |
| | TTACTAAAAC | GGGAGTACAC | ACTTATGTGA | AAGGTTATTG | TCGTGTCGGA |
| 5251 | CCAAAGGGAA | TTTCTGCAGG | AAGAGACAGT | ACCTGGTGTG | GGAAGTCCCT |
| | GGTTTCCCTT | AAAGACGTCC | TTCTCTGTCA | TGGACCACAC | CCTTCAGGGA |
| 5301 | GTGCAGCCCT | ATGTGCTTCA | AGCTGAATGG | CTGGGACTGG | CTGGGAGAGC |
| | CACGTCGGGA | TACACGAAGT | TCGACTTACC | GACCCTGACC | GACCCTCTCG |
| 5351 | AGGATCACAT | CCTTTCTTAA | AAAGACAAAC | AGAAGGTAGT | GTGTGACCTT |
| | TCCTAGTGTA | GGAAAGAATT | TTTCTGTTTG | TCTTCCATCA | CACACTGGAA |
| 5401 | GCTGTATTTA | CTATTTACGC | GTTGTTGTTC | AGTGGCACAT | ACCTCAACGG |
| | CGACATAAAT | GATAAATGCG | CAACAACAAG | TCACCGTGTA | TGGAGTTGCC |
| 5451 | GGATATGGAG | AGCTATTTCC | CCAACCCTCG | CTGCTGGACC | CTGATCTGGG |
| | CCTATACCTC | TCGATAAAGG | GGTTGGGAGC | GACGACCTGG | GACTAGACCC |
| 5501 | GTTTTCCTGT | AGCTTAAGCG | GTGCCAACTG | CTTAAGTGAT | TGTAGAATCA |
| | CAAAAGGACA | TCGAATTCGC | CACGGTTGAC | GAATTCACTA | ACATCTTAGT |
| 5551 | GTAAGGCTGG | AAAAGACCAC | AGATCATTAA | GTCCAACTGT | CAGCCCCATC |
| | CATTCCGACC | TTTTCTGGTG | TCTAGTAATT | CAGGTTGACA | GTCGGGGTAG |
| 5601 | CCCACCGCGC | CCACTGTCAC | TCAGTGCCAC | ATCCACGCAT | TTCTTGAACA |
| | GGGTGGCGCG | GGTGACAGTG | AGTCACGGTG | TAGGTGCGTA | AAGAACTTGT |
| 5651 | TCTCCAGGGA | CAGTGACTCC | ACCCGTCACC | AGCTGTGCTT | CAGAGCAGGC |
| | AGAGGTCCCT | GTCACTGAGG | TGGGCAGTGG | TCGACACGAA | GTCTCGTCCG |
| 5701 | AGGGTGACAG | TCTCAGTGCC | AGTTGCATCC | TGCTGAAGAG | CTTAACAGTG |
| | TCCCACTGTC | AGAGTCACGG | TCAACGTAGG | ACGACTTCTC | GAATTGTCAC |
| 5751 | CAGTTTAACA | ACGGACTGAT | TTGTTGATGT | GGTTGCTGAA | TCAGTACGTT |
| | GTCAAATTGT | TGCCTGACTA | AACAACTACA | CCAACGACTT | AGTCATGCAA |
| 5801 | GAGATGTCAC | TAAACTTTTT | GGAGATTAAT | TTCAGGATGG | AACACATTCT |
| | CTCTACAGTG | ATTTGAAAAA | CCTCTAATTA | AAGTCCTACC | TTGTGTAAGA |
| 5851 | TAACCCTGAA | ACCAGCCTTT | GATTTGGGCT | TGGCATTTGC | AGAATTTGCA |
| | ATTGGGACTT | TGGTCGGAAA | CTAAACCCGA | ACCGTAAACG | TCTTAAACGT |
| 5901 | GGAAAAGATT | GTTTGGGAAC | AGATGAATGG | AATTTCCACC | AAACAGAAAA |
| | CCTTTTCTAA | CAAACCCTTG | TCTACTTACC | TTAAAGGTGG | TTTGTCTTTT |

Fig.15F

| | | | | | |
|---|---|---|---|---|---|
| 5951 | TTAACACTTA | CACCAGTTTG | AGTCTGGTCT | TCGTTGGATA | TTTCTTAAGA |
| | AATTGTGAAT | GTGGTCAAAC | TCAGACCAGA | AGCAACCTAT | AAAGAATTCT |
| 6001 | ATCTCATCAT | CCTCCCTGCT | CTTGGACCAG | TGCTGCTGAC | AGGAGGTGGA |
| | TAGAGTAGTA | GGAGGGACGA | GAACCTGGTC | ACGACGACTG | TCCTCCACCT |
| 6051 | GGATCATCAG | GGTCAGCATC | CTCAGCATCT | AGGGATGTGC | ACTATGTGTG |
| | CCTAGTAGTC | CCAGTCGTAG | GAGTCGTAGA | TCCCTACACG | TGATACACAC |
| 6101 | ATGGTGACAC | TTTAGAGAAC | TGCTTTGATT | CCCCAGGGCT | TTCCCTCTCT |
| | TACCACTGTG | AAATCTCTTG | ACGAAACTAA | GGGGTCCCGA | AAGGGAGAGA |
| 6151 | TCCATGCAGG | GCTCACTATC | AGCCCTGAAA | GTCCAACTTT | CTGAACTTCC |
| | AGGTACGTCC | CGAGTGATAG | TCGGGACTTT | CAGGTTGAAA | GACTTGAAGG |
| 6201 | AGCACCGTCT | GCTCCTGGTA | GGCTGTTCCA | TAGAGGCCAC | AGGGACTGTA |
| | TCGTGGCAGA | CGAGGACCAT | CCGACAAGGT | ATCTCCGGTG | TCCCTGACAT |
| 6251 | GCCAGGCATG | ACCTTTTCCC | AGCCGTGCTC | TGAATCCAGC | ACTGGTGGCT |
| | CGGTCCGTAC | TGGAAAAGGG | TCGGCACGAG | ACTTAGGTCG | TGACCACCGA |
| 6301 | GGGAGGCAGC | TCTGGTCCTG | GGGTGCTGCA | GTGAGCCAGG | GAACA |
| | CCCTCCGTCG | AGACCAGGAC | CCCACGACGT | CACTCGGTCC | CTTGT |

Fig.15G

| | | | | | |
|---|---|---|---|---|---|
| 1 | GGCCGCTCTA | GAACTAGTGG | ATCCTCTAGA | GTCTGCCTGC | CCCCTGCCTG |
| | CCGGCGAGAT | CTTGATCACC | TAGGAGATCT | CAGACGGACG | GGGGACGGAC |
| 51 | GCACAGCCCG | TACCTGGCCG | CACGCTCCCT | CACAGGTGAA | GCTCGAAAAC |
| | CGTGTCGGGC | ATGGACCGGC | GTGCGAGGGA | GTGTCCACTT | CGAGCTTTTG |
| 101 | TCCGTCCCCG | TAAGGAGCCC | CGCTGCCCCC | CGAGGCCTCC | TCCCTCACGC |
| | AGGCAGGGGC | ATTCCTCGGG | GCGACGGGGG | GCTCCGGAGG | AGGGAGTGCG |
| 151 | CTCGCTGCGC | TCCCGGCTCC | CGCACGGCCC | TGGGAGAGGC | CCCCACCGCT |
| | GAGCGACGCG | AGGGCCGAGG | GCGTGCCGGG | ACCCTCTCCG | GGGGTGGCGA |
| 201 | TCGTCCTTAA | CGGGCCCGGC | GGTGCCGGGG | GATTATTTCG | GCCCCGGCCC |
| | AGCAGGAATT | GCCCGGGCCG | CCACGGCCCC | CTAATAAAGC | CGGGGCCGGG |
| 251 | CGGGGGGGCC | CGGCAGACGC | TCCTTATACG | GCCCGGCCTC | GCTCACCTGG |
| | GCCCCCCCGG | GCCGTCTGCG | AGGAATATGC | CGGGCCGGAG | CGAGTGGACC |
| 301 | GCCGCGGCCA | GGAGCGCCTT | CTTTGGGCAG | CGCCGGGCCG | GGGCCGCGCC |
| | CGGCGCCGGT | CCTCGCGGAA | GAAACCCGTC | GCGGCCCGGC | CCCGGCGCGG |
| 351 | GGGCCCGACA | CCCAAATATG | GCGACGGCCG | GGGCCGCATT | CCTGGGGGCC |
| | CCCGGGCTGT | GGGTTTATAC | CGCTGCCGGC | CCCGGCGTAA | GGACCCCCGG |
| 401 | GGGCGGTGCT | CCCGCCCGCC | TCGATAAAAG | GCTCCGGGGC | CGGCGGCGGC |
| | CCCGCCACGA | GGGCGGGCGG | AGCTATTTTC | CGAGGCCCCG | GCCGCCGCCG |
| 451 | CCACGAGCTA | CCCGGAGGAG | CGGGAGGCGT | CTCTGCCAGC | GGCCCGACGC |
| | GGTGCTCGAT | GGGCCTCCTC | GCCCTCCGCA | GAGACGGTCG | CCGGGCTGCG |
| 501 | GCAGTCAGCA | CAGGTAGGTG | GGCACCGCGC | CGTGCCGTGC | CGTGCCGTGC |
| | CGTCAGTCGT | GTCCATCCAC | CCGTGGCGCG | GCACGGCACG | GCACGGCACG |
| 551 | CGCCCGGCGC | CCCTTCGCGG | GGCCGTCGTG | TGGGCCCTCC | GTGGGCCCCG |
| | GCGGGCCGCG | GGGAAGCGCC | CCGGCAGCAC | ACCCGGGAGG | CACCCGGGGC |
| 601 | CCGTCACCCT | GAGCCTCACG | GCCCCGTGCC | CCGCAGACAG | CCAGCACCAT |
| | GGCAGTGGGA | CTCGGAGTGC | CGGGGCACGG | GGCGTCTGTC | GGTCGTGGTA |
| 651 | GGGAAAAATC | AGCAGTCTTC | CAACCCAATT | ATTTAAGTGC | TGCTTTTGTG |
| | CCCTTTTTAG | TCGTCAGAAG | GTTGGGTTAA | TAAATTCACG | ACGAAAACAC |
| 701 | ATTTCTTGAA | GGTGAAGATG | CACACCATGT | CCTCCTCGCA | TCTCTTCTAC |
| | TAAAGAACTT | CCACTTCTAC | GTGTGGTACA | GGAGGAGCGT | AGAGAAGATG |
| 751 | CTGGCGCTGT | GCCTGCTCAC | CTTCACCAGC | TCTGCCACGG | CTGGACCGGA |
| | GACCGCGACA | CGGACGAGTG | GAAGTGGTCG | AGACGGTGCC | GACCTGGCCT |
| 801 | GACGCTCTGC | GGGGCTGAGC | TGGTGGATGC | TCTTCAGTTC | GTGTGTGGAG |
| | CTGCGAGACG | CCCCGACTCG | ACCACCTACG | AGAAGTCAAG | CACACACCTC |

Fig.17

| | | | | | |
|---|---|---|---|---|---|
| 851 | ACAGGGGCTT TGTCCCCGAA | TTATTTCAAC AATAAAGTTG | AAGCCCACAG TTCGGGTGTC | GGTATGGCTC CCATACCGAG | CAGCAGTCGG GTCGTCAGCC |
| 901 | AGGGCGCCTC TCCCGCGGAG | AGACAGGCAT TCTGTCCGTA | CGTGGATGAG GCACCTACTC | TGCTGCTTCC ACGACGAAGG | GGAGCTGTGA CCTCGACACT |
| 951 | TCTAAGGAGG AGATTCCTCC | CTGGAGATGT GACCTCTACA | ATTGCGCACC TAACGCGTGG | CCTCAAGCCT GGAGTTCGGA | GCCAAGTCAG CGGTTCAGTC |
| 1001 | CTCGCTCTGT GAGCGAGACA | CCGTGCCCAG GGCACGGGTC | CGCCACACCG GCGGTGTGGC | ACATGCCCAA TGTACGGGTT | GACCCAGAAG CTGGGTCTTC |
| 1051 | GAAGTACATT CTTCATGTAA | TGAAGAACGC ACTTCTTGCG | AAGTAGAGGG TTCATCTCCC | AGTGCAGGAA TCACGTCCTT | ACAAGAACTA TGTTCTTGAT |
| 1101 | CAGGATGTAG GTCCTACATC | GAAGACCCTC CTTCTGGGAG | CTGAGGAGTG GACTCCTCAC | AAGAGTGACA TTCTCACTGT | TGCCACCGCA ACGGTGGCGT |
| 1151 | GGATCCCCCG CCTAGGGGGC | GGCTGCAGGA CCGACGTCCT | ATTCGATGGC TAAGCTACCG | CCATCCATTG GGTAGGTAAC | TCCACCGTAA AGGTGGCATT |
| 1201 | ATGCTTCTAA TACGAAGATT | ACATGTTTAC TGTACAAATG | ATGATCACTT TACTAGTGAA | TGCCAACCAC ACGGTTGGTG | ACTCAGGATG TGAGTCCTAC |
| 1251 | ACAATCTTGT TGTTAGAACA | AGGTTCCAGG TCCAAGGTCC | CTGCTGAGGA GACGACTCCT | CCTGCACCAG GGACGTGGTC | CCATGCAACT GGTACGTTGA |
| 1301 | TTCTATTTTG AAGATAAAAC | TAACAATTTC ATTGTTAAAG | TGGTTACTGT ACCAATGACA | TGCTGCAAAG ACGACGTTTC | CTCCATGTGA GAGGTACACT |
| 1351 | CACAGTGTAT GTGTCACATA | GTAAAGTGTA CATTTCACAT | CATAAATTAA GTATTTAATT | TTTATTTTAC AAATAAAATG | CTCGTTTTGT GAGCAAAACA |
| 1401 | TTGTTTTTAA AACAAAAATT | AACCAATGCC TTGGTTACGG | CTGTGGAAGG GACACCTTCC | AAACATAAAA TTTGTATTTT | CTTCAAGAAG GAAGTTCTTC |
| 1451 | CATTAAATCA GTAATTTAGT | TCAGTCATTC AGTCAGTAAG | TGTCACACCC ACAGTGTGGG | CTAATGCAGT GATTACGTCA | TGTTTCTGTC ACAAAGACAG |
| 1501 | ATCATTTCCC TAGTAAAGGG | TGGGCTCTTC ACCCGAGAAG | CATCTCTCGC GTAGAGAGCG | TGACCTGGGA ACTGGACCCT | CTGGGTGCTG GACCCACGAC |
| 1551 | GGGCTGGGAG CCCGACCCTC | CAGGGGTTGG GTCCCCAACC | GGCTCTCCAG CCGAGAGGTC | GGAGAGATGG CCTCTCTACC | CATGGGGAGA GTACCCTCT |
| 1601 | GTGATGGGAT CACTACCCTA | ACTGCTGGGG TGACGACCCC | GGGGGGGACT CCCCCCCTGA | CACCCTGCTG GTGGGACGAC | TGGGCTGCAG ACCCGACGTC |
| 1651 | GAAGCCCATT CTTCGGGTAA | GGTGCAGAGA CCACGTCTCT | GCAGCCTGGG CGTCGGACCC | ATGCCCATGA TACGGGTACT | CACGGGCACC GTGCCCGTGG |

Fig.17A

| | | | | | |
|---|---|---|---|---|---|
| 1701 | CACTGCACCG | TGTTTCTCCC | ATGCCCAGTA | GGGAAAGGGT | TACGAGCGCC |
| | GTGACGTGGC | ACAAAGAGGG | TACGGGTCAT | CCCTTTCCCA | ATGCTCGCGG |
| 1751 | GTTCATTCTC | AGCTTGTGAA | GGATTTTGTT | GGGCTCAGCC | TGCCAGAGCA |
| | CAAGTAAGAG | TCGAACACTT | CCTAAAACAA | CCCGAGTCGG | ACGGTCTCGT |
| 1801 | GTAGCCAGGC | ATGCCTGTGC | AGCTCCGAGC | TGTGATGGAC | AGAGGCAAGG |
| | CATCGGTCCG | TACGGACACG | TCGAGGCTCG | ACACTACCTG | TCTCCGTTCC |
| 1851 | CTGCAGCTGA | GGCCAGGTGG | TGGGCACAGG | TTAAATTAAG | AGCTTTCCAC |
| | GACGTCGACT | CCGGTCCACC | ACCCGTGTCC | AATTTAATTC | TCGAAAGGTG |
| 1901 | TCCACTTATG | GAAAGCCCTC | CTGCACTCAC | CCTGTCCCTG | GGGCTGGGGG |
| | AGGTGAATAC | CTTTCGGGAG | GACGTGAGTG | GGACAGGGAC | CCCGACCCCC |
| 1951 | CAGCCAGGGC | CACTTCCTCA | CCCCACCTGA | CACACAAGGC | TTTGCCTGCA |
| | GTCGGTCCCG | GTGAAGGAGT | GGGGTGGACT | GTGTGTTCCG | AAACGGACGT |
| 2001 | CAGCCAGGAC | CTCCTGTGGC | CACAGACTCT | TATAGATTCG | CTGTGCCCTA |
| | GTCGGTCCTG | GAGGACACCG | GTGTCTGAGA | ATATCTAAGC | GACACGGGAT |
| 2051 | GGAGACCAGG | GGGCTTTCCC | TGCCTGGCCT | TCTGGCCCCG | GCGACACTGC |
| | CCTCTGGTCC | CCCGAAAGGG | ACGGACCGGA | AGACCGGGGC | CGCTGTGACG |
| 2101 | AGGAGCTGCC | CTATCTGCCT | CCTCTTAGAT | GGTCCTGGCA | GGAAGGCTGC |
| | TCCTCGACGG | GATAGACGGA | GGAGAATCTA | CCAGGACCGT | CCTTCCGACG |
| 2151 | ACTTGGCTTG | GGGCTGATCC | ATATTACCAC | TGCAGTAGGG | ACAGCACTGC |
| | TGAACCGAAC | CCCGACTAGG | TATAATGGTG | ACGTCATCCC | TGTCGTGACG |
| 2201 | TGGAAGAAAA | GATGATTTTC | AACTGAACTT | ACTATCCAGG | CAGGTTATTG |
| | ACCTTCTTTT | CTACTAAAAG | TTGACTTGAA | TGATAGGTCC | GTCCAATAAC |
| 2251 | CTTTATTGTG | ATGGTGCTAA | GAGTGCGTTC | TTTCTCACTG | TAATGATTTT |
| | GAAATAACAC | TACCACGATT | CTCACGCAAG | AAAGAGTGAC | ATTACTAAAA |
| 2301 | GCCCTCATGT | GTGAATACAC | TTTCCAATAA | CAGCACAGCC | TCCAAAGGGA |
| | CGGGAGTACA | CACTTATGTG | AAAGGTTATT | GTCGTGTCGG | AGGTTTCCCT |
| 2351 | ATTTCTGCAG | GAAGAGACAG | TACCTGGTGT | GGGAAGTCCC | TGTGCAGCCC |
| | TAAAGACGTC | CTTCTCTGTC | ATGGACCACA | CCCTTCAGGG | ACACGTCGGG |
| 2401 | TATGTGCTTC | AAGCTGAATG | GCTGGGACTG | GCTGGGAGAG | CAGGATCACA |
| | ATACACGAAG | TTCGACTTAC | CGACCCTGAC | CGACCCTCTC | GTCCTAGTGT |
| 2451 | TCCTTTCTTA | AAAAGACAAA | CAGAAGGTAG | TGTGTGACCT | TGCTGTATTT |
| | AGGAAAGAAT | TTTTCTGTTT | GTCTTCCATC | ACACACTGGA | ACGACATAAA |
| 2501 | ACTATTTACG | CGTTGTTGTT | CAGTGGCACA | TACCTCAACG | GGGATATGGA |
| | TGATAAATGC | GCAACAACAA | GTCACCGTGT | ATGGAGTTGC | CCCTATACCT |

Fig.17B

| | | | | | |
|---|---|---|---|---|---|
| 2551 | GAGCTATTTC | CCCAACCCTC | GCTGCTGGAC | CCTGATCTGG | GGTTTTCCTG |
| | CTCGATAAAG | GGGTTGGGAG | CGACGACCTG | GGACTAGACC | CCAAAAGGAC |
| 2601 | TAGCTTAAGC | GGTGCCAACT | GCTTAAGTGA | TTGTAGAATC | AGTAAGGCTG |
| | ATCGAATTCG | CCACGGTTGA | CGAATTCACT | AACATCTTAG | TCATTCCGAC |
| 2651 | GAAAAGACCA | CAGATCATTA | AGTCCAACTG | TCAGCCCCAT | CCCCACCGCG |
| | CTTTTCTGGT | GTCTAGTAAT | TCAGGTTGAC | AGTCGGGGTA | GGGGTGGCGC |
| 2701 | CCCACTGTCA | CTCAGTGCCA | CATCCACGCA | TTTCTTGAAC | ATCTCCAGGG |
| | GGGTGACAGT | GAGTCACGGT | GTAGGTGCGT | AAAGAACTTG | TAGAGGTCCC |
| 2751 | ACAGTGACTC | CACCCGTCAC | CAGCTGTGCT | TCAGAGCAGG | CAGGGTGACA |
| | TGTCACTGAG | GTGGGCAGTG | GTCGACACGA | AGTCTCGTCC | GTCCCACTGT |
| 2801 | GTCTCAGTGC | CAGTTGCATC | CTGCTGAAGA | GCTTAACAGT | GCAGTTTAAC |
| | CAGAGTCACG | GTCAACGTAG | GACGACTTCT | CGAATTGTCA | CGTCAAATTG |
| 2851 | AACGGACTGA | TTTGTTGATG | TGGTTGCTGA | ATCAGTACGT | TGAGATGTCA |
| | TTGCCTGACT | AAACAACTAC | ACCAACGACT | TAGTCATGCA | ACTCTACAGT |
| 2901 | CTAAACTTTT | TGGAGATTAA | TTTCAGGATG | GAACACATTC | TTAACCCTGA |
| | GATTTGAAAA | ACCTCTAATT | AAAGTCCTAC | CTTGTGTAAG | AATTGGGACT |
| 2951 | AACCAGCCTT | TGATTTGGGC | TTGGCATTTG | CAGAATTTGC | AGGAAAAGAT |
| | TTGGTCGGAA | ACTAAACCCG | AACCGTAAAC | GTCTTAAACG | TCCTTTTCTA |
| 3001 | TGTTTGGGAA | CAGATGAATG | GAATTTCCAC | CAAACAGAAA | ATTAACACTT |
| | ACAAACCCTT | GTCTACTTAC | CTTAAAGGTG | GTTTGTCTTT | TAATTGTGAA |
| 3051 | ACACCAGTTT | GAGTCTGGTC | TTCGTTGGAT | ATTTCTTAAG | AATCTCATCA |
| | TGTGGTCAAA | CTCAGACCAG | AAGCAACCTA | TAAAGAATTC | TTAGAGTAGT |
| 3101 | TCCTCCCTGC | TCTTGGACCA | GTGCTGCTGA | CAGGAGGTGG | AGGATCATCA |
| | AGGAGGGACG | AGAACCTGGT | CACGACGACT | GTCCTCCACC | TCCTAGTAGT |
| 3151 | GGGTCAGCAT | CCTCAGCATC | TAGGGATGTG | CACTATGTGT | GATGGTGACA |
| | CCCAGTCGTA | GGAGTCGTAG | ATCCCTACAC | GTGATACACA | CTACCACTGT |
| 3201 | CTTTAGAGAA | CTGCTTTGAT | TCCCCAGGGC | TTTCCCTCTC | TTCCATGCAG |
| | GAAATCTCTT | GACGAAACTA | AGGGGTCCCG | AAAGGGAGAG | AAGGTACGTC |
| 3251 | GGCTCACTAT | CAGCCCTGAA | AGTCCAACTT | TCTGAACTTC | CAGCACCGTC |
| | CCGAGTGATA | GTCGGGACTT | TCAGGTTGAA | AGACTTGAAG | GTCGTGGCAG |
| 3301 | TGCTCCTGGT | AGGCTGTTCC | ATAGAGGCCA | CAGGGACTGT | AGCCAGGCAT |
| | ACGAGGACCA | TCCGACAAGG | TATCTCCGGT | GTCCCTGACA | TCGGTCCGTA |
| 3351 | GACCTTTTCC | CAGCCGTGCT | CTGAATCCAG | CACTGGTGGC | TGGGAGGCAG |
| | CTGGAAAAGG | GTCGGCACGA | GACTTAGGTC | GTGACCACCG | ACCCTCCGTC |

Fig.17C

| | | | | | |
|---|---|---|---|---|---|
| 3401 | CTCTGGTCCT<br>GAGACCAGGA | GGGGTGCTGC<br>CCCCACGACG | AGTGAGCCAG<br>TCACTCGGTC | GGAACAAGCT<br>CCTTGTTCGA | TATCGATACC<br>ATAGCTATGG |
| 3451 | GTCGACCTCG<br>CAGCTGGAGC | AGGGGGGGCC<br>TCCCCCCCGG | CGGTACCCAG<br>GCCATGGGTC | CTTTTGTTCC<br>GAAAACAAGG | CTTTAGTGAG<br>GAAATCACTC |
| 3501 | GGTTAATTTC<br>CCAATTAAAG | GAGCTTGGCG<br>CTCGAACCGC | TAATCATGGT<br>ATTAGTACCA | CATAGCTGTT<br>GTATCGACAA | TCCTGTGTGA<br>AGGACACACT |
| 3551 | AATTGTTATC<br>TTAACAATAG | CGCTCACAAT<br>GCGAGTGTTA | TCCACACAAC<br>AGGTGTGTTG | ATACGAGCCG<br>TATGCTCGGC | GAAGCATAAA<br>CTTCGTATTT |
| 3601 | GTGTAAAGCC<br>CACATTTCGG | TGGGGTGCCT<br>ACCCCACGGA | AATGAGTGAG<br>TTACTCACTC | CTAACTCACA<br>GATTGAGTGT | TTAATTGCGT<br>AATTAACGCA |
| 3651 | TGCGCTCACT<br>ACGCGAGTGA | GCCCGCTTTC<br>CGGGCGAAAG | CAGTCGGGAA<br>GTCAGCCCTT | ACCTGTCGTG<br>TGGACAGCAC | CCAGCTGCAT<br>GGTCGACGTA |
| 3701 | TAATGAATCG<br>ATTACTTAGC | GCCAACGCGC<br>CGGTTGCGCG | GGGGAGAGGC<br>CCCCTCTCCG | GGTTTGCGTA<br>CCAAACGCAT | TTGGGCGCTC<br>AACCCGCGAG |
| 3751 | TTCCGCTTCC<br>AAGGCGAAGG | TCGCTCACTG<br>AGCGAGTGAC | ACTCGCTGCG<br>TGAGCGACGC | CTCGGTCGTT<br>GAGCCAGCAA | CGGCTGCGGC<br>GCCGACGCCG |
| 3801 | GAGCGGTATC<br>CTCGCCATAG | AGCTCACTCA<br>TCGAGTGAGT | AAGGCGGTAA<br>TTCCGCCATT | TACGGTTATC<br>ATGCCAATAG | CACAGAATCA<br>GTGTCTTAGT |
| 3851 | GGGGATAACG<br>CCCCTATTGC | CAGGAAAGAA<br>GTCCTTTCTT | CATGTGAGCA<br>GTACACTCGT | AAAGGCCAGC<br>TTTCCGGTCG | AAAAGGCCAG<br>TTTTCCGGTC |
| 3901 | GAACCGTAAA<br>CTTGGCATTT | AAGGCCGCGT<br>TTCCGGCGCA | TGCTGGCGTT<br>ACGACCGCAA | TTTCCATAGG<br>AAAGGTATCC | CTCCGCCCCC<br>GAGGCGGGGG |
| 3951 | CTGACGAGCA<br>GACTGCTCGT | TCACAAAAAT<br>AGTGTTTTTA | CGACGCTCAA<br>GCTGCGAGTT | GTCAGAGGTG<br>CAGTCTCCAC | GCGAAACCCG<br>CGCTTTGGGC |
| 4001 | ACAGGACTAT<br>TGTCCTGATA | AAAGATACCA<br>TTTCTATGGT | GGCGTTTCCC<br>CCGCAAAGGG | CCTGGAAGCT<br>GGACCTTCGA | CCCTCGTGCG<br>GGGAGCACGC |
| 4051 | CTCTCCTGTT<br>GAGAGGACAA | CCGACCCTGC<br>GGCTGGGACG | CGCTTACCGG<br>GCGAATGGCC | ATACCTGTCC<br>TATGGACAGG | GCCTTTCTCC<br>CGGAAAGAGG |
| 4101 | CTTCGGGAAG<br>GAAGCCCTTC | CGTGGCGCTT<br>GCACCGCGAA | TCTCATAGCT<br>AGAGTATCGA | CACGCTGTAG<br>GTGCGACATC | GTATCTCAGT<br>CATAGAGTCA |
| 4151 | TCGGTGTAGG<br>AGCCACATCC | TCGTTCGCTC<br>AGCAAGCGAG | CAAGCTGGGC<br>GTTCGACCCG | TGTGTGCACG<br>ACACACGTGC | AACCCCCCGT<br>TTGGGGGGCA |
| 4201 | TCAGCCCGAC<br>AGTCGGGCTG | CGCTGCGCCT<br>GCGACGCGGA | TATCCGGTAA<br>ATAGGCCATT | CTATCGTCTT<br>GATAGCAGAA | GAGTCCAACC<br>CTCAGGTTGG |

Fig.17D

| | | | | | |
|---|---|---|---|---|---|
| 4251 | CGGTAAGACA<br>GCCATTCTGT | CGACTTATCG<br>GCTGAATAGC | CCACTGGCAG<br>GGTGACCGTC | CAGCCACTGG<br>GTCGGTGACC | TAACAGGATT<br>ATTGTCCTAA |
| 4301 | AGCAGAGCGA<br>TCGTCTCGCT | GGTATGTAGG<br>CCATACATCC | CGGTGCTACA<br>GCCACGATGT | GAGTTCTTGA<br>CTCAAGAACT | AGTGGTGGCC<br>TCACCACCGG |
| 4351 | TAACTACGGC<br>ATTGATGCCG | TACACTAGAA<br>ATGTGATCTT | GGACAGTATT<br>CCTGTCATAA | TGGTATCTGC<br>ACCATAGACG | GCTCTGCTGA<br>CGAGACGACT |
| 4401 | AGCCAGTTAC<br>TCGGTCAATG | CTTCGGAAAA<br>GAAGCCTTTT | AGAGTTGGTA<br>TCTCAACCAT | GCTCTTGATC<br>CGAGAACTAG | CGGCAAACAA<br>GCCGTTTGTT |
| 4451 | ACCACCGCTG<br>TGGTGGCGAC | GTAGCGGTGG<br>CATCGCCACC | TTTTTTTGTT<br>AAAAAAACAA | TGCAAGCAGC<br>ACGTTCGTCG | AGATTACGCG<br>TCTAATGCGC |
| 4501 | CAGAAAAAAA<br>GTCTTTTTTT | GGATCTCAAG<br>CCTAGAGTTC | AAGATCCTTT<br>TTCTAGGAAA | GATCTTTTCT<br>CTAGAAAAGA | ACGGGGTCTG<br>TGCCCCAGAC |
| 4551 | ACGCTCAGAA<br>TGCGAGTCTT | GAACTCGTCA<br>CTTGAGCAGT | AGAAGGCGAT<br>TCTTCCGCTA | AGAAGGCGAT<br>TCTTCCGCTA | GCGCTGCGAA<br>CGCGACGCTT |
| 4601 | TCGGGAGCGG<br>AGCCCTCGCC | CGATACCGTA<br>GCTATGGCAT | AAGCACGAGG<br>TTCGTGCTCC | AAGCGGTCAG<br>TTCGCCAGTC | CCCATTCGCC<br>GGGTAAGCGG |
| 4651 | GCCAAGCTCT<br>CGGTTCGAGA | TCAGCAATAT<br>AGTCGTTATA | CACGGGTAGC<br>GTGCCCATCG | CAACGCTATG<br>GTTGCGATAC | TCCTGATAGC<br>AGGACTATCG |
| 4701 | GGTCCGCCAC<br>CCAGGCGGTG | ACCCAGCCGG<br>TGGGTCGGCC | CCACAGTCGA<br>GGTGTCAGCT | TGAATCCAGA<br>ACTTAGGTCT | AAAGCGGCCA<br>TTTCGCCGGT |
| 4751 | TTTTCCACCA<br>AAAAGGTGGT | TGATATTCGG<br>ACTATAAGCC | CAAGCAGGCA<br>GTTCGTCCGT | TCGCCATGGG<br>AGCGGTACCC | TCACGACGAG<br>AGTGCTGCTC |
| 4801 | ATCCTCGCCG<br>TAGGAGCGGC | TCGGGCATGC<br>AGCCCGTACG | GCGCCTTGAG<br>CGCGGAACTC | CCTGGCGAAC<br>GGACCGCTTG | AGTTCGGCTG<br>TCAAGCCGAC |
| 4851 | GCGCGAGCCC<br>CGCGCTCGGG | CTGATGCTCT<br>GACTACGAGA | TCGTCCAGAT<br>AGCAGGTCTA | CATCCTGATC<br>GTAGGACTAG | GACAAGACCG<br>CTGTTCTGGC |
| 4901 | GCTTCCATCC<br>CGAAGGTAGG | GAGTACGTGC<br>CTCATGCACG | TCGCTCGATG<br>AGCGAGCTAC | CGATGTTTCG<br>GCTACAAAGC | CTTGGTGGTC<br>GAACCACCAG |
| 4951 | GAATGGGCAG<br>CTTACCCGTC | GTAGCCGGAT<br>CATCGGCCTA | CAAGCGTATG<br>GTTCGCATAC | CAGCCGCCGC<br>GTCGGCGGCG | ATTGCATCAG<br>TAACGTAGTC |
| 5001 | CCATGATGGA<br>GGTACTACCT | TACTTTCTCG<br>ATGAAAGAGC | GCAGGAGCAA<br>CGTCCTCGTT | GGTGAGATGA<br>CCACTCTACT | CAGGAGATCC<br>GTCCTCTAGG |
| 5051 | TGCCCCGGCA<br>ACGGGGCCGT | CTTCGCCCAA<br>GAAGCGGGTT | TAGCAGCCAG<br>ATCGTCGGTC | TCCCTTCCCG<br>AGGGAAGGGC | CTTCAGTGAC<br>GAAGTCACTG |

Fig.17E

| | | | | | |
|---|---|---|---|---|---|
| 5101 | AACGTCGAGC TTGCAGCTCG | ACAGCTGCGC TGTCGACGCG | AAGGAACGCC TTCCTTGCGG | CGTCGTGGCC GCAGCACCGG | AGCCACGATA TCGGTGCTAT |
| 5151 | GCCGCGCTGC CGGCGCGACG | CTCGTCCTGC GAGCAGGACG | AGTTCATTCA TCAAGTAAGT | GGGCACCGGA CCCGTGGCCT | CAGGTCGGTC GTCCAGCCAG |
| 5201 | TTGACAAAAA AACTGTTTTT | GAACCGGGCG CTTGGCCCGC | CCCCTGCGCT GGGGACGCGA | GACAGCCGGA CTGTCGGCCT | ACACGGCGGC TGTGCCGCCG |
| 5251 | ATCAGAGCAG TAGTCTCGTC | CCGATTGTCT GGCTAACAGA | GTTGTGCCCA CAACACGGGT | GTCATAGCCG CAGTATCGGC | AATAGCCTCT TTATCGGAGA |
| 5301 | CCACCCAAGC GGTGGGTTCG | GGCCGGAGAA CCGGCCTCTT | CCTGCGTGCA GGACGCACGT | ATCCATCTTG TAGGTAGAAC | TTCAATCATG AAGTTAGTAC |
| 5351 | CGAAACGATC GCTTTGCTAG | CTCATCCTGT GAGTAGGACA | CTCTTGATCA GAGAACTAGT | GATCTTGATC CTAGAACTAG | CCCTGCGCCA GGGACGCGGT |
| 5401 | TCAGATCCTT AGTCTAGGAA | GGCGGCAAGA CCGCCGTTCT | AAGCCATCCA TTCGGTAGGT | GTTTACTTTG CAAATGAAAC | CAGGGCTTCC GTCCCGAAGG |
| 5451 | CAACCTTACC GTTGGAATGG | AGAGGGCGCC TCTCCCGCGG | CCAGCTGGCA GGTCGACCGT | ATTCCGGTTC TAAGGCCAAG | GCTTGCTGTC CGAACGACAG |
| 5501 | CATAAAACCG GTATTTTGGC | CCCAGTCTAG GGGTCAGATC | CAACTGTTGG GTTGACAACC | GAAGGGCGAT CTTCCCGCTA | CGGTGCGGGC GCCACGCCCG |
| 5551 | CTCTTCGCTA GAGAAGCGAT | TTACGCCAGC AATGCGGTCG | TGGCGAAAGG ACCGCTTTCC | GGGATGTGCT CCCTACACGA | GCAAGGCGAT CGTTCCGCTA |
| 5601 | TAAGTTGGGT ATTCAACCCA | AACGCCAGGG TTGCGGTCCC | TTTTCCCAGT AAAAGGGTCA | CACGACGTTG GTGCTGCAAC | TAAAACGACG ATTTTGCTGC |
| 5651 | GCCAGTGAAT CGGTCACTTA | TGTAATACGA ACATTATGCT | CTCACTATAG GAGTGATATC | GGCGAATTGG CCGCTTAACC | AGCTCCACCG TCGAGGTGGC |
| 5701 | CGGTGGC GCCACCG | | | | |

Fig.17F

EXPRESSION VECTOR SYSTEMS AND METHOD OF USE

RELATED APPLICATION

This application is a continuation-in-part of Schwartz et al., U.S. patent application Ser. No. 08/209,846, filed Mar. 9, 1994, U.S. Pat. No. 5,756,264, entitled "Expression Vector Systems and Method of Use," the whole of which is incorporated by reference, including drawings. The 08/209,846 is a continuation-in-part of Schwartz et al., U.S. patent application Ser. No. 07/789,919, filed Nov. 6, 1991, U.S. Pat. No. 5,298,422, entitled "Myogenic Vector Systems", the whole of which (including drawings) is hereby incorporated by reference.

The invention was partially supported by a grant from the United States Government under HL-38401 awarded by the National Institute of Health. The U.S. Government may have rights in the invention.

BACKGROUND OF THE INVENTION

This invention relates to vectors which encode stable messenger RNA (mRNA) and methods of using such vectors. In particular, this invention relates to vectors which establish controlled expression of recombinant genes within a tissue at levels which are useful for gene therapy and other applications.

The regulation of gene expression can be related to the rate of metabolic breakdown of mRNA molecules. Chen et al., *J. Bact.*, vol. 172, no. 8, pp. 4578–4586 (1990). Such decay rates of individual mRNA species effects steady state expression levels of the corresponding protein in the cytoplasm. Id. Thus, the rate at which a particular protein is made is directly proportional to the cytoplasmic level of the mRNA which encodes it.

Studies have measured the stabilities of different mRNAs. Regulatory polypeptide mRNAs such as transcription factors or cytokines are often highly unstable whereas mRNAs for housekeeping proteins or maternal mRNAs which must be stored until after oocyte fertilization tend to be stable. Braverman, G., Cell Vol. 88, pp. 5–6 (1987); Rosenthal, E. T., et al., J.M.B. Vol. 166, pp. 307–327 (1983). Studies have also shown skeletal muscle mRNA to be distributed into two populations with regard to stability. Medford et al., *J. Biol. Chem.*, vol. 258, pp. 11063–11073 (1983). One mRNA population has a half life of less than four hours and the other population has a half life of seventeen to over fifty-four hours. Id.

Researchers have examined factors which enhance or degrade mRNA stability. For example, the presence of 5' 7-methylguanosine triphosphate cap structures as well as the 3' poly (A) tails have been analyzed as mRNA stabilizers against degradation. Berstein, P., et al., Trends Biochem. Sci. Vol. 14, pp. 373–377 (1989); Drummond, D. R. et al., Nucleic Acid Res. Vol. 13 pp. 7375–7394 (1985); Sachs, A., Curr. Op. Cell Biol., Vol. 2, pp. 1092–1098 (1990). Studies suggest that the poly (A) tail and the poly (A)-binding protein (pABP) interact in order to regulate mRNA stability. Berstein, P., et al., Mol. Cell. Biol. Vol. 9, pp. 659–670 (1989). Such studies show increased mRNA stability when poly (A) tails are present. Deadenylation of the poly (A) tail, however, does not necessarily result in destabilization. Berstein, P., et al., Trends Biochem. Sci., Vol. 14, pp. 373–377 (1989).

Elements specific to mRNAs have been identified which can either stabilize or destabilize the transcript. These mRNA elements are thought to interact with cytoplasmic transacting factors. Studies show the transferrin receptor mRNA appears to be stabilized when an ironresponsive element in the 3' untranslated region (3'UTR) of the mRNA is bound by a specific 90 kDa binding protein. Mullner, E. W., et al., Cell Vol. 58, pp. 373–382 (1989); Casey, J., et al., EMBO J, Vol. 8, pp. 3693–3699 (1989). Other stability determining cis-acting sequences are located in the 5' untranslated region (5'UTR) or the coding region of an mRNA. Jones, T. R., et al., Mol. Cell. Biol. Vol. 7, pp. 4513–4521 (1987); Shyu, A., et al., Genes Dev., Vol. 3, pp. 60–72 (1989); Wisdom, R., et al., P.N.A.S., Vol. 86, pp. 3574–3578 (1989).

Studies have also shown that 3' UTRs containing AU-rich sequences correlate with rapid mRNA degradation by causing destabilization of the RNA transcript. Caput, et al., *P.N.A.S.*, vol. 83, pp. 1670–1674 (1986); Cleveland, et al., *New. Biol.*, vol. 1, pp. 121–126 (1989). Transcripts from many transiently expressed eukaryotic genes, including lymphokine genes and protooncogenes (c-myc and c-fos) contain AU-rich sequences in their 3' UTRs and are rapidly degraded in the cytoplasm. Schuler, et al., *Cell*, vol. 55, pp. 1115–1122 (1988); Shaw, et al., *Genes & Dev.*, vol. 3, pp. 60–72 (1989). These studies have shown that deletion of AU-rich sequences from the c-fos or c-myc 3'UTR confers stability upon transcripts produced from transfected constructs. Wilson, et al., *Nature*, vol. 336, pp. 396–399 (1988); Jones, et al., *Mol. Cell. Biol.*, vol. 7, pp. 4513–4521 (1987).

In addition, studies have shown that introduction of a AU-rich sequence from the granulocyte-macrophage colony-stimulating factor (GM-CSF) 3'UTR into the 3'UTR of the rabbit β-globin gene confers instability upon the otherwise stable β-globin mRNA. Shaw, et al., *Cell*, vol. 46, pp. 659667 (1986). AU-rich sequences have also been detected in the 3'UTR of interleukin-2, tumor necrosis factor-α and Human B Cell Stimulatory Factor II. Bohjanen, *Mol. Cell. Biol.*, vol. 11, no. 6, pp. 3228–3295 (1991); Tonouchi, et al., *Bio. Biopph. Res. Com.*, vol. 163, no. 2, pp. 1056–1062 (1989).

Studies have also compared the sequence of UTRs in vertebrate skeletal-α, cardiac-α and β-actin mRNA. These studies revealed regions of high sequence homology within the 3'UTR portion of each of these actin isoformic mRNA. This homology is greater among the a-cardiac and skeletal actin isoforms than between the α-skeletal actin and gactin isoform mRNAs. Mayer, et al., *Nucl. Acids Res.*, vol. 12, pp. 1087–1100 (1984); Ponte et al., *Nucl. Acids Res.*, vol. 12, pp. 1687–1696 (1984); Chang et al., *Nucl. Acids Res.*, vol. 13, pp. 1223–1237 (1985). In comparison, 3'UTR sequences of other vertebrate genes, such as those encoding insulin and prolactin, share common coding regions but usually contain divergent 3'UTRs. Mayer et al., supra, Ponte et al., supra.

SUMMARY OF THE INVENTION

The applicant has identified RNA stability elements located in the 3' UTRs and/or 3' non-coding regions (3' NCR) of eukaryotic genes. Applicant has determined that it is useful to construct vectors based upon these particular 3' UTRs and/or 3' NCRs. Specifically, these regions increase the expression of nucleic acid sequences contained within vectors by stabilizing the RNA transcripts and enhancing the transcriptional and translational processes.

In addition, expression of these vectors can be tissue specific. These vectors are useful in facilitating enhanced expression in tissues as well as useful in targeting expression with tissue specificity. These vectors can be used to treat diseases by gene therapy by targeting the vectors to tissues where the vector is expressed. Vectors containing such sequences are able to provide controlled expression of recombinant genes within tissues at certain levels that are useful for gene therapy and other applications. These vectors can also be used to create transgenic animals for research or livestock improvement.

Stability of mRNA relates to the rate of metabolic breakdown or decay of an mRNA molecule within a cell. The stability correlates directly with the rate of expression of a given gene, i.e., synthesis of the corresponding protein. Decay rates of mRNA affects the steady state expression levels of a gene. We have determined that 3'UTR sequences as defined below provide mRNA stability. By using 3'UTR sequences with the vectors of the present invention, the decay rates of mRNAs encoded by the vectors are reduced, i.e., increased mRNA stability. The increased stability causes increased expression.

Taking advantage of the unique mRNA stability provided during expression of the vectors as well as the tissue specificity, the present invention features use of a vector to enhance expression of any specific nucleic acid sequence in tissue. In particular, the present invention demonstrates that by utilizing certain 3'UTR and 3'NCR sequences, expression is enhanced due to specific stability of mRNA. Such stability helps in the transcription and translation processes of mmRNA. The increased mRNA stability in cells caused by the 3'UTR and 3'NCR provides a higher level of mRNA accumulation. This increased mRNA stability leads to increased levels of protein production. In addition, the expression vectors may be constructed to provide expression of exogenous DNA with tissue specificity. Furthermore, the expression vectors can be constructed so as to regulate, through other factors, the expression of the exogenous DNA.

This unique ability of the expression vector to provide enhanced mRNA stability as well as direct expression to specific tissues allows the vector to be used for treating numerous diseases. The above vectors can be used in gene therapy where a vector encoding a therapeutic product is introduced into a tissue so that tissue will express the therapeutic product. For example, the above vectors may be used for treating muscle atrophy associated with neurological, muscular, or systemic disease or aging by causing tissues to express certain trophic factors. The above vectors may be used for treating hemophilias by causing tissues to express certain clotting factors and secrete these factors into the circulation. Furthermore, the vectors above can be used for preventing or treating atherogenesis and atherosclerotic cardiovascular, cerebrovascular, or peripheral-vascular disease by causing tissue to express certain factors involved in lipid metabolism.

In addition, the vectors above can be used for gene replacement of inherited genetic defects or acquired hormone deficiencies such as diabetes, for vaccination in humans or animals to induce immune responses, or for creating transgenic animals. The transgenic animals can be used as models for studying human diseases, for assessing and exploring novel therapeutic methods, to assess the effects of chemical and physical carcinogens, and to study the effect of various genes and genetic regulatory elements. Furthermore, transgenic animals can be used to develop commercially important livestock species. The above vectors can also be used to transform cells to produce particular proteins and RNA in vitro.

In a first aspect, the present invention features a vector for expression of a nucleic acid sequence in tissue by encoding stable mRNA. The vector includes a 5' flanking region which includes necessary sequences for the expression of a nucleic acid cassette, a 3' flanking region encoding a region, including a 3'UTR and/or a 3' NCR, which stabilizes mRNA expressed from the nucleic acid cassette, and a linker which connects the 5' flanking region to a nucleic acid. The linker does not contain the coding sequence of a gene that the linker is naturally associated with. That is, the linker is not the normal gene associated with the 5' and 3' regions. The 3' flanking region is 3' to the position for inserting the nucleic acid cassette.

Stability of mRNA as discussed above and as used herein refers to the rate of metabolic breakdown or decay of an mRNA molecule within a cell. The faster the turnover, i.e., breakdown, of mRNA the less stable the mRNA is within a cell. In contrast, the slower the turnover of a mRNA the more stable the mRNA is within a cell. Such stability correlates directly with the rate of expression of a given gene, i.e., synthesis of the corresponding protein. These decay rates of individual mRNA species directly effects the steady state expression levels of a gene in the cytoplasm, i.e., increased stability causes increase in expression.

The 3' flanking region containing sequences for regions such as the 3'UTR and/or 3'NCR, as defined below, provide mRNA stability in a number of ways. These include but are not limited to providing a particular mRNA structure which protects the mRNA from degradation within the cytoplasm. This includes mRNA secondary structures as well as sequences and/or factors which recognize an appropriate trans acting regulatory factors or respond to regulatory system, i.e., mRNA stability regulated by hormones and other physiological effectors. This does not include mRNA stability due to a poly (A) sequence. Poly (A) sequences are not encoded by the DNA themselves but are added to the mRNA once transcription has occurred due to signals from the sequences transcribed into the mRNA.

The stability of mRNA can be determined by various methods such as measuring mRNA half-life. The half life is the elapsed time during which half of the mRNA in a cell is eliminated. The mRNA half life is longer if the nucleic acid cassette encodes a 3'UTR and/or 3'NCR sequence than when it does not. Half-life measurements can be performed by pulse chase methods using [$^3$H] uridine as described below, or by other methods known in the art. In addition to half life, other methods known in the art can also be used to measure mRNA stability. Hentze, M. W., Biochimica et Biophysica Acta, Vol. 1090, pp. 281–292 (1991).

The term "flanking region" as used herein refers to nucleotide sequences on either side of an associated gene. Flanking regions can be either 3' or 5' to a particular gene in question. In general, flanking sequences contain elements necessary for regulation of expression of a particular gene. Such elements include, but are not limited to, sequences necessary for efficient expression, as well as tissue specific expression. Examples of sequences necessary for efficient expression can include specific regulatory sequences or elements adjacent to or within the protein coding regions of DNA. These elements, located adjacent to the gene, are termed cis-acting elements. The signals are recognized by other diffusible biomolecules in trans to alter the transcriptional activity. These biomolecules are termed trans-acting factors.

Trans-acting factors and cis-acting elements have been shown to contribute to the timing and developmental expression pattern of a gene. Cis-acting elements are usually thought of as those that regulate transcription and are usually found within promoter regions and within upstream (5') or downstream (3') DNA flanking regions.

Flanking DNA with regulatory elements that regulate expression of genes in tissue may also include modulatory or regulatory sequences which are regulated by specific factors, such as glucocorticoids, androgens, vitamin $D_3$ and its metabolites, vitamin A and its metabolites, retinoic acid, calcium as well as others. "Modulatory" or "regulatory" sequences as used herein refer to sequences which may be in the 3' or 5' flanking region, where such sequences can enhance activation and/or suppression of the transcription of the associated gene. "Responsive" or "respond" as used herein refers to the enhancement of activation and/or suppression of gene transcription as discussed below. "Metabolite" as used herein refers to any product from the metabolism of the regulatory factors which regulate gene expression.

In addition to the above, the flanking regions, whether 3' or 5', can cause tissue specificity. Such tissue specificity provides expression predominantly in a specified cell or tissue. "Predominantly" as used herein means that the gene associated with the 3' or 5' flanking region is expressed to a higher degree only in the specific tissue as compared to low expression or lack of expression in nonspecific tissue. The 3' or 5' flanking regions singularly or together as used herein can provide expression of the associated gene in other tissues but to a lower degree than expression in tissues or cells where expression is predominate. Expression is preferentially in the specified tissue. Such predominant expression can be compared with the same magnitude of difference as will be found in the natural expression of the gene (i.e. as found in a cell in vivo) in that particular tissue or cell type as compared with other nonspecific tissues or cells. Such differences can be observed by analysis of mRNA levels or expression of natural gene products, recombinant gene products, or reporter genes. Furthermore, northern analysis, X gal immunofluorescence or CAT assays as discussed herein and as known in the art can be used to detect such differences.

The 3' flanking region contains sequences or regions, e.g. 3'UTR and/or 3' NCR, which regulate expression of a nucleic acid sequence with which it is associated. The 3' flanking regions can provide tissue-specific expression to an associated gene. The 3' flanking region also contains a transcriptional termination signal. The term 3' flanking region as used herein includes that portion of a naturally occurring sequence 3' to the transcribed portion of the gene which are responsible for mRNA processing and/or tissue-specific expression. That portion can be readily defined by known procedures. For example, the portions of a 3' flanking region which are responsible for mRNA stability and/or tissue-specific expression can be mapped by mutational analysis or various clones created to define the desired 3' flanking region activity in a selected vector system.

The 3' flanking region can contain a 3'UTR and/or a 3' NCR. The term "3' untranslated region" or "3'UTR" refers to the sequence at the 3' end of structural gene which is transcribed from the DNA but not translated into protein. In addition, the actual nucleotides that promote the 3' stabilizing effects may extend within the coding region of the gene. This 3'UTR region does not contain a poly(A) sequence. Poly (A) sequences are only added after the transcriptional process.

Myogenic-specific 3'UTR sequences can be used to allow for specific stability in muscle cells or other tissues. As described below, myogenic-specific sequences refers to gene sequences normally expressed in muscle cells, e.g., skeletal, heart and smooth muscle cells. Myogenic specific mRNA stability provides an increase in mRNA stability within myogenic cells. The increase in stability provides increased expression. The 3'UTR and 3' NCR sequences singularly or together can provide a higher level of mRNA accumulation through increased mRNA stability. Thus, increased expression and/or stability of mRNA leads to increased levels of protein production.

The term "3' non-coding region" or "3'NCR" is a region which is adjacent to the 3'UTR region of a structural gene. The 3'NCR region generally contains a transcription termination signal. Once transcription occurs and prior to translation, the RNA sequence encoded by the 3'NCR is usually removed so that the poly (A) sequence can be added to the mRNA. The 3'NCR sequences can also be used to allow mRNA stability as described above. The 3'NCR may also increase the transcription rate of the nucleic acid cassette.

The 3'UTR and 3' NCR sequences can be selected from a group of myogenic-specific genes. Examples of myogenic-specific genes include the skeletal u-actin gene, fast myosin-light chain 1/3 gene, myosin-heavy chain gene, troponin T gene, acetylcholine receptor subunit genes and muscle creatinine kinase gene.

The 5' flanking region is located 5' to the associated gene or nucleic acid sequence to be expressed. Just as with the 3' flanking region, the 5' flanking region can be defined by known procedures. For example, the active portion of the 5' flanking region can be mapped by mutational analysis or various clones of the 5' flanking region created to define the desired activity in a selected vector. The 5' flanking region can include, in addition to the above regulatory sequences or elements, a promoter, a TATA box, and a CAP site, which are in an appropriate relationship sequentially and positionally for the expression of an associated gene. In this invention, "necessary sequences" are those elements of the 5' flanking region which are sequentially and positionally in an appropriate relationship to cause controlled expression of a gene within a nucleic acid cassette. Expression is controlled to certain levels within tissues such that the expressed gene is useful for gene therapy and other applications. The 5' sequence can contain elements which regulate tissue-specific expression or can include portions of a naturally occurring 5' element responsible for tissue-specific expression.

The term "promoter," as used herein refers to a recognition site on a strand of DNA to which RNA polymerase binds. The promoter usually is a DNA fragment of about 100 to about 200 base pairs (in eukaryotic genes) in the 5' flanking DNA upstream of the CAP site or the transcriptional initiation start site. The promoter forms an "initiation complex" with RNA polymerase to initiate and drive transcriptional activity. The complex can be modified by activating sequences termed "enhancers" or inhibitory sequences termed "silencers". The promoter can be one which is naturally (i.e., associated as if it were within a cell in vivo) or non-naturally associated with a SI flanking region.

A variety of promoters can be used in the vectors of the present invention. Some examples include thymidine kinase promoter, myogenic-specific promoters including skeletal α-actin gene promoter, fast myosin light chain 1 promoter, myosin heavy chain promoter, troponin T promoter, and muscle creatinine kinase promoter, as well as non-specific promoters including the cytomegalovirus immediate early promoter, Rous Sarcoma virus LTR. These promoters or other promoters used with the present invention can be mutated in order to increase expression of the associated gene. Mutation as used herein refers to a change in the sequence of genetic material from normal causing a change in the functional characteristics of the gene. This includes gene mutations where only a single base is changed in the natural gene promoter sequences or multiple bases are changed. Furthermore a promoter may be used by itself or in combination with elements from other promoters, as well as various enhancers, transcript stabilizers, or other sequences capable of enhancing function of the vector.

The term "intron" as used herein refers to a section of DNA occurring in a transcribed portion of a gene which is included in a precursor RNA but is then excised during processing of the transcribed RNA before translation occurs. Intron sequences are therefore not found in mRNA nor translated into protein. The term "exon" as used herein refers to a portion of a gene that is included in a transcript of a gene and survives processing of the RNA in the cell to become part of a mRNA. Exons generally encode three distinct functional regions of the RNA transcript. The first, located at the 5' end which is not translated into protein, termed the 5' untranslated region (5' UTR), signals the beginning of RNA transcription and contains sequences that direct the mRNA to the ribosomes and cause the mRNA to be bound by ribosomes so that protein synthesis can occur. The second contain the information that can be translated into the amino acid sequence of the protein or function as a bioactive RNA molecule. The third, located at the 3' end is not translated into protein, i.e. 3' UTR, contains the signals for termination of translation and for the addition of a polyadenylation tail (poly(A). In particular, the 3' UTR as defined above can provide mRNA stability. The intron/exon boundary will be that portion in a particular gene where an intron section connects to an exon section. The terms "TATA box" and "CAP site" are used as they are recognized in the art.

The term "linker" as used herein refers to DNA which contains the recognition site for a specific restriction endonuclease. Linkers may be ligated to the ends of DNA fragments prepared by cleavage with some other enzyme. In particular, the linker provides a recognition site for inserting the nucleic acid cassette which contains a specific nucleic sequence to be expressed. This recognition site may be but is not limited to an endonuclease site in the linker, such as Cla-I, Not-I, Xmal, Bgl-II, Pac-I, Xhol, Nhel, Sfi-I. A linker can be designed so that the unique restriction endonuclease site contains a start codon (e.g. AUG) or stop codon (e.g. TAA, TGA, TCA) and these critical codons are reconstituted when a sequence encoding a protein is ligated into the linker. Such linkers commonly include an NcoI or SphI site.

The term "leader" as used herein refers to a DNA sequence at the 5' end of a structural gene which is transcribed and translated along with the gene. The leader usually results in the protein having an n-terminal peptide extension sometimes called a pro-sequence. For proteins destined for either secretion to the extracellular medium or the membrane, this signal sequence directs the protein into endoplasmic reticulum from which it is discharged to the appropriate destination. The leader sequence normally is encoded by the desired nucleic acid, synthetically derived or isolated from a different gene sequence. A variety of leader sequences from different proteins can be used in the vectors of the present invention. Some non-limiting examples include gelsolin, albumin, fibrinogen and other secreted serum proteins.

The term "vector" as used herein refers to a nucleic acid, e.g., DNA derived from a plasmid, cosmid, phasmid or bacteriophage or synthesized by chemical or enzymatic means, into which one or more fragments of nucleic acid may be inserted or cloned which encode for particular genes. The vector can contain one or more unique restriction sites for this purpose, and may be capable of autonomous replication in a defined host or organism such that the cloned sequence is reproduced. The vector may have a linear, circular, or supercoiled configuration and may be complexed with other vectors or other materials for certain purposes. The components of a vector can contain but is not limited to a DNA molecule incorporating: (1) DNA; (2) a sequence encoding a therapeutic or desired product; and (3) regulatory elements for transcription, translation, RNA stability and replication. A viral vector in this sense is one that contains a portion of a viral genome, e.g., a packaging signal, and is commonly useful not merely as DNA but as a gene located within a viral particle.

The purpose of the vector is to provide expression of a nucleic acid sequence in tissue. In the present invention this expression is enhanced by providing stability to an mRNA transcript from the nucleic acid sequence. Expression includes the efficient transcription of an inserted gene or nucleic acid sequence within the vector. Expression products may be proteins including but not limited to pure protein (polypeptide), glycoprotein, lipoprotein, phosphoprotein, or nucleoprotein. Expression products may also be RNA. The nucleic acid sequence is contained in a nucleic acid cassette. Expression of the nucleic acid can be continuous or controlled by endogenous or exogenous stimuli.

The term "control" or "controlled" as used herein relates to the expression of gene products (protein or RNA) at sufficiently high levels such that a therapeutic effect is obtained. Levels that are sufficient for therapeutic effect are lower than the toxic levels. Levels of expression for therapeutic effect within selected tissues corresponds to reproducible kinetics of uptake, elimination from cell, post-translational processing, and levels of gene expression, and, in certain instances, regulated expression in response to certain endogenous or exogenous stimuli (e.g., hormones, drugs).

The term "nucleic acid cassette" as used herein refers to the genetic material of interest which codes for a protein or RNA. The nucleic acid cassette is positionally and sequentially oriented within the vector such that the nucleic acid in the cassette can be transcribed into RNA, and when necessary, translated into a protein in the transformed tissue or cell. Preferably, the cassette has 3' and SI ends adapted for ready insertion into a vector, e.g., it has restriction endonuclease sites at each end.

A variety of proteins can be encoded by the sequence in a nucleic acid cassette in the transformed tissue or cell. Those proteins which can be expressed may be located in the cytoplasm, nucleus, membranes (including the plasmalemma, nuclear membrane, endoplasmic reticulum or other internal membrane compartments), in organelles (including the mitochondria, peroxisome, lysosome, endosome or other organelles), or secreted. Those proteins may function as intracellular or extracellular structural elements, ligand, hormones, neurotransmitter, growth regulating factors, differentiation factors, gene-expression regulating factors, DNA-associated proteins, enzymes, serum proteins, receptors, carriers for small molecular weight organic or inorganic compounds, drugs, immunomodulators, oncogenes, tumor suppressor, toxins, tumor antigens, or antigens. These proteins may have a natural sequence or a mutated sequence to enhance, inhibit, regulate, or eliminate their biological activity.

Specific examples of these compounds include proinsulin, insulin, growth hormone, growth hormone release factor, androgen receptors, insulin-like growth factor I, insulin-like growth factor II, insulin-like growth factor binding protein, erythropoietin, clotting factors (VII, VIII, IX, others), chorionic gonadotropin, prolactin, endorphin, enkephalins, epidermal growth factor, TGF-α, TGF-β, nerve growth factors, dermal growth factor (PDGF), angiogenesis factors (e.g., acidic fibroblast growth factor, basic fibroblast growth factor and angiogenin), antiangiogenesis factors (interferon-α, interferon-β, interferon-γ, thrombospondin), brain growth factors, ciliary growth factors, matrix proteins (e.g., type IV collagen, type VII collagen, laminin), oncogenes (e.g., ras, fos, myc, erb, src, sis, jun), E6 or E7 transforming sequence, p53 protein, dystrophin, cytokinereceptors, interleukins (IL-1, IL-2, IL-4, IL-6, IL-8, IL-10, IL-12), interleukin inhibitors, viral capsid protein, viral reverse transcriptase, HIV-encoded protein, and antigens from eukaryotic, viral, bacterial, fungal, yeast, and parasitic organisms which can be used to induce an immunologic response.

In addition, the nucleic acid cassette can code for RNA. The RNA may function as a template for translation, as an antisense inhibitor of gene expression, as a triple-strand forming inhibitor of gene expression, as an enzyme (ribozyme) or as a ligand recognizing specific structural determinants on cellular structures for the purpose of modifying their activity. Specific examples include RNA molecules to inhibit the expression or function of prostaglandin synthase, lipooxenganse, histocompatibilty antigens (class I or class II), cell adhesion molecules, nitrous oxide synthase, $\beta_2$ microglobulin, oncogenes, and growth factors. These are only examples and are not meant to be limiting in any way.

The compounds which can be incorporated are only limited by the availability of the nucleic acid sequence for the protein or RNA to be incorporated. One skilled in the art will readily recognize that as more proteins or RNAs become identified they can be integrated into the vector system of the present invention and expressed in animal or human tissue.

The term "tissue" as used herein refers to a collection of cells specialized to perform a particular function or can include a single cell. The cells may be of the same type or of different types.

The term "gene", e.g., "myogenic genes," as used herein refers to those genes exemplified herein and their equivalence in other animal species or other tissues. Homologous sequences (i.e. sequences having a common evolutionary origin representing members of the same superfamily) or analogous sequences (i.e. sequences having common properties though a distinct evolutionary origin) are also included so long as they provide equivalent properties to those described herein. It is important in this invention that the chosen sequence provide the MRNA stability, enhanced levels of expression, expression of the appropriate product, and/or tissue-specific expression as noted herein. Those in the art will recognize that the minimum sequences required for such functions are encompassed by the above definition. These minimum sequences are readily determined by standard techniques exemplified herein.

The term "myogenic" refers to muscle tissue or cells. The muscle tissue or cells can be in vivo, in vitro, or in vitro tissue culture and capable of differentiating into muscle tissue. Myogenic cells include skeletal, heart and smooth muscle cells. Genes are termed "myogenic" or "myogenic-specific" if they are expressed or expressed preferentially in myogenic cells. Vectors are termed "myogenic" or "myogenic-specific" if they function preferentially in myogenic muscle tissue or cells. Myogenic activity of vectors can be determined by transfection of these vectors into myogenic cells in culture, injected into intact muscle tissue, or injected into mammalian oocytes to be stably incorporated into the genome to generate transgenic animals which express the protein or RNA of interest in myogenic cells.

The term "non-myogenic" refers to tissue or cells other than muscle. The tissues or cells can be in vivo, in vitro, or in vitro tissue culture.

In a preferred embodiment, the vector described above may have its 5' flanking region and/or its 3' flanking region from myogenic genes, in particular the skeletal α-actin gene. The 3'UTR of the chicken skeletal α-actin gene starts at nucleotide 2060 and extends to 2331 (Sequence I.D. No. 1), approximately 0.3 Kb. The complete 3' flanking region with a 3'UTR and contiguous 3' NCR of the gene extends an additional 2.0 Kb. This 2.3 Kb fragment can be linked immediately following the natural translation termination codon to a cDNA sequence coding for the protein or RNA to be expressed. As discussed above, these regions can be further and more precisely defined by routine methodology, e.g. deletion or mutation analysis or their equivalents. Preferably, the vector contains such a 3' region or 5' region comprising, consisting, or consisting essentially of the regions disclosed above. The terms "comprising," "consisting," or "consisting essentially of" as used herein (with respect to a vector with the 3' or 5' regions of the present invention) includes those regions as well as those regions above in which the sequence is changed but the desired vector activity remains equivalent. Such a change, for example, could be a change of ten nucleotides in any of the above regions. This is only an example and is nonlimiting.

In addition, another embodiment of the above vector may contain a regulatory system for regulating expression of the nucleic acid cassette. The term "regulatory system" as used herein refers to cis-acting or transacting sequences incorporated into the above vectors which regulate in some characteristic the expression of the nucleic acid of interest as well as trans-acting gene products which are co-expressed in the cell with the above described vector. Regulatory systems can be used for up-regulation or down regulation of expression from the normal levels of expression or existing levels of expression at the time of regulation. The system contributes to the timing and developmental expression pattern of the nucleic acid.

One construction of a regulatory system includes a chimeric trans-acting regulatory factor incorporating elements of a serum response factor capable of regulating expression of the vector in a cell. The chimeric trans-acting regulatory factor is constructed by replacing the normal DNA binding domain sequence of the serum response factor with a DNA binding domain sequence of a receptor. The serum response factor has a transactivation domain which is unchanged. The transactivation domain is capable of activating transcription when an agent or ligand specific to the receptor binding site binds to the receptor. Thus, regulation can be controlled by controlling the amount of the agent.

The DNA binding domain sequence of a receptor, incorporated into the chimeric trans-activating regulatory factor, can be selected from a variety of receptor groups including but not limited to vitamin, steroid, thyroid, orphan, hormone, retinoic acid, thyroxine, or GAL4 receptors. The chimeric trans-activating regulator factor is usually located within the sequence of the promoter. In one preferred embodiment the promoter used in the vector is the –actin promoter and the receptor is the vitamin D receptor.

Another embodiment of the regulatory system includes the construction of a vector with two functional units. One functional unit expresses a receptor. This functional unit contains elements required for expression including a promoter, a nucleic acid sequence coding for the receptor, and a 3' UTR and/or a 3' NCR. The second functional unit expresses a therapeutic protein or RNA and contains, in addition, a response element corresponding to the receptor, a promoter, a nucleic acid cassette, and a 3' UTR and/or a 3' NCR. These functional units can be in the same or separate vectors.

The first functional unit expresses the receptor. It is favorable to use a receptor not found in high levels in the target tissue. The receptor forms an interaction, e.g., ionic, nonionic, hydrophobic, with the response element on the second functional unit prior to, concurrent with, or after the binding of the agent or ligand to the receptor. This interaction allows the regulation of the nucleic acid cassette expression. The receptor can be from the same nonlimiting group as disclosed above. Furthermore, the vector can be myogenic specific by using myogenic specific 3' UTR and/or 3' NCR sequences.

A second aspect of the present invention features a specific plasmid with the above elements useful for expression of a nucleic acid sequence in tissue. The plasmid includes a nucleic acid cassette encoding for IGF-1, a portion or complete sequence of the skeletal α-actin promoter, other 5' flanking sequences, 3' flanking sequences such as 3' UTR and/or 3' NCR regions and nucleic acid sequences encoding for antibody resistance. In one embodiment the plasmid can be pIG0100A or pIG0335. These are only examples and meant to be non-limiting. Thus, changes or variations can be made to the 5' and 3'flanking regions.

A third related aspect of the invention features a transgenic animal whose cells contain the vectors of the present invention. These cells include germ or somatic cells. The transgenic animals can be used as models for studying human diseases, for assessing and exploring novel therapeutic methods, to assess the effects of chemical and physical carcinogens, and to study the effect of various genes and genetic regulatory elements. In addition, transgenic animals can be used to develop commercially important livestock species.

A fourth related aspect of the present invention features cells transformed with a vector of the present invention for expression of a nucleic acid sequence. As described above, the nucleic acid cassette may contain genetic material and code for a variety of proteins or RNA.

As used herein, "transformation" is the change in a cell's phenotypic characteristics by the action of a gene expressing a gene product. The gene causing the phenotypic characteristic change has been transfected into the cell. The term "transfection" as used herein refers to a mechanism of gene transfer which involves the uptake of DNA by a cell or organism. Following entry into the cell, the transforming DNA may recombine with that of the host by physically integrating into the chromosomes of the host cell, may be maintained transiently as an episomal element without being replicated, or may replicate independently as a plasmid. Transfection can be performed by in vivo techniques as described below, or by ex vivo techniques in which cells are co-transfected with a vector containing a selectable marker. This selectable marker is used to select those cells which have become transformed. It is well known to those skilled in the art the type of selectable markers to be used with transfection/transformation studies. Transfection/ transformation can be tissue-specific, i.e., involve the use of myogenic specific vectors which cause expression of the nucleic acid cassette predominantly in the tissue of choice. In particular, tissue specificity can be directed to myogenic cells by using 3'UTR and/or 3' NCR sequences specific for myogenic tissue expression.

The transformed cell can produce a variety of compounds selected from proteins or RNA described above in the discussion of nucleic acid cassettes. The product expressed by the transformed cell depends on the nucleic acid in the translated region of the nucleic acid cassette within the vector.

A fifth related aspect of the present invention features methods for transfecting a cell with the vectors of the present invention. These methods comprise the steps of contacting a cell in situ with a vector of the present invention for sufficient time to transfect the cell. As discussed above, transfection can be in vivo or ex vivo.

A sixth related aspect of the present invention features a method for treating disease by transfecting cells with the above-referenced vectors. Disease can include but is not limited to muscle atrophy, atherogenesis, atherosclerotic cardiovascular, cerebrovascular, or peripheral vascular disease, diabetes, neuropathy, growth disorders and hemophilia. These vectors contain nucleic acid sequences coding for proteins or RNA. The sequences can encode for insulin-like growth factor I, insulin-like growth factor II, insulin growth factor binding protein, growth hormone, growth hormone release hormone, androgen receptors, mutant androgen receptors or derivatives thereof, apolipoprotein A-I, lipoprotein lipase, or the VLDL-receptor, nerve growth factor, or brain derived neurotropic factors. These are only examples and are not meant to be limiting. "Receptor" as used herein includes natural receptors (i.e., as found in a cell in vivo) as well as anything that binds alike and causes compartmentalization changes in a cell.

The methods of treating disease of the present invention feature methods for establishing expression of protein or RNA in tissue by administration of a vector. These methods of use of the above-referenced vectors comprises the steps of administering an effective amount of the vectors to a human, animal or tissue culture. The term "administering" or "administration" as used herein refers to the route of introduction of a vector or carrier of DNA into the body. The vectors of the above methods and the methods discussed below may be administered by various routes. In particular a preferred target cell for treatment is the skeletal muscle cell. The term "skeletal muscle" as used herein refers to those cells which comprise the bulk of the body's musculature, i.e., striated muscle.

Administration can be directly to a target tissue or may involve targeted delivery after systemic administration. The preferred embodiments are by direct injection into muscle or targeted uptake into muscle after intravenous injection. The term "delivery" refers to the process by which the vector comes into contact with the preferred target cell after administration. Administration may involve needle injection into cells, tissues, fluid spaces, or blood vessels, electroporation, transfection, hypospray, iontophoresis, particle bombardment, or transplantation of cells genetically modified ex vivo. Examples of administration include intravenous, intramuscular, aerosol, oral, topical, systemic, ocular, intraperitoneal and/or intrathecal.

The preferred means for administration of vectors described above involves the use of formulations for delivery to the target cell in which the vector is associated with elements such as lipids, proteins, carbohydrates, synthetic organic compounds, or in-organic compounds which enhance the entry of the vector into the nucleus of the target cell where gene expression may occur. The term "formulation" as used herein refers to non-genetic material combined with the vector in a solution, suspension, or colloid which enhances the delivery of the vector to a tissue, uptake by cells within the tissue, intracellular trafficking through the membrane, endosome or cytoplasm into the nucleus, the stability of the vector in extracellular or intracellular compartments, and/or expression of genetic material by the cell. In a preferred embodiment of the present invention the vector and formulation comprises a nanoparticle which is administered as a suspension or colloid. The formulation can include lipids, proteins, carbohydrates, synthetic organic compounds, or inorganic compounds. Examples of elements which are included in a formulation are lipids capable of forming liposomes, cationic lipids, hydrophilic polymers, polycations (e.g. protamine, polybrine, spermidine, polylysine), peptide or synthetic ligand recognizing receptors on the surface of the target cells, peptide or synthetic ligand capable of inducing endosomal-lysis, peptide or synthetic ligand capable of targeting materials to the nucleus, gels, slow release matrices, salts, carbohydrates, nutrients, or soluble or insoluble particles as well as analogues or derivatives of such elements. This includes formulation elements enhancing the delivery, uptake, stability, and/or expression of genetic material into cells. This list is included for illustration only and is not intended to be limiting in any way.

Another embodiment of the present invention features the above vectors with coating elements that enhance expression as well as uptake by the cell. The term "coating" as used herein refers to elements, proteins or molecules used to associate with the vector in order to enhance cellular uptake. In particular, coating includes a DNA initiation complex and histones. The coating improves the stability of the vector, its entry into the nucleus, and the efficiency of transcription. The term "DNA initiation complex" as used herein refers to a complex containing a serum response factor, a transcription initiation factor and a transregulatory factor. The serum response factor is attached to or interacts with the serum response element within the promoter region of the vector. The transcription initiation factor and the transregulatory factor then interact with the serum response factor and the promoter, in particular the TATA box within the promoter, to form a stable DNA complex. The term "histone" as used herein refers to nuclear proteins which associate with and/or bind to DNA, e.g., a vector. The histones can bind specifically or non-specifically to the DNA.

The term "effective amount" as used herein refers to sufficient vector administered to humans, animals or into tissue culture to produce the adequate levels of protein or RNA. One skilled in the art recognizes that the adequate level of protein or RNA will depend on the use of the particular vector. These levels will be different depending on the type of administration and treatment or vaccination.

The methods for treating diseases as disclosed herein includes treatment with biological products (specifically proteins as defined above) in which the disease being treated requires the protein to circulate through the body from the general circulation. For example, disorders which might be treated by the present invention include chronic pain by expression of endorphin or enkephalins, anemia by expression of erythropoietin, hemophilia by expression of appropriate clotting factors (specifically factor IX for treatment of hemophilia B, factor VIII for treatment of hemophilia A), failure of lactation by expression of prolactin, osteoporosis by expression of IGF-I or its binding proteins, immune deficiencies by expression of cytokines, lymphokines or appropriate colony stimulating factors, or metastatic cancer by the expression of interferon β or thrombospondin. The selection of the appropriate protein to treat various diseases will be apparent to one skilled in the art.

In treating disease, the present invention provides a means for achieving: (1) sufficiently high levels of a particular protein to obtain a therapeutic effect; (2) controlled expression of product at levels which are sufficient for therapeutic effect and lower than the toxic levels; (3) controlled expression in certain tissues in order to obtain reproducible pharmacokinetics and levels of gene expression; and (4) delivery using clinically and pharmaceutically acceptable means of administration and formulation rather than transplantation of genetically engineered and selected cells.

In doing so, the present invention provides significant advances over the art. First, promoters from viral genomes and viral vectors which were used to obtain high level expression in tissue, were not able to provide controlled expression. Second, promoters from various tissue-specific genes which were used to obtain controlled expression in transgenic animals and animal models of gene therapy did not have a sufficiently high level of expression to obtain therapeutic effect. In addition, in treating diseases with the present invention, the ability to raise antibodies against protein products does not reflect the ability to achieve controlled expression of proteins within the therapeutic range.

A seventh related aspect of the present invention features a method of gene replacement for inherited genetic diseases of muscle. This method includes the transfection of muscle cells with the above-referenced vectors.

In a eighth aspect, the present invention features a method for inducing an immunogenic or immunological response by transfecting cells with the above referenced vectors. The nucleic acid cassette may contain nucleic acid sequences coding for proteins or other factors which might produce an immunogenic or immunological response. This would include formation of a vaccine. The nucleic acid cassette can contain genetic material that encodes for microbial proteins. This includes genetic material coding for a bacterial protein, a viral protein, a fungal protein, a yeast protein, or a parasitic protein. Examples of proteins which might be expressed include proteins from Human Immunodeficiency Virus, Cytomegalovirus, Respiratory Syncytial Virus, Influenza Virus, Hepatitis Virus (A,B,C,D), pneumococcus, meningococcus, streptococcus, staphylococcus, heat stable enterotoxin, heat labile enterotoxin, pneumocystitis, the pathogen of Lyme disease, aspergillus, candida, and malaria. This is only an example and is not meant to be limiting.

The genetic material which is incorporated into the cells from the above vectors can be any natural or synthetic nucleic acid. For example, the nucleic acid can be: (1) not normally found in the tissue of the cells; (2) normally found in a specific tissue but not expressed at physiological significant levels; (3) normally found in specific tissue and normally expressed at physiological desired levels; (4) any other nucleic acid which can be modified for expression in skeletal muscle cells; and (5) any combination of the above. In addition to the genetic material which is incorporated into tissue, the above reference is also applicable to genetic material which is incorporated into a cell.

Other features and advantages of the invention will be apparent from the following detailed description of the

BRIEF DESCRIPTION OF THE DRAWINGS

FIG. 12 is a schematic representation of a regulatable vector system using a Vitamin D receptor.

FIGS. 15 and 15A–15G is a nucleic acid sequence encoding the plasmid pIG0100A. (Seq ID NO:7)

FIGS. 17 and 17A–17F is the nucleic acid sequence encoding for the plasmid pIG0335 (SEQ ID NO:8).

The drawings are not necessarily to scale, and certain features of the invention may be exaggerated in scale and shown in schematic form in the interest of clarity and conciseness.

DETAILED DESCRIPTION OF THE INVENTION

The following are examples of the present invention using the regulatory elements of myogenic genes to construct vectors for specific nucleic acid expression in various tissues. These examples are offered by way of illustration and are not intended to limit the invention in any manner.

The following are specific examples of preferred embodiments of the present invention. These examples demonstrate how the expression vector systems of the present invention can be used in construction of various cellular or animal models, and how genes can be regulated by sequences within such vectors. The utility of such vectors is noted herein and is amplified upon in co-pending application by Schwartz et al., entitled "Myogenic Vector Systems," supra, and such sections (including drawings) are hereby specifically incorporated by reference herein.

Below are provided examples of specific regions of the 3'UTR and/or 3'NCR regions of myogenic genes that can be used to provide certain functionalities to an expression vector, and thus within a transformed cell or animal containing such a vector. Those in the art will recognize that specific portions of these regions can be identified as that containing the functional nucleic acid sequence providing the desirable property, and such regions can be readily defined using routine deletion or mutagenic techniques or their equivalent. Such regions include the promoter, enhancer, RNA stabilizing sequence, and cis- and transacting elements of a regulatable system. As noted herein, such controlling segments of nucleic acid may be inserted at any location on the vector, although there may be preferable sites as described herein.

Isolation of Chicken Skeletal α-Actin Gene

The nucleic acid sequence of the skeletal α-actin gene has been characterized in chicken, rat, mouse and human. Fornwald et al, supra, Zak et al, supra, French et al, supra, Huetal, supra, Minty et al, supra. The primary sequences of the skeletal α-actin gene were deduced from overlapping cDNA clones. To obtain full genes, the cDNA clones were used to screen genomic DNA.

Figure 1:
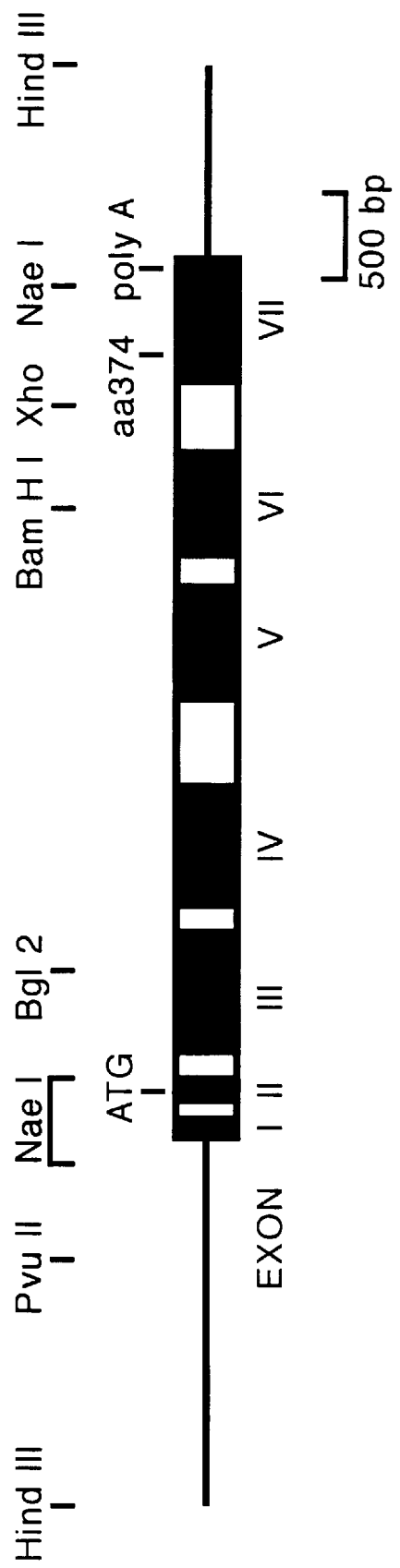
FIG. 1 is a schematic drawing of the chicken skeletal –actin gene which includes location of unique restriction sites.
Figure 2:
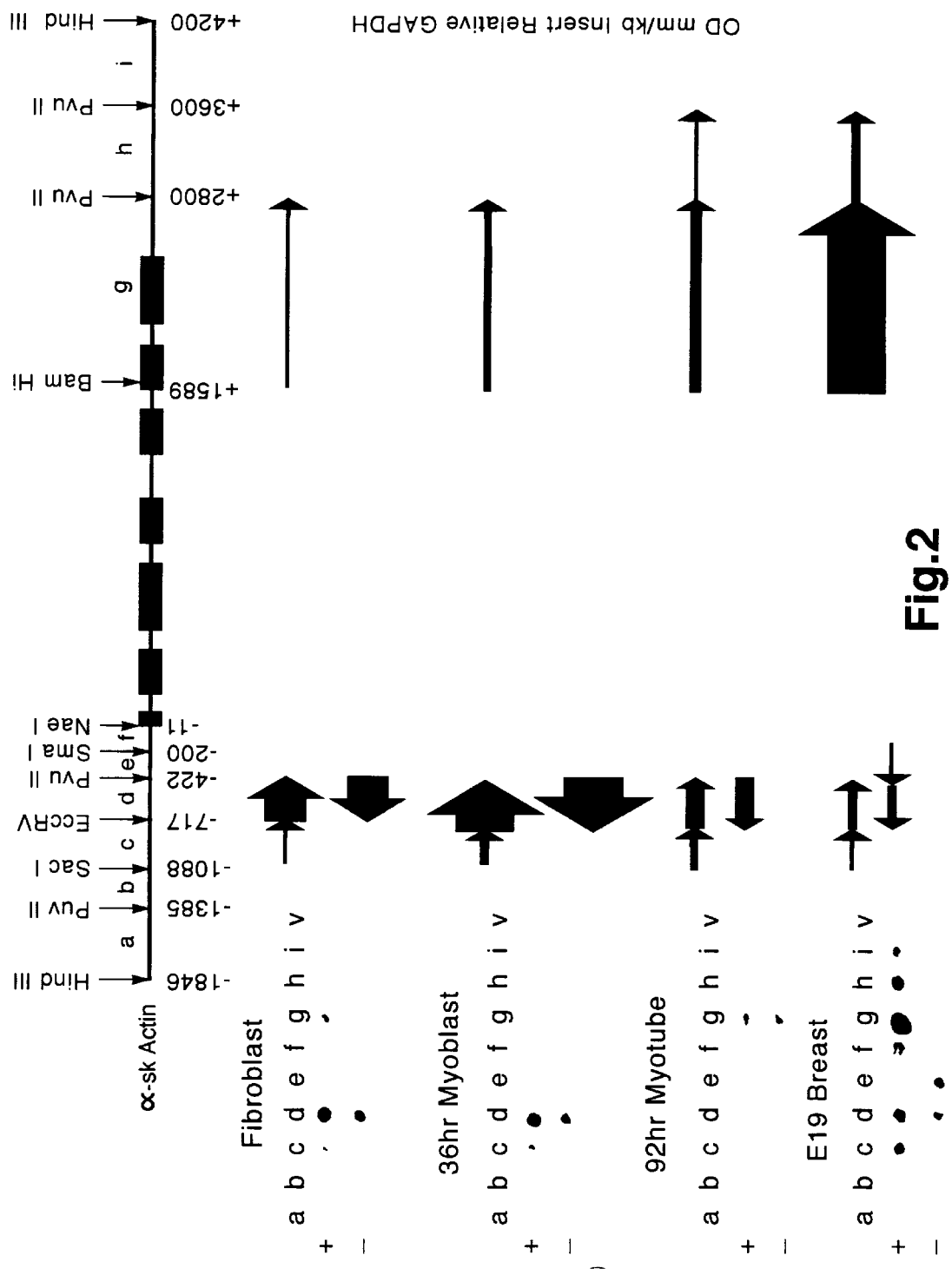
FIG. 2 illustrates the transcriptional domain of the avian skeletal α-actin gene and the contiguous noncoding region where transcription terminates.

For example, the 25 Kb EcoRI fragment of chicken genomic DNA isolated from a lambda Charon 4A vector, contains the 6.2 Kb skeletal α-actin gene on a single HindIII site of pBR322 is shown in FIG. 1. Chang et al. Mol. Cell. Biol. Vol 4:2498–2508 (1984). Nuclear transcription runoffs were used to map the transcriptional domain of the skeletal α-actin gene (FIG. 2). DNA probes which encompassed portions of the 5' noncoding, promoter coding, and the contiguous 3' noncoding regions were cloned into M13 vectors which provided sense and antisense probes. Nuclei isolated from fibroblasts, myoblasts and day 19 embryonic muscle cells were used in in vitro transcription assays to extend RNA transcripts with radioactive tagged nucleotides. Labeled RNA hybridized to dotted DNA probes showed that transcription terminates approximately 1 kb downstream of the skeletal α-actin gene's poly A addition site. This is within a 800 bp PvuII fragment between +2800 and +3600 nucleotides from the start of transcription.

Figure 3:
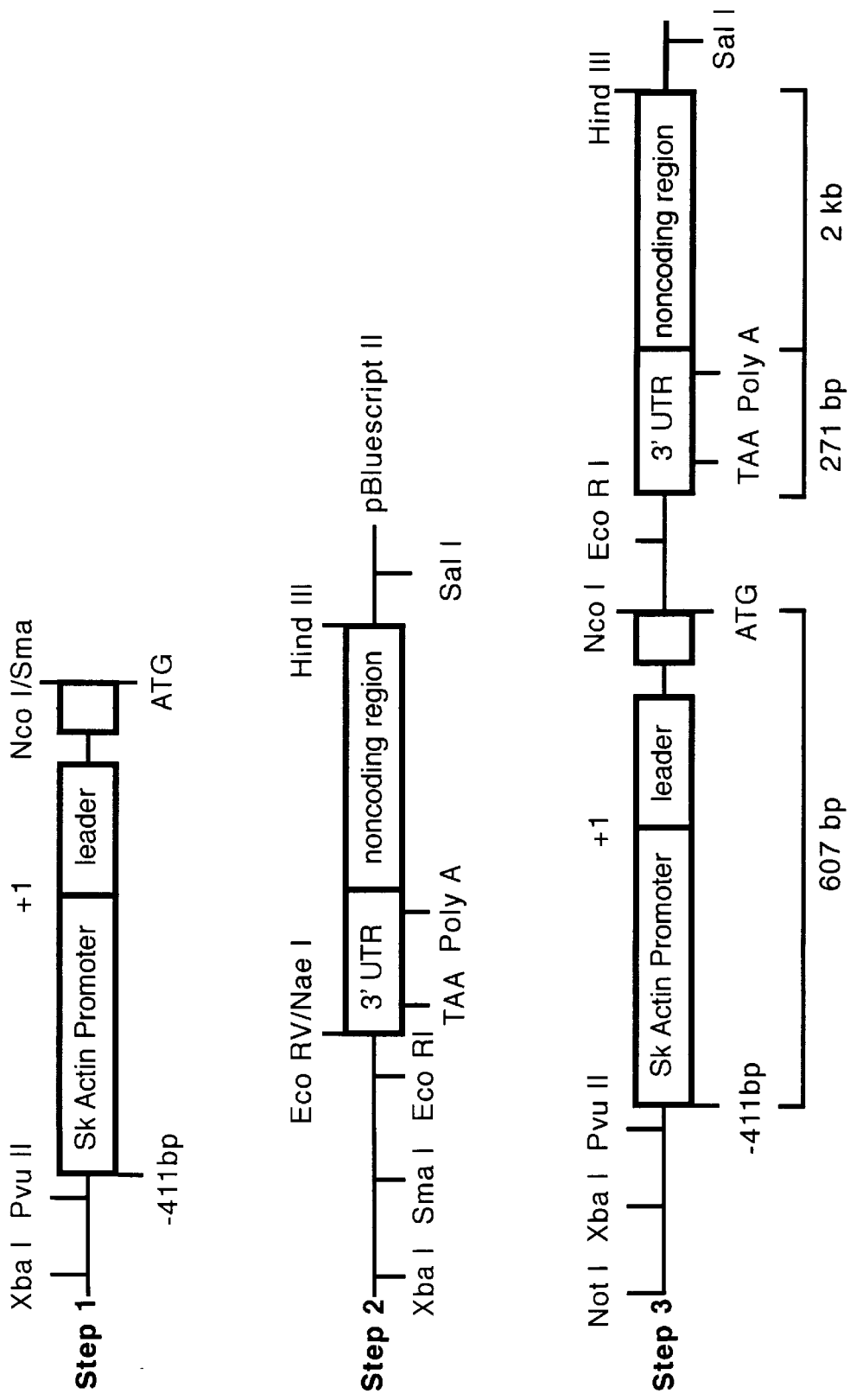
FIG. 3 is a schematic representation of a myogenic vector system.

The 3' UTR and/or 3' NCR can be isolated by restriction endonucleases digestion of the 6.2 Kb actin gene with blunt cutter NaeI, which cuts 30 bp upstream of the translation termination codon TAA. HindIII releases the 3' most portion of the actin gene from the vector pBR322 (FIG. 3). The 3'UTR and 3'NCR were used to prepare DNA constructs. The skeletal α-actin promoter and DNA flanking sequences (at least 411 nucleotides from the mRNA cap site) and DNA sequences extending through the skeletal 5' noncoding leader, first intron and up to the initiation of translation ATG, converted to a NcoI cloning site at +196, was liberated from a M13 double stranded DNA by XbaI and NcoI digestion, Klenow filled in and then linked into the XbaI and blunt SmaI sites of pBluescript II KS. The NcoI site is regenerated by this cloning step. The 3'UTR and 3'NCR on the 2.3 kb NaeI/HindIII fragment were directionally cloned into a blunt EcoRV site and the adjacent HindIII site of the pBluescript II KS vector cassette. The EcoRV and NaeI sites are destroyed. The restored NcoI site was used to insert cDNA sequences encoding polypeptides. Another cloning vector was constructed by inserting the skeletal α-actin promoter from −411 to −11 adjacent to the 3'UTR and 3'NCR. This expression vector eliminates the first intron and the skeletal actin 5' leader sequence. These two vectors were used in preparing DNA constructs to test the efficacy of the 3'UTR and 3' NCR.

Expression Vector Construction Containing Human IGF-I Gene

Figure 4:
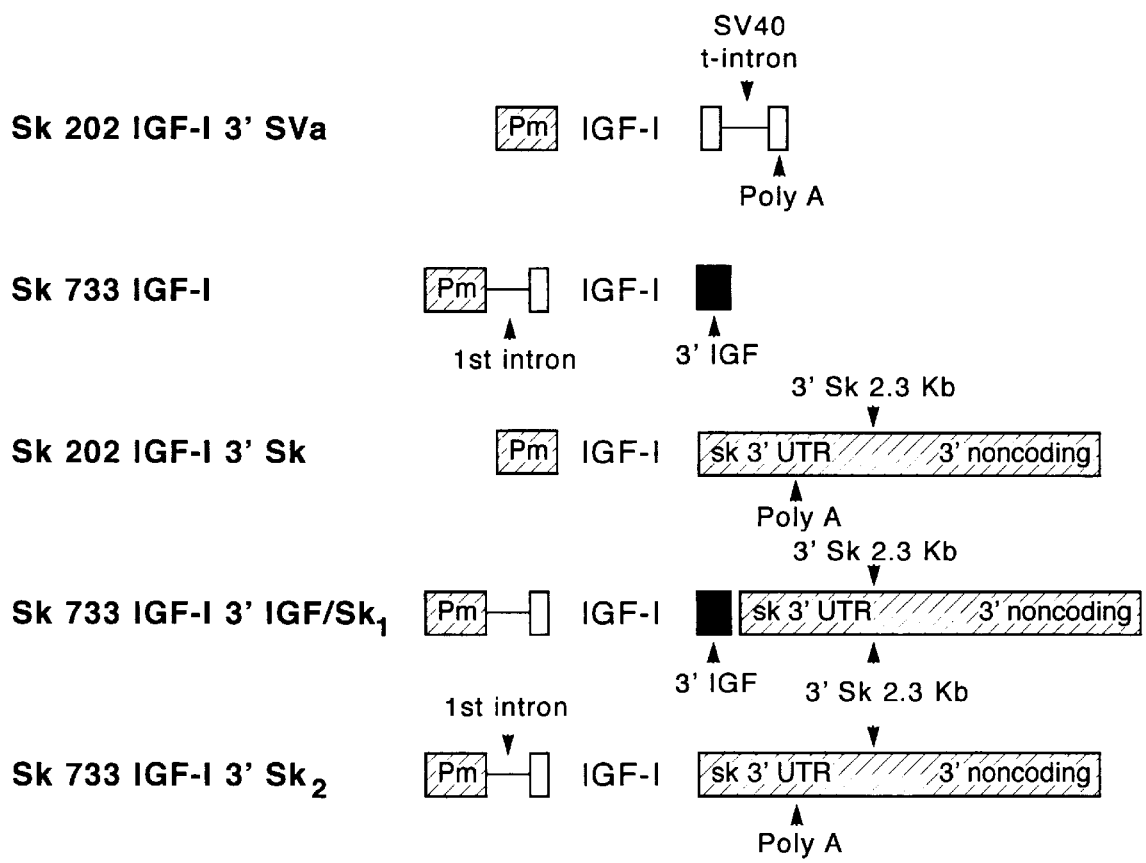
FIG. 4 is a schematic diagram of skeletal α-actin/insulin like growth factor-I hybrid genes

Constructions containing the skeletal α-actin promoter were linked to the human IGF-I cDNA (Seq. I.D. 6) by standard recombinant DNA techniques as known in the art. Examples of a generalized expression vector structure is shown in FIG. 3. Specific construction of an expression vector with IGF-I is shown in FIG. 4. The construction was made so that the SV40 poly A addition site and the small t-intron were linked to the 3'UTR of the IGF-I cDNA. The SV40 sequences were added to increase the stability of nuclear IGF-I RNA transcripts. Since the SV40 t-intron might not be entirely suitable in the expression of IGF-I in muscle cells, five other vectors were made. The SK733 NcoI vector contains approximately 411 nucleotides of the skeletal α-actin promoter, the natural cap site, 5' untranslated leader and the first intron. An NcoI site was engineered to create a unique insertion cloning site for the cassette containing the IGF-I cDNA, in which the initiation ATG was also converted to an NcoI site. The SK733IGF-I construction utilizes its own poly A site. An NaeI/HindIII fragment which incorporated the skeletal α-actin 3' UTR, poly A addition site, and terminating sequences was linked to SK202, SK733 NcoI, IGF-I and to SK733IGF-I which the IGF-I poly A site was deleted and replaced by that of skeletal α-actin. In this way IGF-I RNA transcripts containing the skeletal α-actin 3' UTR are stabilized and accumulate in skeletal muscle cells. In addition, by providing contiguous 3' NCR, IGF-I is buffered against outside genomic sequences and is thus more protected from position effects, when integrated into the genome. In addition, by providing natural terminating sequences, the additional regulatory sequences that mark the transcriptional domain of skeletal α-actin prevent read through transcription, improve tissue specificity, developmental timing and transcriptional activity. Presence of 3'NCR sequence allows for a single copy of the integrated vector to produce 40–500% of the transcriptional activity of the endogenous sequences.

Figure 14:
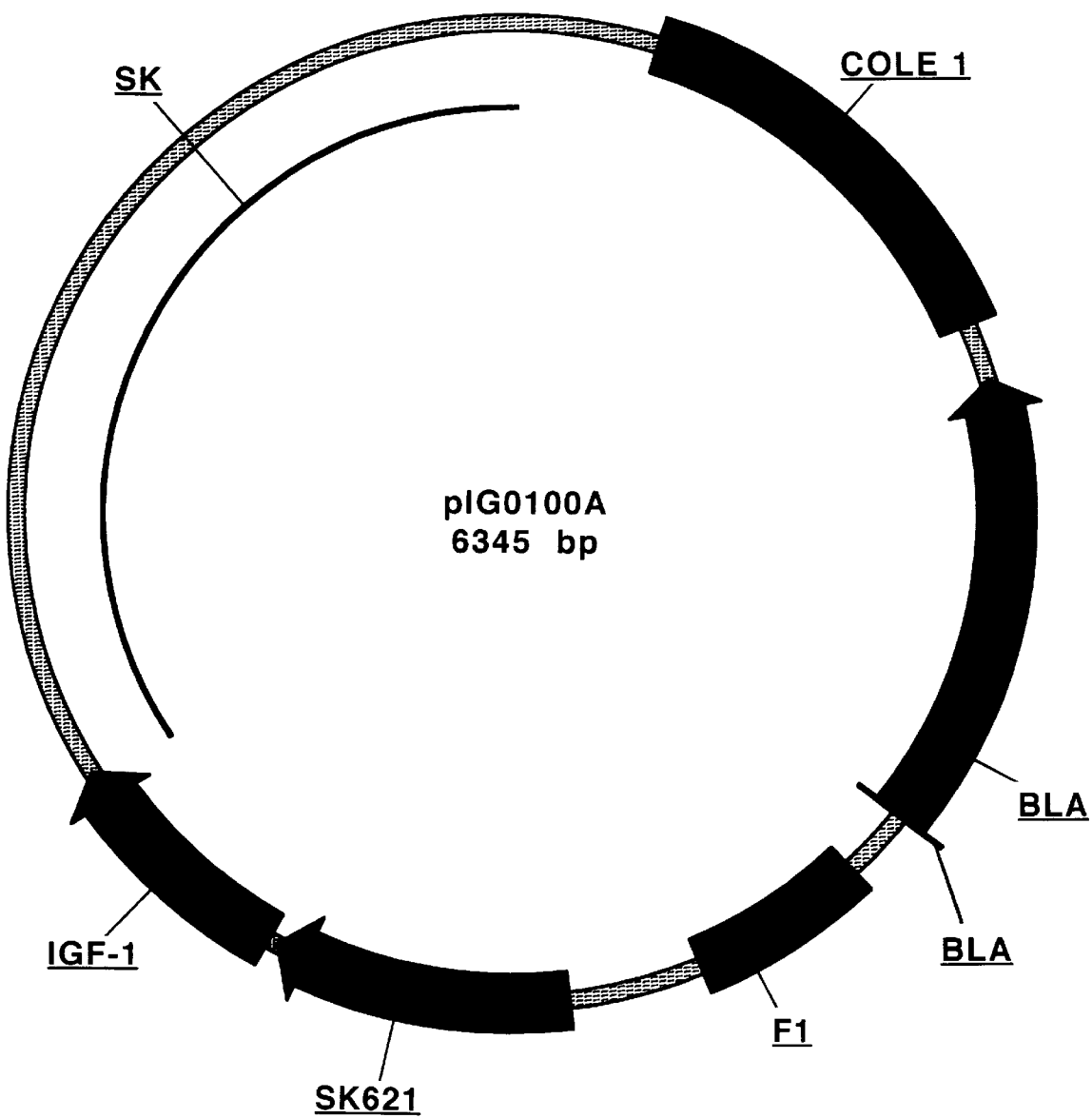
FIG. 14 is a schematic representation of the plasmid pIG0100A for SK733IGF-ISK-2 with ampicillin resistance backbone.

The SK733 IGF-1SK2 plasmid construct (pIG0100A) is disclosed in FIG. 14. This plasmid has an ampicillin resistance backbone and encodes for IGF-1. The complete sequence of pIG0100A can be found in FIG. 15.

Figure 16:
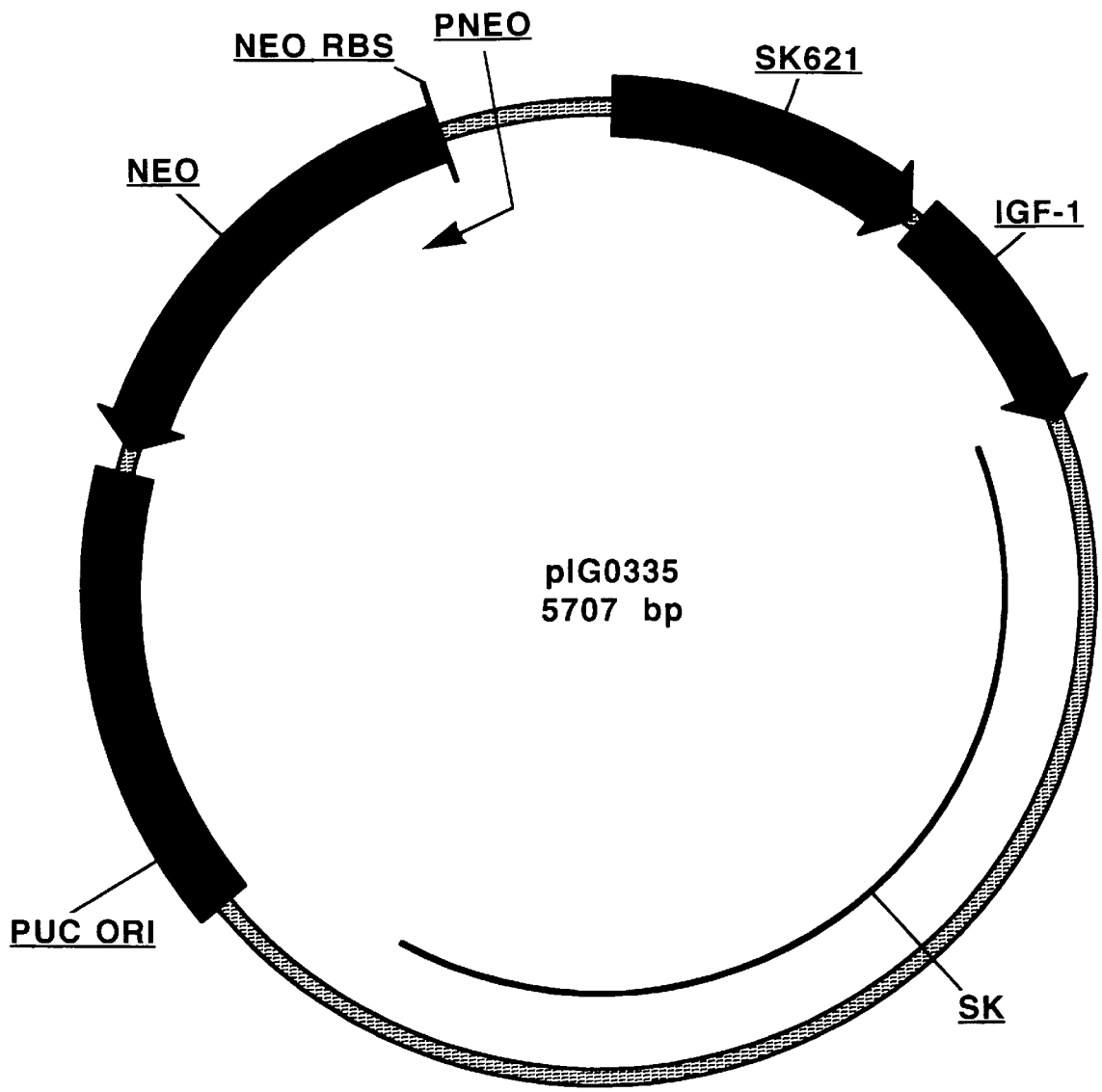
FIG. 16 is a schematic representation of the plasmid pIG0335 for SK733IGF-ISK-2 with kanamycin resistance backbone.

In addition, the plasmid construct pIG0335 (FIG. 16) is similar to pIG0100A but it contains a Kanamycin resistance backbone. The complete sequence can be found in FIG. 17 (Seq. ID. 8).

Myogenic Cell Cultures

Primary chicken myoblast cultures from hind limbs of day 11 white leghorn chick embryos were developed according to the protocol described in the art. Grichnik et al., *Nucleic Acids Research* vol. 14, pp. 1683–1701 (1986). Enriched myoblasts were plated at a density of 2×10$^5$ cells per 60 mm collagenized tissue culture dish.

Myogenic mammalian $C_2C_{12}$ and Sol 8 cells (1×10$^5$) were subcultured onto 60 mm dishes one day before transfection.

DNA Transfer

Tissue culture cells were transfected with plasmid DNA by the calcium phosphate precipitation-glycerol shock protocol as known in the art. Wigler et al., *Cell* vol. 14, 725–731 (1978). A total of 10 μg of DNA was used to transfect each 60 mm dish of tissue culture cells. Transfections were done in quadruplicate and with three different MVS-CAT-MLC plasmid preparations to control for variations in DNA quality and plating density of cells.

CAT Assay

After transfection two populations of cells, coinciding with replicating myoblasts and post-fusion myotubes were harvested, and assayed for CAT activity as described in the art. Gorman et al., *Molec. and Cell. Biol.*, vol. 2, pp. 1044–1051 (1982). Cell pellets were lysed by repetitive freeze thaw cycles in 50 μl of 250 mM Tris-HCl ph 7.5. The production of acetylated [$^4$C] chloramphenicol (0.5 μCi per assay, 57.8 mCi/mMol) was assayed for 90 minutes at 37° C. Acetylated chloramphenicol was monitored by autoradiography following thin layer chromatography on silica gel plates. Separated acetylated chloramphenicol spots were quantitated by scanning on a Betagen phosphoimager screen. Data was expressed as the percentage of converted [$^{14}$C] chloramphenicol per μg cell protein. Protein concentration of cell extracts was determined by the method of Bradford (*Anal. Biochem.*, vol. 72, pp. 254–258 (1976)) at each time point to insure uniformity in the assays.

Activity of Expression Vector Constructs

To determine the efficacy of actin promoter/gene IGF-I hybrid genes in mouse myogenic cells the expression vector was studied using these genes in the background of mammalian $C_2Cl_{12}$ myoblasts by making a population of stable transfected $C_2C_{12}$ myoblasts. The altered IGF-I expression levels were directly evaluated in these stable myoblast cell lines. Each IGF-I construction (FIG. 4) was co-transfected with the drug selectable vector EMSV-Hygromycin into mouse $C_2C_{12}$ cells. After two weeks of selection, a population of stable myoblasts was selected. A population of $C_2C_{12}$ myoblasts stably transfected only with EMSV-Hygromycin served as the controls. Visual inspection of the transfected myoblast revealed several insights into the role of IGF-I on muscle cell differentiation that would not be obvious in transgenic mice. In general all of the myogenic cell lines containing IGF-I genes caused myoblasts in growth media (10% fetal calf serum) to replicate more extensively than controls. Changing culture medium to 2% horse serum initiates the differentiation process. In the process, control $C_2C_{12}$ myoblasts fuse to form multinucleated myotubes over a period of four days. At the same cell density per culture dish, myoblasts containing SK733IGF-I, SK202IGF-I-SK, SK733IGF-I-SK1 and SK733IGF-I-SK2 (FIGS. 14–17) fused at least two-to-three days earlier than $C_2C_{12}$ or EMSV-Hygromycin control myoblasts.

In order to study the steady state accumulation of IGF-I MRNA in $C_2C_{12}$ myoblasts, equal amounts of total cellular RNA was isolated from stably transfected $C_2C_{12}$ myoblasts grown in growth media ("G") or differentiation media ("D"). The RNA was electrophoretically separated on denaturing agarose gels, transferred onto nylon filters and probed with uniformly $^{32}$p labeled full length human IGF-I cDNA under standard hybridization techniques. The intensity of the autoradiographic signal on X-ray film provides a relative measure of mRNA accumulation, an overall index of combined transcriptional activity and mRNA stability of the expression vectors. The IGF-I mRNA in vector, SK202IGF-I-3'SVa did not accumulate in myotubes above myoblast levels. This is a typical expression activity. The SK733IGF-I vector contains the IGF-I 3'UTR. The IGF-I MRNA from this vector accumulated in myotubes but at levels substantially lower than SK202IGF-I-SK or SK733IGFI-SK2. (FIGS. 14–17.) These later two vectors contain the skeletal actin 3'UTR and 3'NCR. Since, the primary difference in these vectors is the 3'UTR, the increased stabilization of the MRNA transcripts due to the skeletal 3'UTR accounts for about a 100-]fold difference in MRNA content.

Measurement of Secreted Levels of IGF-I from IGF-I Gene Delivery by the Expression Vector In order to measure the amount of IGF-I synthesized and secreted into the media, differentiated myotube cultures were grown in minimal media (DMEM and 0.05% bovine serum albumin, RIA grade). SK733IGF-I-SK2 is the most effective construction to express IGF-I in muscle cells. IGF-I was assayed by both radioimmunoassays of tissue culture media and by immunoperoxidase staining of cells. We have found increased levels of IGF-I during the fusion of several of our muscle cultures. The comparison of levels from different expression vectors are shown in Table I. In control cultures, the level of IGF-I was in the range of 0.2–0.5 ng/ml. In comparison, vector SK733IGF-I-SK2 (pIG0100A or pIG0335) has levels of IGF-I at least one hundred times greater.

TABLE I

IGF-I Levels in Stably Transfected $C_2C_{12}$ Myoblasts

| Construction | IGF-I (ng/ml of media/4 days) |
| --- | --- |
| SK202IGF-I-3'SVa | 4.4 |
| SK733IGF-I | 3.8 |
| SK733IGF-I-SK2 | 79.0 |
| Control $C_2C_{12}$ | 0.5 |

In a similar manner, immunoperoxidase staining of myogenic cultures revealed the increased production of immunological reactive IGF-I in stable transfected myoblasts but not in the control EMSV-Hygromycin transfected myoblasts or in perfusion $C_2C_{12}$ cells. Antibodies against the A and D regions were used at dilutions of 1:1000. All of the transfected lines including SK202IGF-I were positively immunoperoxidase stained. Thus, it is clear that enhanced levels of IGF-I are being synthesized and exported from the stable myoblasts.

Determination of MRNA Stability in Muscle Cell Culture

The rate of measuring mRNA degradation in primary avian myogenic cultures containing well differentiated myotubes was measured by an extended pulse-chase method using [$^3$H] uridine. Total RNA in muscle cell cultures was labeled to equilibrium by a 48-hour incubation in media containing 0.2 mCi/ml of [$^3$H] uridine starting on day 3 after plating myoblasts. Under these conditions significant label was incorporated into the most stable of the contractile mRNAs. After labeling, the cells were washed in DMEM and the [$^3$H] uridine chase by incubating cells in DMEM containing 10 mM uridine and 10 mM cytidine for two hours and then changed to DMEM, 10% horse serum, 5% chick embryo extract, 1 mM uridine and 1 mM cytidine for the duration of the experiments. No significant differences were observed in the specific activity of the labeled RNA represented mostly by ribosomal RNA over a three-day period. This is consistent with previous reports on ribosomal RNA stability in growing cells (Abelson, H. et al., *Cell* vol. 1, pp. 162; 1974) and in muscle cells (Krauter, K. S.; Soerio, R. and Nadal-Ginard, *J. Mol. Biol.*, vol. 134, pp. 727–741; 1979).

RNA was isolated from these cultures at various times after the chase. To measure the relative levels of specific tritiated mRNAs, DNA probes to the untranslated regions of the actin mRNAs and to the coding regions of the other mRNA were used. These probes were bound to nylon filters, hybridized with $^3$[H]-RNA at 1×106 cpm/ml, and washed and assayed as described in the art. Zhu et al., *J. Cell Biology*, Vol. 115, pp. 745–754 (1991). Quantitation was done by direct counting of $^3$[H]-RNA bound to the nylon membrane, and expressed as a percentage of hybridized counts. Table II provides a summary of the kinetic hybridization assays.

TABLE II

Half-lives of Muscle and Non-Muscle mRNAs in Primary Muscle Cell Cultures

| mRNA | Half-life (hours) |
| --- | --- |
| Skeletal α-actin | 19.4 +/– 2.4 |
| Cardiac alpha actin | 13.5 +/– 1.6 |
| Beta actin | 8.4 +/– 1.1 |
| Fast Myosin light chain 1/3 | 60 |
| Cardiac Tropinin C | 14.7 +/– 1.2 |
| GAPDH | 10.7 +/– 1.4 |

Measurement of the Stability IGF-I Hybrid 3'UTR Transcripts in Muscle Cells

The steady state levels of different mRNAs reflect the balance between the rate of synthesis of new mRNA and the rate of mRNA degradation. This measurement was used to determine the ability of muscle specific 3'UTR to impart MRNA stability. Hybrid IGF-I constructs as described above were stably transfected into myogenic $C_2C_{12}$ myoblasts, as shown above. These were challenged with a transcription blocker actinomycin D (8 µg/ml) added to the culture media of differentiated myotubes. Messenger RNA stability was monitored by assessing the amount of residual mRNA remaining after transcriptional block, by RNA blotting with a [$^{32}$P] labeled human insulin-like growth factor I CDNA probe.

Construct SK733 IGF-I-3'SK2 showed substantial amounts of RNA indicating enhanced stability 12 hours after actinomycin D addition. Construct SK202IGF-I-3'SVa showed minimal amounts of RNA 8 hours after actinomycin D addition. This can be contrasted with the lack of stability of SK733 IGF-I which diminished by 4 hours after actinomycin D addition.

Assay of Expression Vector Activity of Hybrid Constructs Containing the Fast Myosin Light Chain ⅓ 3'UTR The sequence of the chicken skeletal muscle light chain ⅓ (MLC) untranslated region is 342 nucleotides in length (Nabeshima, Y. et al., *Nature*, vol. 308, pp. 333–338; 1984). Oligonucleotides encoding the beginning (5'GAGGACGTCCCCAG; Sequence I.D. No. 3) of the 3'UTR and the terminal 3'UTR sequence (5' GTCATT-TAGGGACAACAG; Sequence I.D. No. 4) were used in a polymerase chain reaction to synthesize the intact MLC 3'UTR. This was reductively subcloned into the Eco RV site in the cloning cassette of pBluescript II SK (+/–) phagemid. Verification of the MLC 3'UTR was done by dideoxy sequencing using T3 and T7 primer oligos. The plasmid was linearized with Pst I, treated with T4 polymerase, and then released by digestion with Kpn I. An expression test vector was constructed which contained the bacterial Tn9 reporter gene chloramphenicol acetyl transferase, linked downstream of the skeletal α-actin promoter, 5' cap, leader and the first intron, as described above. In this vector, a portion of the bluescript II cassette (HindIII to Kpn-T) was cloned after the termination codon of CAT. This provided restriction sites to clone in different 3'UTR sequences. MLC 3'UTR was directionally cloned into the blunt ClaI site and the sticky ended KpnI site. Taking advantage of MLCs unique Eco RI site that is asymmetrically placed towards the 5' end of the UTR, the appropriately oriented constructions were selected. In a similar way, the skeletal 3'UTR and the SV40 t-intron 3'UTR poly A addition sequences were cloned adjacent to the end of the CAT reporter gene in the expression vector. The recombinant clones were amplified in DH5 alpha bacterial cells and plasmids were purified from bacterial lysates by two cesium chloride density gradient centrifugations. Plasmid DNA used in transfections were at least 50% form I circular DNA.

Stability of Muscle MRNA Species

Table II summarizes the stability of myogenic contractile protein mRNAs in comparison to the housekeeping glycolytic enzymes, glyceraldehyde-phosphate dehydrogenase, and the non-myogenic β-actin MRNA in well differentiated muscle cells in culture. Calculated MRNA half lives in Table II demonstrates that fast myosin light chain 1 mRNA was the most stable of all the mRNAs examined with a calculated $t_{1/2} > 60$ h. Skeletal α-actin with a $t_{1/2}$ of 19.4 h was considerably more stable than the nonmuscle β-actin and GAPDH mRNA with $t_{1/2}$ of 8 and 10 hrs. It is known that β-actin is an unique actin isoform found in replicating myoblasts and nonmyogenic cell types, but not in well differentiated myotubes (Hayward, L. J.; Zhu, Y. Y.; and Schwartz, R. J., *J. Cell Biology*, vol. 106, pp. 2077–2086; 1988).

The Skeletal α-Actin 3'UTR Increases the Half-Life of mRNA in Muscle Cells

The functional role of 3'UTRs on influencing the half life of RNA transcripts in muscle cells was determined. Several expression vectors containing different 3'UTRs cloned adjacent to the IGF-I translation termination codon were used. In this type of analysis, IGF-I served as a reporter gene, and actinomycin D was used to block transcription in stable $C_2Cl_{12}$ muscle cell lines. Time RNA samples taken after the addition of actinomycin D were probed with labeled human IGF-I cDNA. Transcripts containing the natural IGF-I 3'UTR were found to turnover rapidly with a half life of less than ½ hour. Transcripts containing the skeletal a-actin 3'UTR showed a high level of stability, corresponding to at least a $T_{1/2}$ of 18 hours. Even transcripts containing $SV_{40}$ and 3'UTR and poly A addition signals showed a reduced half-life of 8 hours. Stability of IGF-I constructs containing skeletal α-actin 3'UTR corresponded well with the half-life of the endogenous skeletal α-actin mRNA.

Comparison of Myosin Light Chain 3'UTR with Skeletal α-Actin 3'UTR in Stimulating Vector Expression in Muscle Cells To demonstrate that the 3'UTR of another myogenic restricted gene is equivalent to the skeletal α-actin 3'UTR in the expression vector, the MLC, with a half-life of 60 hours, was used to measure increasing gene expression in muscle cells. As described above, DNA constructions which linked together the skeletal α-actin promoter and the MLC 3'UTR were made. A comparison was made of the activity of: (i) SV2CAT, a standard for an active promoter/enhancer; (ii) MVS-CAT with an SV40 3' t-intron/poly A site; (iii) MVS-CAT with an skeletal α-actin 3'UTR; and (iv) MVS-CAT with an MLC 3'UTR. Four replicate transfections, for each CAT construction, were assayed during replication (pre-fusion, 24 hr) or following myoblast fusion (72 hr). In the case of constructs containing the MLC 3'UTR, four sets of transfections were done with three different plasmid constructions.

Figure 5:
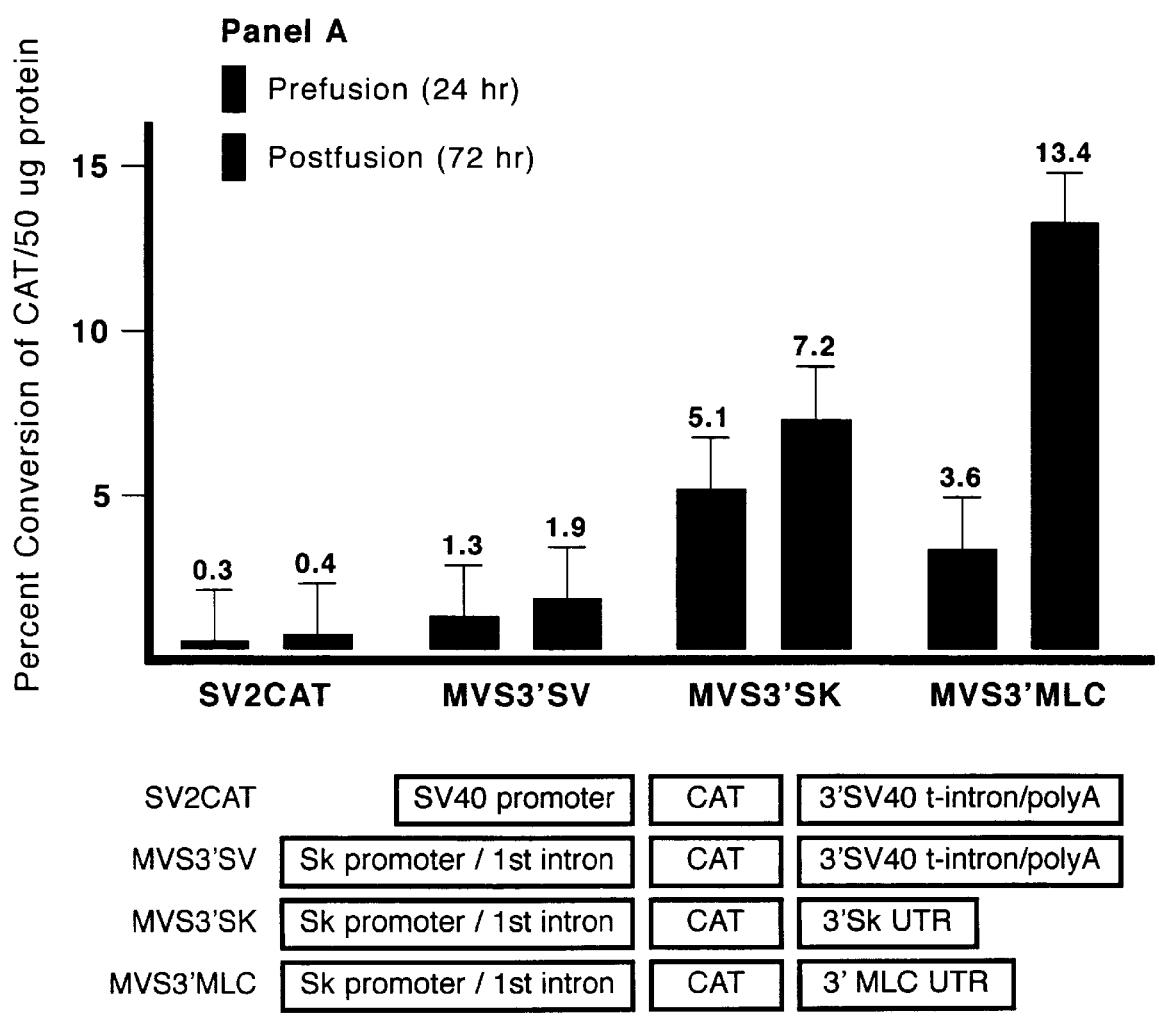
FIG. 5 shows fast myosin light chain 3'UTR potentates CAT activity in avian primary myoblasts, and substitutes for the skeletal actin 3'UTR.

The role of the 3'UTR sequences was evaluated by assaying CAT enzymatic activity as shown in a representative set of experiments in FIG. 5 and Table III. Vectors containing myogenic sequences increased CAT activity following fusion as was observed for the endogenous skeletal α-actin gene. Vectors containing the skeletal actin promoter (MVS 3'SV) were approximately 5 times more active than the SV2CAT vector following myoblast fusion. Substitution of the skeletal α-actin 3'UTR for the SV40 UTR increased activity by about another 4 fold. The MLC 3'UTR provided another two to three fold increase in activity over the skeletal α-actin 3'UTR. Overall, MVS-CAT with the 3'UTR appropriately switched gene expression activity during the transition from replication to fusion, and increased CAT activity by eight to tenfold over MVS-CAT 3'SV.

Figure 6:
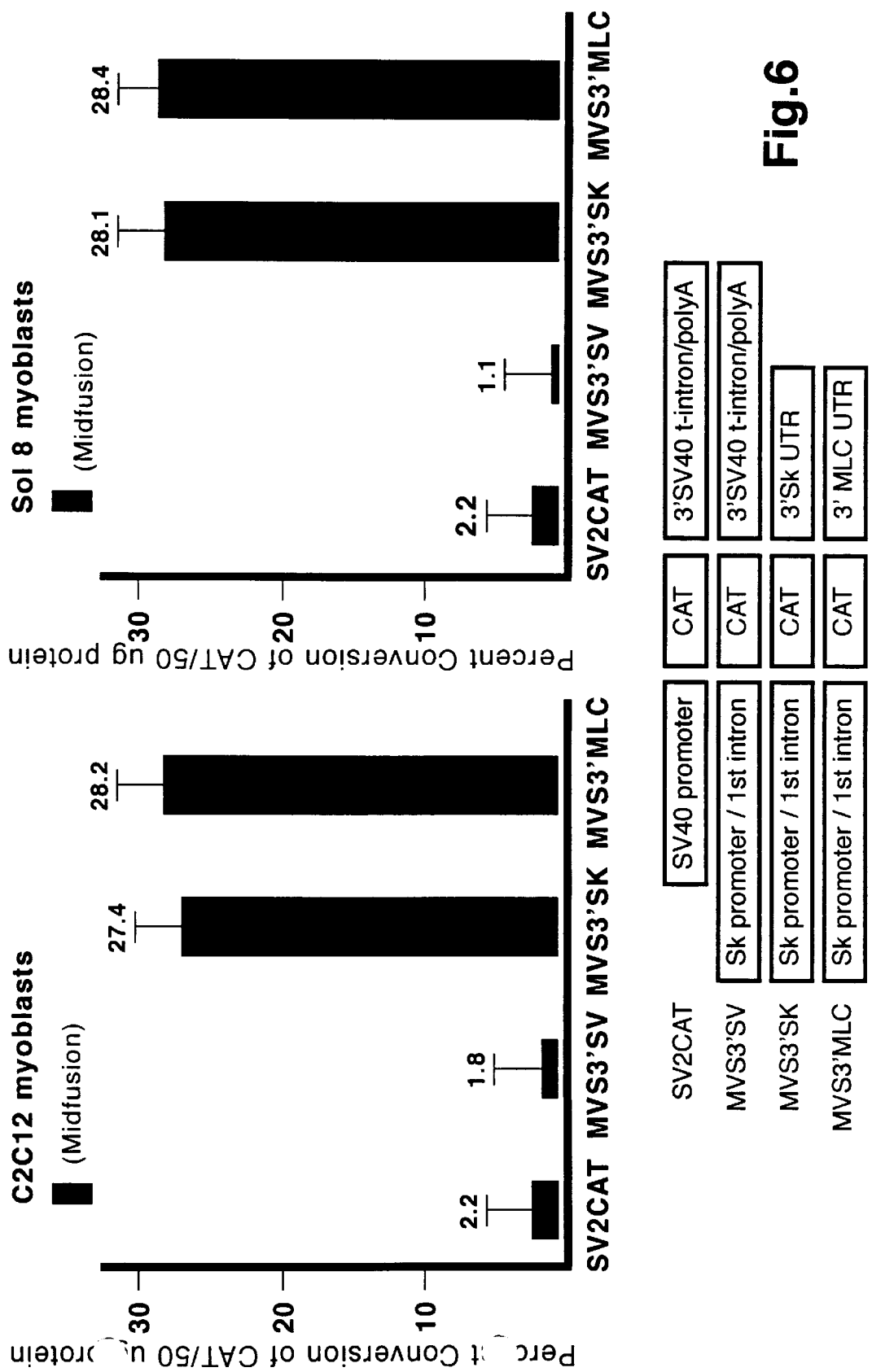
FIG. 6 shows fast myosin light chain 3'UTR potentates CAT activity in Sol 8 and $C_2C_{12}$ myoblasts, and substitutes for the skeletal actin 3'UTR.

In FIG. 6, a similar degree of activity dependent upon the skeletal and MLC 3'UTRs in mammalian $C_2C_{12}$ and Sol 18 myoblasts was observed. The myosin light chain is even more effective than the skeletal α-actin 3'UTR in potentiating gene expression activity in differentiated avian and mammalian muscle cells. As shown above, the myosin light chain 3'UTR is capable of being substituted for the skeletal 3'UTR.

TABLE III

Analysis of CAT Activity in Transfected Avian Myoblasts

| Construct | | MEAN CAT Activity (% Conv) | Stand. Dev. |
|---|---|---|---|
| SV2CAT | (pre) | 0.3 | 0.02 |
| | (post) | 0.4 | 0.1 |
| MVS-CAT 3'SV | (pre) | 1.3 | 0.17 |
| | (post) | 1.9 | 0.25 |
| MVS-CAT 3'SK | (pre) | 5.3 | 0.42 |
| | (post) | 7.8 | 1.04 |
| MVS-CAT 3'MLC | (pre) | 3.8 | 0.5 |
| (clone 22) | (post) | 15.5 | 0.6 |
| (clone 45) | (pre) | 3.25 | 0.2 |
| | (post) | 13.1 | 1.4 |
| (clone 52) | (pre) | 2.7 | 0.3 |
| | (post) | 20.2 | 8.7 |

Insertion of Expression Vectors into Transgenic Mice

Transgenic mice carrying SK202IGF-I-3'SVa or SK202IGF-I-SK were generated by standard oocyte injection (Brinster, et al, *Proc. Natl. Acad. Sci. USA*, vol. 82, pp. 4438–4442 (1958)) and bred to demonstrate stable transmission of transgenes to subsequent generations. Transgenics were identified by polymerase chain reaction or Southern genomic DNA blotting analysis from tail cut DNA. Transgenics were tested for muscle specific expression of the transferred IGF-I vector by RNA blotting of total RNA isolated from several tissues. Independent transgenic mouse lines 5484, 5496, 5832, 5834 were generated with SK202IGF-I-3'SVa, containing the SV40 3' intron and poly A addition sequence. Mice from these strains were found to have weak expression primarily in heart tissue, but very low levels were found in skeletal muscle and non-myogenic tissues such as the kidney and brain. Independent transgenic mouse lines 3357, 3359 generated with SK733IGF-I-3'SK2 (pIG0100A or pIG0335). Mice from these strains were found to have elevated expression levels of IGF-I. These levels are comparable to the endogenous mouse α-actin gene activity. These levels from SK733IGF-I-3'SK2 (pIG0100A or pIG0335) show at least 100–1000 fold greater accumulation of IGF-I mRNA in comparison to the levels produced by the SK202IGF-I-3'SVa vector. The addition of the skeletal α-actin 3'UTR and 3' flanking region allowed for a preferential increase in IGF-I RNA in skeletal muscle rather than cardiac. Thus, the 3'UTR and 3' NCR of skeletal α-actin have an important role in enhancing muscle specific gene expression.

Mice from these strains demonstrated increased muscle mass and reduced percentages of body fat as compared to the parental types. The use of human IGF-I in the mouse demonstrates the cross-species applicability of this particular gene.

In addition, by providing contiguous 3' NCR, IGF-I is buffered against outside genomic sequences and is thus more protected from position effects, when integrated into the genome. In addition, by providing natural terminating sequences, the additional regulatory sequences that mark the transcriptional domain of skeletal A-actin prevent read through transcription, improve tissue specificity, developmental timing and transcriptional activity. Presence of 3'NCR sequence allows for a single copy of the integrated vector to produce 40–50% of the transcriptional activity of the endogenous sequences.

Somatic Gene Transfer to Skeletal Muscle In Vivo

To demonstrate an effect of the vectors of the present invention as used in vivo gene therapy, vectors were injected into adult muscle for the express purpose of expression of a particular polypeptide. The growth hormone-deficient mouse strain, little, was used in these studies. Vector SK733IGF-I-SK2 (pIG0100A or pIG0335), or control vector SKSK, was pelleted by sedimentation, dried under vacuum and punctured into the quadricep muscle (20 µg/pellet–3 pellets/muscle) of 2 sets of 6 little mice. The entire muscle from each animal that received an inoculation was removed 2 weeks following introduction of the DNA and assayed for IGF-I protein in the tissue. The amount of IGF-I in each tissue was assayed by using a radioisotopic assay. A slight yet significant ($p>0.05$) increase was observed in IGF-1 expression (Table IV), from 4.2 ng IGF-1/100 µg total protein of muscle lysate in mice with vector only (no IGF-1) to 6.9 ng IGF-1/100 µg total protein of muscle lysate in those with the vector SK733IGF1-3'SK.

TABLE IV

IGF-I Levels in Tissues of MVS-Injected little MICE

| Mouse# | Strain | Plasmid | IGF-I (ng/100 ug) |
|---|---|---|---|
| 776 | little | PSKSK | 4.2 |
| 777 | little | PSKSK | 4.2 |
| 778 | little | PSKSK | 4.5 |
| 779 | little | PSKSK | 3.9 |
| 780 | little | PSKSK | 3.9 |
| 781 | little | PSKSK | 4.2 |
| Average | | | 4.15 + 0.21 |
| 782 | little | pSK733IGFSK | 4.5 |
| 783 | little | pSK733IGFSK | 6.3 |
| 784 | little | pSK733IGFSK | 8.2 |
| 785 | little | pSK733IGFSK | 6.9 |
| 786 | little | pSK733IGFSK | 8.4 |
| 787 | little | pSK733IGFSK | 7.0 |
| Average | | | 6.88 ± 1.08 |

Intramuscular Injections of a IGF-I Myogenic Vector in Diabetic Rats.

The effect of intramuscular injections of a muscle-specific DNA vector ("MSV") carrying the human insulinlike growth factor-I ("IGF-1") on diabetes-induced alterations in body and muscle weights, plasma glucose levels and the MRNA level from the injected MSV-IGF-I was examined. An IGF-I expressing MSV was chosen for this work since injections of recombinant IGF-I have been shown to have anabolic effects in a number of models of cachexia.

Diabetes was induced in male Sprague-Dawley rats (175200 g) with intravenous injections of streptozotocin (STZ; 55 mg/kg) dissolved in sodium citrate buffer (0.05M, pH 4.5). Control non-diabetic animals were age, weight and sex matched and received equal volume injections of vehicle. Diabetes was confirmed by the onset of hyperglycemia, glucosuria, and reduced rate of growth. Three days following STZ administration, non-fasted animals were anesthetized with pentobarbital (50 mg/kg) and blood samples were obtained by cardiac puncture. Blood was transferred to EDTA-containing tubes, centrifuged at 3000×g for 15 min and stored at −70° C. The gastrocnemius was injected bilaterally following direct visualization of the muscle via a cutaneous incision. The right gastrocnemius muscle of individual rats was injected with either 0, 50, 200, or 800 µg of MSV in 200 µl of isotonic saline solution. The contralateral (left) gastrocnemius received 200 µl injections of isotonic saline. The MSV used in this series of experiments was Sk-733-IGF-I-Sk2 as described above. Six days following intramuscular injection of muscle-specific vector, the animals were deprived of food (12–16 hrs) followed by euthanization by decapitation. Blood was then collected and the entire gastrocnemius muscle was removed (dissection from tendon to tendon).

Figure 7:
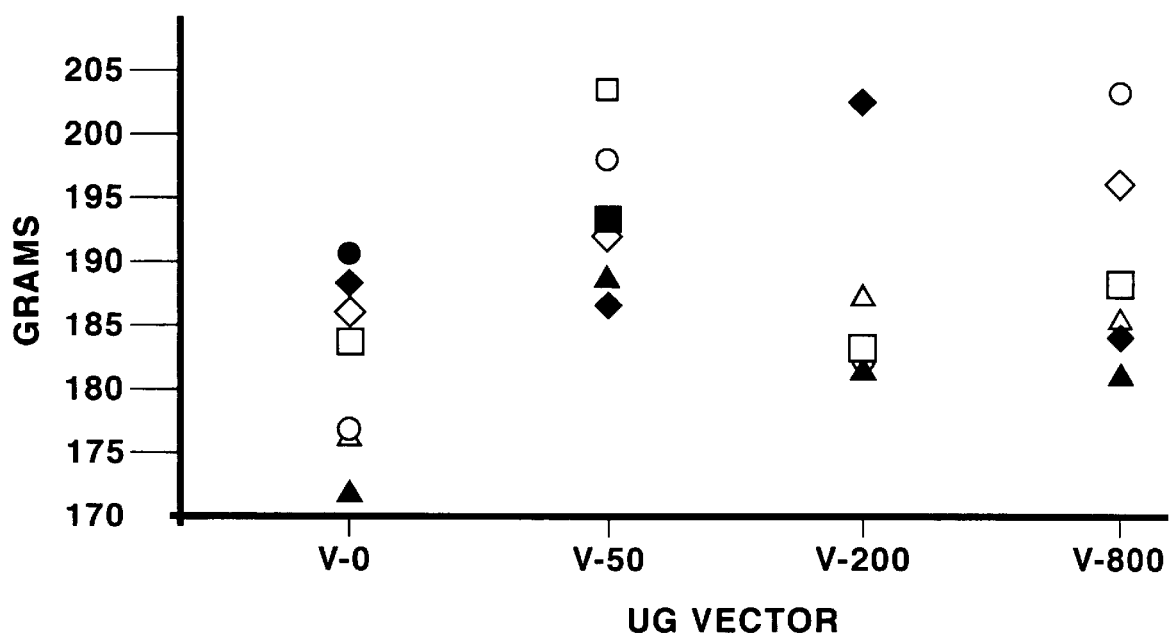
FIG. 7 shows the change in body weight of diabetic rats treated with IGF-I containing MVS.

For the analysis of vector effects on body and muscle weight dosage groups were matched on pre-vector injection body weight and only diabetic animals were included in the analysis. The plasma glucose criteria for inclusion in the analysis was a non-fasting plasma glucose level greater than 300 mg/100 ml. Pre-vector injection body weights were matched by only including animals with body weights between 175–195 gm. For the analysis of vector effects on plasma glucose levels the groups were matched on pre-vector injection plasma glucose levels. Intramuscular injections of MSV result in increased body weight (FIG. 7; Mean±SD; Vehicle Only=181.37±6.17; 50 µg=193.43±5.71; 200 µg=186.6±8.01; 800 µg=191.14±7.54). This body weight increase is statistically significant at the 50 and 800 µg, but not the 200 µg, dose level (a priori t-test: Control vs. 50 µg, t=3.57, df=12; Control vs. 200 µg, t=1.17, df 10; Control vs. 800 µg, t=2.29, df=12).

Figure 8:
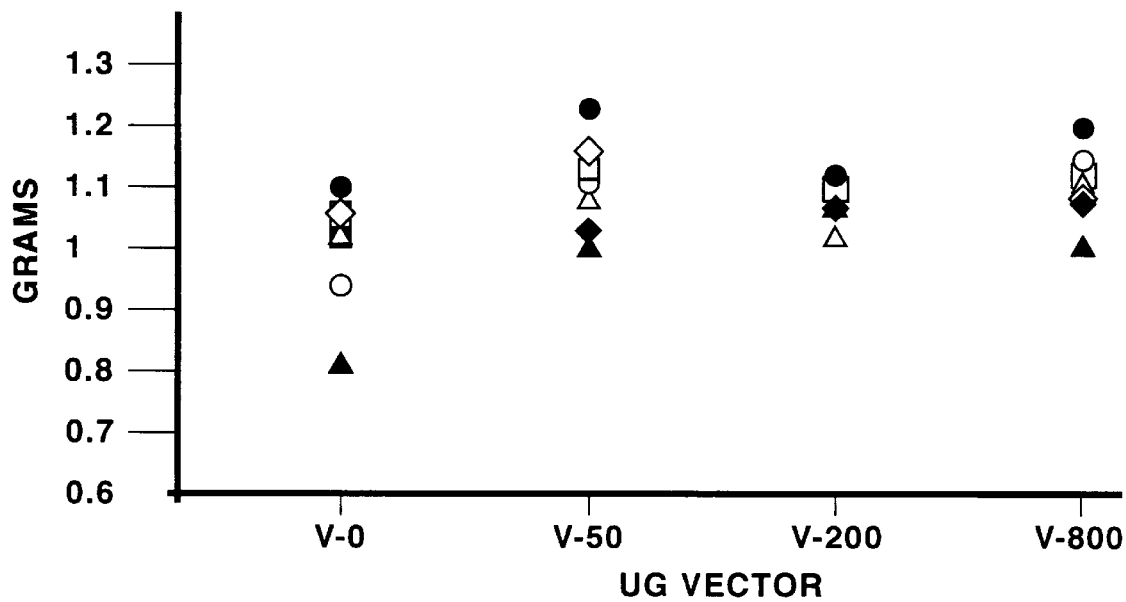
FIG. 8 shows the change in the weight of the gastocnemius muscle (the site of injection) of diabetic rats treated with IGF-I containing MVS.

In addition to increasing body weight MSV injections also increase the weight of the vector injected gastrocnemius (FIG. 8; Mean±SD; Vehicle Only=1.00±0.08; 50 µg 1.10±0.07; 200 µg=1.07±0.03; 800 µg=1.09±0.05) This increase in vector injected gastrocnemius weight is statistically significant at the 50 and 800 µg, but not the 200 µg, dose level (apriori t-test: Control vs. 50 µg, t=2.32, df=12; Control vs. 200 µg, t=1.75, df 10; Control vs. 800 µg, t=2.32, df=12). The weight of the contralateral gastrocnemius was also increased but this increase did not reach statistical significant (Mean±SD; Vehicle Only=1.00±0.07; 50 µg=1.07±0.06; 200 µg=1.05±0.01; 800 µg=1.08±0.06; a priori t-test: Control vs. 50 µg, t=1.72, df=12; Control vs. 200 µg, t=1.43, df 10; Control vs. 800 µg, t=2.11, df=12).

Figure 9:
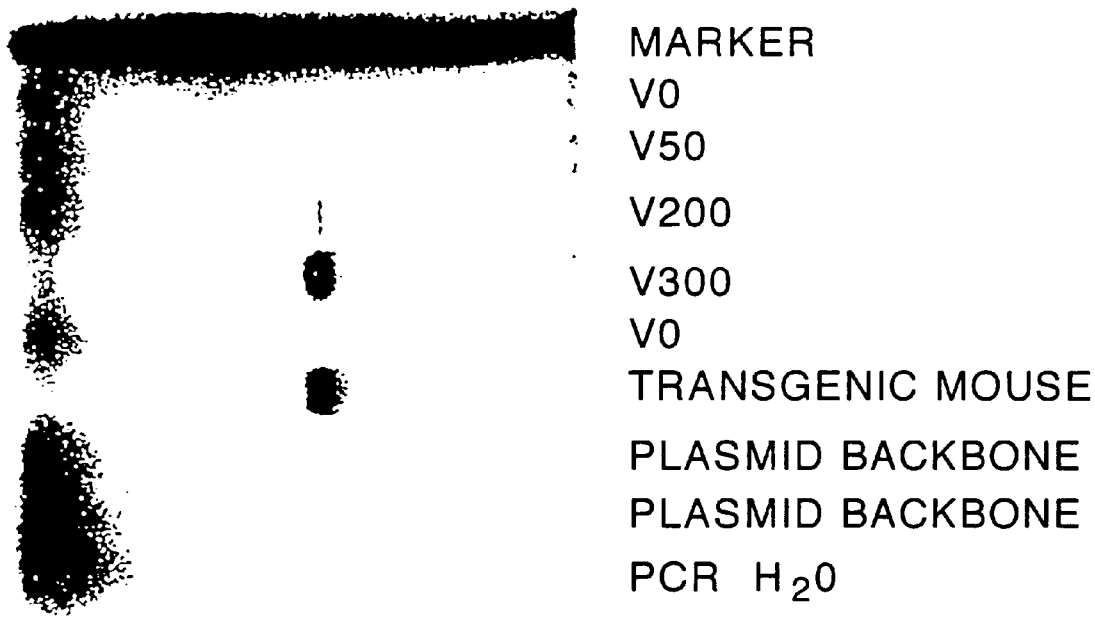
FIG. 9 shows the product amplified from IGF-I specific primers of cDNA generated from MVS-IGF-I injected mouse muscle.

The level of expression of the injected MSV-IGF-I construct was assessed by determining the level of IGF-I specific mRNA. Whole cell RNA isolated from the injected and control, contralateral, gastrocnemius, was treated with DNAase and subjected to reverse transcription using oligo-dT as a primer in order to generate cDNA replicas of mRNA. The cDNA was than reacted with IGF-I specific primers in a polymerase chain reaction to estimate the level of expression of mRNA in the original muscle sample. The bands corresponding to IGF-I-specific primer amplified products are shown in FIG. 9. These data indicate that the MSV IGF-I construct is being expressed at significant levels in the injected muscle. The control muscle showed no expression of human IGF-I.

Figure 10:
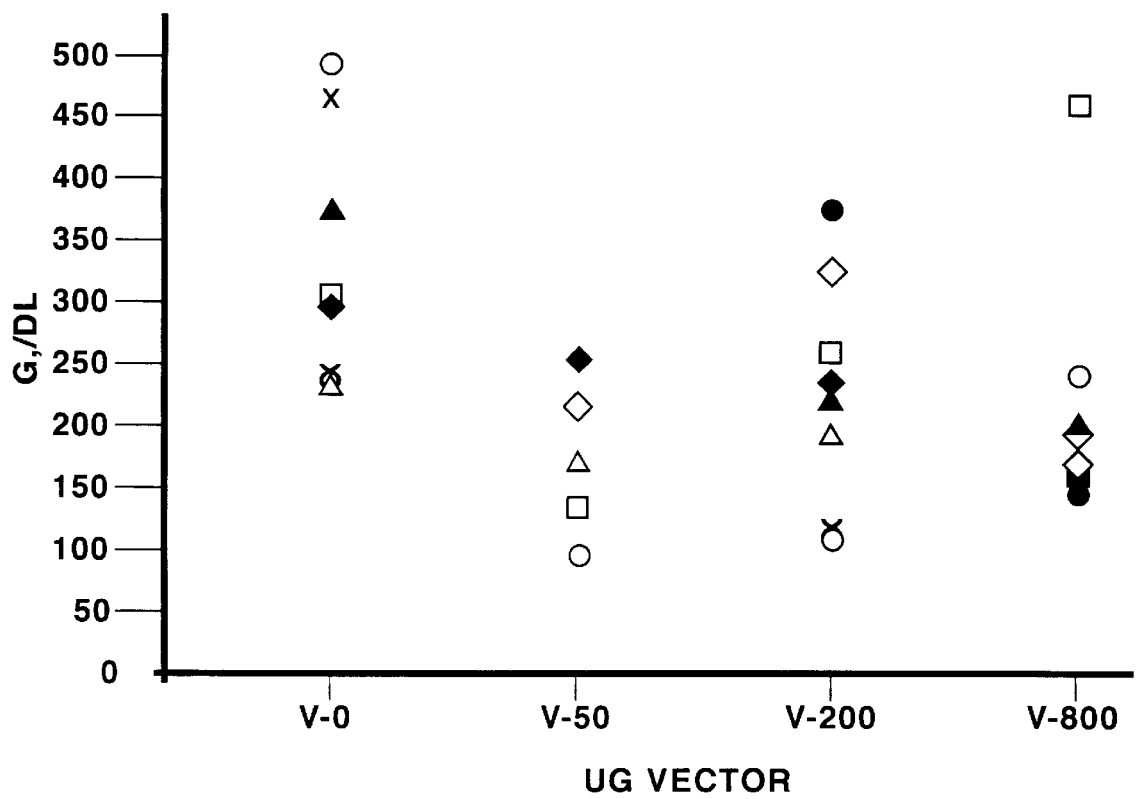
FIG. 10 shows the change in plasma glucose levels of diabetic rats treated with IGF-I containing MVS.

Relative to the Control group fasting plasma glucose levels in the 50 µg MSV dose group were significantly lower (FIG. 10; Mean±SD; Vehicle Only=277.14±113.65; 50 µg=155.42±37.54; 200 µg=224.06±89.21; 800

μg=216.57±100.55 mg/100 ml). (apriori t-test: Control vs.50 μg, t=3.23, df=12; Control vs. 200 μg, t=1.04, df 17; Control vs. 800 μg, t=1.09, df=16).

These findings indicate that intramuscular injections of MSV (SK-7331-IGF-I-SK2; see FIGS. 14–17) reduce diabetic hyperglycemia and increase body and muscle weight suggesting that MSV expression levels are sufficient to trigger an anabolic effect. The finding that the vector injected, but not the contralateral, gastrocnemius significantly increases in weight suggests a difference in local IGF-I concentration in the two muscles.

Expression of Human Factor IX by MVS in $C_2C_{12}$ muscle cells

Muscle specific vector (SK-F.IX-SK) containing the full length factor IX sequence can be transiently expressed in $C_2Cl_{12}$ cells. The $C_2C_{12}$ myoblasts and myotubes were transfected using $CaPo_4$ or lipofectin and the human Factor IX secreted in the conditioned medium was analyzed using an ELISA. The $C_2C_{12}$ cells, purchased from the American Type Culture Collection, were plated at a density of 0.5× $10^6$/dish in a medium containing DMEM with high glucose, 10% FBS, and 1% penicillin streptomycin. Cells were transfected as myoblasts at 24 h after plating or allowed to differentiate in medium with 2% horse serum and transfected as myotubes a week after initial plating. Both myoblasts and myotubes were transfected with 20 μg DNA either in saline, lipofectin (1:7 DNA:lipofectin), or $CaPO_4$ precipitates for 5 h in a serum free medium. After transfection, cells were fed with DMEM containing 2% horse serum and the media was collected at 24, 40, 72, 96, 120, and 130 h for quantitation of human Factor IX.

The amount of human Factor IX secreted in the culture medium was quantitated by a ELISA using a modification of the procedure described by Kay et al. Kay et al., Human Gene Therapy vol. 3 pp. 641–647 (1992). Briefly, 96-well plates were coated with a monoclonal mouse anti-human Factor IX antibody at a concentration of 2 μg/ul for 1 h at room temperature. Samples (50 μl) of conditioned media were than added and allowed to bind for 1 h at 37° C. This was followed by the application of a 1:10,000 dilution of a polyclonal rabbit anti-human Factor IX antibody. The antigen-antibody complex was recognized by a peroxidase conjugated anti-rabbit IgG. The assay was developed with 3,3', 5,5', tetramethyl-benzidine dihydrochloride (TMBD) and $H_2O_2$ in citrate/phosphate buffer and the color changed measured at 405 nm.

As shown in Table V, no detectable levels of human Factor IX were found 24–72 h after transfection in either mode of DNA delivery to the myoblasts. However, at 96 h after transfection a significant increase in Factor IX was observed in cells transfected with the $CAPO_4$ procedure (naked DNA 0.29 ng/100 μl, DNA:$CaPO_4$ 1.83 ng/100 μl). Factor IX levels in this group increased further at 120 h (naked DNA 0.96 ng/100 μl, DNA:$CaPO_4$ 6.08 ng/100 μl) and then declined to the basal level at 130 h. No detectable Factor IX was found in cells transfected with DNA formulated in lipofectin. These data suggest that the human factor IX gene construct (SK-F.IX-SK) can be expression in $C_2Cl_2$ myoblasts.

TABLE V

ELISA Detection of Factor IX in Cultured Myotubes

| | Expression time (h) | | | | | |
|---|---|---|---|---|---|---|
| | 24 | 40 | 72 | 96 | 120 | 136 |
| | Human Factor IX (ng/100 μl) | | | | | |
| Naked DNA | 0.0 | 0.0 | 0.2 | 0.3 | 1.0 | 0.0 |
| DNA:$CaPO_4$ | 0.2 | 0.0 | 0.0 | 1.8 | 6.1 | 0.0 |
| Lipofectin | 0.2 | 0.1 | 0.1 | 0.3 | 2.2 | 1.3 |
| DNA:Lipofectin (1:7) | 0.4 | 0.2 | 0.0 | 0.2 | 0.0 | 2.5 |

Enhanced Vector Expression in Intact Muscle

Intact plasmid DNA in a sterile 20% sucrose solution (wt/vol) can be injected into mature avian or mammalian muscle. Following a single injection the vector DNA is stable for at least 30 days as a non-integrated extrachromosomal circular DNA in muscle nuclei and, is transcriptionally active. Wolf et al., Science, vol. 247, pp. 1465–1468 (1990). However, greater than 99% of the injected DNA is degraded in muscle under the Wolff protocol (Wolff, et al, BioTechniques, vol. 11, pp. 4374–485, (1991)). This protocol can be improved by increasing the uptake of plasmid DNA into muscle and reducing vector degradation. The procedure of the present invention uses expression vector DNA coated with the relevant transcriptional regulatory factors, the human serum response factor and other human associated nuclear proteins, such as histone, and transcription initiation factors to enhance uptake and stability. The regulatory proteins protect the DNA against muscle nucleases and facilitate the uptake of the protein coated DNA into myogenic nuclei.

The expression vector forms a protein/DNA complex by the sequence specific binding of the serum response factor with the inner core CCXXXXXXGG (where X can be either A or T; Sequence I.D. No. 5) of the serum response element and by the addition of histone. The interaction with the inner core of the promoter facilitates myogenic cell type restricted expression of the skeletal a-actin gene. The serum response factor, transcription initiation factor, transregulatory factor and histones are added to the expression vector by an in vitro binding reaction to form a reconstituted protein/DNA complex.

Coating the Expression Vector System

A specific formulation involves coating the vector with elements of the transcription initiation complex and histone. This formulation is used both to enhance delivery of the vector to the cell and to enhance expression of the vector within the cell.

The following protocol was used to bacterially express and purify human serum response factor (SRF). Plasmid pARSRF-Nde is a T7 polymerase vector (Studier, F. W. and Moffatt, J. Mol. Biol., vol. 189, pp 113–130 (1986)) which produced full-length SRF protein upon IPTG (isopropyl-B-D-thiogalactopyranoside) induction. (Manak et al., Genes and Development vol. 4, pp. 955–967 (1990)). E. coli BL21 harboring the plasmid was grown at 37° C. to an $OD_{600}$ of 0.4 in TYP medium supplemented with ampicillin (50 μg/ml). Synthesis of SRF was then induced with 1 mM IPTG for 2.0 hr, after which cells were spun down, washed once in TE buffer (10 mM Tris-HCl, 1 mM EDTA, pH 7.0) and resuspended in a 40× packed cell volume and dialyzed against (10 mM HEPES [N-2 hydroxyethylpiperzine-N-2-ethansulfonic acid, pH 7.4], 60 mM KCl, 1 mM 2-mercaptoethanol 0.5 mM EDTA, 0.5 mM phenylmethylsulfonyl fluoride and 10% glycerol). Cells were disrupted on ice by sonication. The lysate was clarified by centrifugation (15,000×g for 20 min.) and the high speed supernatant containing overexpressed SRF was stored at −80° C. Partial purification of SRF was done as follows. A 10 ml amount of the lysate was applied to a 10 ml phosphocellulose column equilibrated with column buffer (same as dialysis buffer as described above) and 0.05% Nonidet P-40. The flow through fractions were collected and applied to a 5-ml heparin agarose column. The column was washed with 0.35M KCl and SRF was eluted with 0.5M KCl. SRF was then dialyzed and stored at −80° C.

Approximately, a ratio by weight of 5 to 1 SRF protein to expression vector DNA was allowed to incubate together in a solution containing 10 mM. Tris-HCl (pH 8.0, 0.1 mM EDTA, 2 mM dithiothreitol, 5% glycerol plus 100 mM KCl. The binding of SRF to the actin promoter has been verified by DNA binding assays and by nuclease footprint protection assays as shown in the art. Transcription initiation factors such as the TATA box protein (TBP) and other initiation factors such as TFIIB, E and F are eluted from purified HeLa cell nuclei by the protocol of Dignam et al., *Mol. Cell. Biol.*, vol. 10, pp. 582–598 (1983) with 0.42M KCl in the above dialysis buffer. Nuclear lysates containing transcription initiation factors are mixed together with the SRF-DNA plasmid at a ratio of 10 parts protein to one part SRF-DNA to help form a preinitiation complex which is dialyzed for 24 hours. Finally, a crude histone preparation which is stripped from HeLa nuclei in 6M urea, 2M NaCl is dialyzed against low salt dialysis buffer. The full complement of histone are slowly added to a final ratio of 1 to 1 (histone to the SRF-protein DNA complex) to form nucleosome particles over nonprotected DNA. The addition of histone will protect regions of DNA to a greater extent than naked DNA from cellular nucleases.

The nucleoprotein complex is then further formulated with a lipid base, nonaqueous base and/or liposomes for direct injection into muscle. Because of the abundance of specific transcription factors, which contain nuclear targeting sequences, expression vector DNA is readily delivered, and taken up into muscle nuclei. The expression vector can also be delivered as described below.

Figure 11:
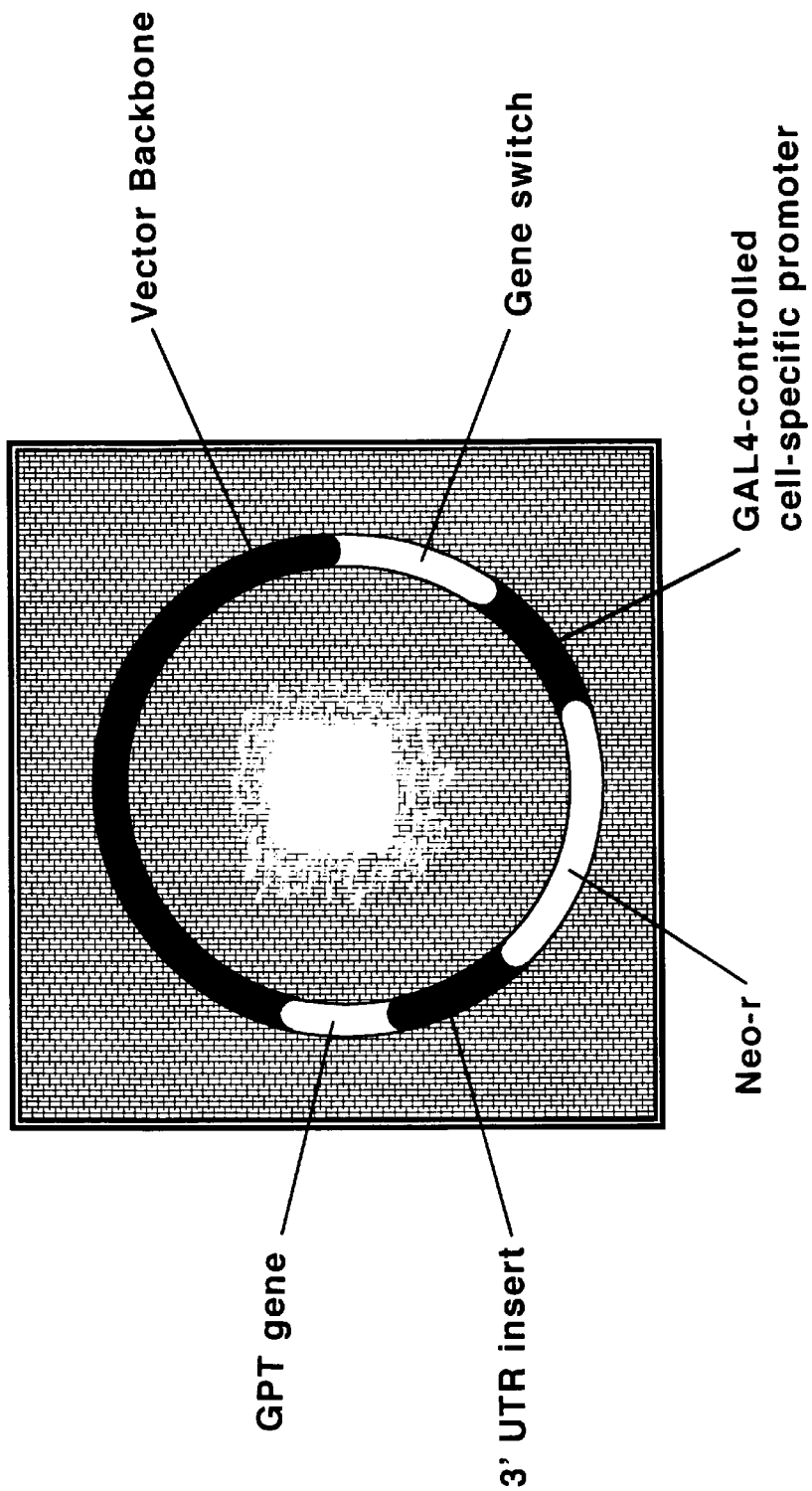
FIG. 11 shows a diagrammatic representation of a plasmid used to screen for tissue-specific 3'UTR sequences.

Selection of 3' Flanking Regions that Demonstrate Tissue-Specific Enhancement of mRNA Stability in Liver or other Cells Selection of 3' flanking regions, which incorporate 3'UTR and/or 3'NCR, from particular tissues, including liver, can be achieved through screening of 3' ends of DNA libraries using a plasmid designed to impart neomycin resistance to cells only when neo-r transcripts are stabilized for an extended period. The screening plasmid contains the following elements orientated as depicted in FIG. 11. Constituitively expressed from the plasmid is the mutant steroid receptor described in the patent application U.S. Ser. No. 07/939246 by Vegeto et al., entitled "Mutated Steroid Hormone Receptors, Methods for Their Use and Molecular Switch for Gene Therapy" all of which (including drawings) is hereby incorporated by reference herein, and the selectable gene guanine phosphoribosyl-transferase (GPT). In another position in the plasmid is the steroid responsive, GAL4 sequence, linked to a tissue-specific promoter that drives transcription of the neomycin resistance gene that is modified at the 3' end to have a cloning site for the 3' flanking region library sequences. Specifically, for selection of liver specific 3' flanking region sequences, the α-1-antitrypsin promoter is used to drive the neomycin resistance gene and the 3' flanking region sequences will be selected for in HPRT⁻ HepG2 cells.

Tissue specific 3' flanking region sequences derived from DNA libraries and sequences between 50 and 2000 base pairs are cloned into the cloning site of the plasmid to generate test plasmids. Test plasmids are than transfected into the cell type of desire using the $CAPO_4$ method as known in the art. For liver specific sequences the cell type is HepG2. Initial screening for the cells that have been transfected is in medium containing $5 \times 10^{-4}$M hypoxanthine, $4 \times 10^{-6}$M aminopterin and $5 \times 10^{-5}$M thymidine (HAT media). Non-transfected cells are killed in this medium leaving only the transfected cells. To select for the ability of the library fragments to establish RNA with an extended half-life the transfected cells are initially treated with 0.1 $\mu$M RU486 for 6 hrs. RU486 treatment will induce expression from the GAL4-linked promoter of the neomycin resistance gene. 60 hrs after the RU486 treatment the cells are treated with medium containing 2 mg/m of G418 for 24 hr. Only those cells that have sufficiently long-lived mRNA producing the neomycin resistance product will survive this selection procedure.

The plasmids that are recovered from the selected cell population are analyzed as to the nature of the 3' flanking regions and confirmed in additional studies of RNA half life by methods known in the art. While the example given here is for liver cells one skilled in the art will easily recognize that any cell type may be substituted in order to obtain tissue-specific 3' flanking regions which stabilize mRNA. In addition, point mutations, deletions or insertions to the 3' flanking regions are acceptable in order to modify the 3' flanking region but still retain or enhance the MRNA stability activity.

Administration

Administration as used herein refers to the route of introduction of a vector or carrier of DNA into the body. Administration can be directly to a target tissue or by targeted delivery to the target tissue after systemic administration. In particular, the present invention can be used for treating disease by administration of the vector to the body in order to establishing controlled expression of any specific nucleic acid sequence within tissues at certain levels that are useful for gene therapy.

The preferred means for administration of vector and use of formulations for delivery are described above. The preferred embodiment is by direct injection using needle injection or hypospray.

The route of administration of any selected vector construct will depend on the particular use for the expression vectors. In general, a specific formulation for each vector construct used will focus on vector uptake with regard to the particular targeted tissue, followed by demonstration of efficacy. Uptake studies will include uptake assays to evaluate cellular uptake of the vectors and expression of the tissue specific DNA of choice. Such assays will also determine the localization of the target DNA after uptake, and establishing the requirements for maintenance of steady-state concentrations of expressed protein. Efficacy and cytotoxicity can then be tested. Toxicity will not only include cell viability but also cell function.

Muscle cells have the unique ability to take up DNA from the extracellular space after simple injection of DNA particles as a solution, suspension, or colloid into the muscle. Expression of DNA by this method can be sustained for several months.

Delivery of formulated DNA vectors involves incorporating DNA into macromolecular complexes that undergo endocytosis by the target cell. Such complexes may include lipids, proteins, carbohydrates, synthetic organic compounds, or inorganic compounds. The characteristics of the complex formed with the vector (size, charge, surface characteristics, composition) determines the bioavailability of the vector within the body. Other elements of the formulation function as ligand which interact with specific receptors on the surface or interior of the cell. Other elements of the formulation function to enhance entry into the cell, release from the endosome, and entry into the nucleus.

Delivery can also be through use of DNA transporters. DNA transporters refers to molecules which bind to DNA vectors and are capable of being taken up by epidermal cells. DNA transporters contain a molecular complex capable of noncovalently binding to DNA and efficiently transporting the DNA through the cell membrane. It is preferable that the transporter also transport the DNA through the nuclear membrane. See, e.g., the following applications all of which (including drawings) are hereby incorporated by reference herein: (1) Woo et al., U.S. Ser. No. 07/855,389, entitled "A DNA Transporter System and Method of Use," filed Mar. 20, 1992; (2) Woo et al., PCT/US93/02725, entitled "A DNA Transporter System and method of Use", (designating the U.S. and other countries) filed Mar. 19, 1993; (3) continuation-in-part application by Woo et al., entitled "Nucleic Acid Transporter Systems and Methods of Use", filed Dec. 14, 1993, assigned attorney docket number 205/012 but not yet assigned a U.S. Ser. No.; (4) Szoka et al., U.S. Ser. No. 07/913,669, entitled "Self-Assembling Polynucleotide Delivery System", filed Jul. 14, 1992 and (5) Szoka et al., PCT/US93/03406, entitled "Self-Assembling Polynucleotide Delivery System", (designating the U.S. and other countries) filed Apr. 5, 1993.

Transfer of genes directly into muscle has been very effective. Experiments show that administration by direct injection of DNA into muscle cells results in expression of the gene in the area of injection. Injection of plasmids containing IGF-I results in expression of the gene for months at relatively constant levels. The injected DNA appears to persist in an unintegrated extrachromosomal state. This means of transfer is the preferred embodiment.

Another preferred method of delivery involves a DNA transporter system. The DNA transporter system consists of particles containing several elements that are independently and non-covalently bound to DNA. Each element consists of a ligand which recognizes specific receptors or other functional groups such as a protein complexed with a cationic group that binds to DNA. Examples of cations which may be used are spermine, spermine derivatives, histone, cationic peptides and/or polylysine. one element is capable of binding both to the DNA vector and to a cell surface receptor on the target cell. Examples of such elements are organic compounds which interact with the asialoglycoprotein receptor, the folate receptor, the mannose-6-phosphate receptor, or the carnitine receptor. A second element is capable of binding both to the DNA vector and to a receptor on the nuclear membrane. The nuclear ligand is capable of recognizing and transporting a transporter system through a nuclear membrane. An example of such ligand is the nuclear targeting sequence from SV40 large T antigen or histone. A third element is capable of binding to both the DNA vector and to elements which induce episomal lysis. Examples include inactivated virus particles such as adenovirus, peptides related to influenza virus hemagglutinin, or the GALA peptide described in the Skoka patent cited above.

Administration may also involve lipids. The lipids may form liposomes which are hollow spherical vesicles composed of lipids arranged in unilamellar, bilamellar, or multilamellar fashion and an internal aqueous space for entrapping water soluble compounds, such as DNA, ranging in size from 0.05 to several microns in diameter. Lipids may be useful without forming liposomes. Specific examples include the use of cationic lipids and complexes containing DOPE which interact with DNA and with the membrane of the target cell to facilitate entry of DNA into the cell.

Gene delivery can also be performed by transplanting genetically engineered cells. For example, immature muscle cells called myoblasts may be used to carry genes into the muscle fibers. Myoblast genetically engineered to express recombinant human growth hormone can secrete the growth hormone into the animal's blood. Secretion of the incorporated gene can be sustained over periods up to 3 months.

Myoblasts eventually differentiate and fuse to existing muscle tissue. Because the cell is incorporated into an existing structure, it is not just tolerated but nurtured. Myoblasts can easily be obtained by taking muscle tissue from an individual who needs gene therapy and the genetically engineered cells can also be easily put back with out causing damage to the patient Is muscle. Similarly, keratinocytes may be used to delivery genes to tissues. Large numbers of keratinocytes can be generated by cultivation of a small biopsy. The cultures can be prepared as stratified sheets and when grafted to humans, generate epidermis which continues to improve in histotypic quality over many years. The keratinocytes are genetically engineered while in culture by transfecting the keratinocytes with the appropriate vector. Although keratinocytes are separated from the circulation by the basement membrane dividing the epidermis from the dermis, human keratinocytes secrete into circulation the protein produced.

Delivery may also involve the use of viral vectors. For example, an adenoviral vector may be constructed by replacing the E1 region of the virus genome with the vector elements described in this invention including promoter, 3'UTR, 3'UTR and nucleic acid cassette and introducing this recombinant genome into 293 cells which will package this gene into an infectious virus particle. Virus from this cell may then be used to infect tissue ex vivo or in vivo to introduce the vector into tissues leading to expression of the gene in the nucleic acid cassette.

The chosen method of delivery should result in expression of the gene product encoded within the nucleic acid cassette at levels which exert an appropriate biological effect. The rate of expression will depend upon the disease, the pharmacokinetics of the vector and gene product, and the route of administration, but should be between 1–1000 mg/kg of body weight/day. This level is readily determinable by standard methods. It could be more or less depending on the optimal dosing. The duration of treatment will extend through the course of the disease symptoms, possibly continuously. The number of doses will depend upon disease delivery vehicle and efficacy data from clinical trials.

Cell Transfection and Transformation

One embodiment of the present invention includes cells transfected with the vectors described above. Once the cells are transfected, the transformed cells will express the protein or RNA encoded for by the nucleic acid cassette. Examples of proteins include, but are not limited to poly- peptide, glycoprotein, lipoprotein, phosphoprotein, or nucleoprotein. The nucleic acid cassette which contains the genetic material of interest is positionally and sequentially oriented within the vectors such that the nucleic acid in the cassette can be transcribed into RNA and, when necessary, be translated into proteins or polypeptides in the transformed cells.

A variety of proteins can be expressed by the sequence in the nucleic acid cassette in the transformed epidermal cells.

Those proteins which can be expressed may be located in the cytoplasm, nucleus, membranes (including the plasmalemma, nuclear membrane, endoplasmic reticulum or other internal membrane compartments), in organelles (including the mitochondria, peroxisome, lysosome, endosome or other organelles), or secreted. Those proteins may function as intracellular or extracellular structural elements, ligand, hormones, neurotransmitter, growth regulating factors, differentiation factors, gene-expression regulating factors, DNA-associated proteins, enzymes, serum proteins, receptors, carriers for small molecular weight organic or inorganic compounds, drugs, immunomodulators, oncogenes, tumor suppressor, toxins, tumor antigens, or antigens. These proteins may have a natural sequence or a mutated sequence to enhance, inhibit, regulate, or eliminate their biological activity. Specific examples of proteins to be expressed include those described above in reference to the term nucleic acid cassette.

In addition, the nucleic acid cassette can code for RNA. The RNA may function as a template for translation, as an antisense inhibitor of gene expression, as a triple-strand forming inhibitor of gene expression, as an enzyme (ribozyme) or as a ligand recognizing specific structural determinants on cellular structures for the purpose of modifying their activity. Specific examples include RNA molecules to inhibit the expression or function of prostaglandin synthase, lipooxenganse, histocompatibilty antigens (class I or class II), cell adhesion molecules, nitrous oxide synthase, $\beta_2$ microglobulin, oncogenes, and growth factors.

The compounds which can be incorporated are only limited by the availability of the nucleic acid sequence for the protein or polypeptide to be incorporated. One skilled in the art will readily recognize that as more proteins and polypeptides become identified they can be integrated into the vector system of the present invention and expressed in animal or human tissue.

Transfection can be done either by in vivo or ex vivo techniques. For example, muscle cells can be propagated in culture, transfected with the transforming gene, and then transplanted into muscle tissue. Alternatively, the vectors can be administered to the cells by the methods discussed above.

Regulatable Expression Vector System

Figure 13:
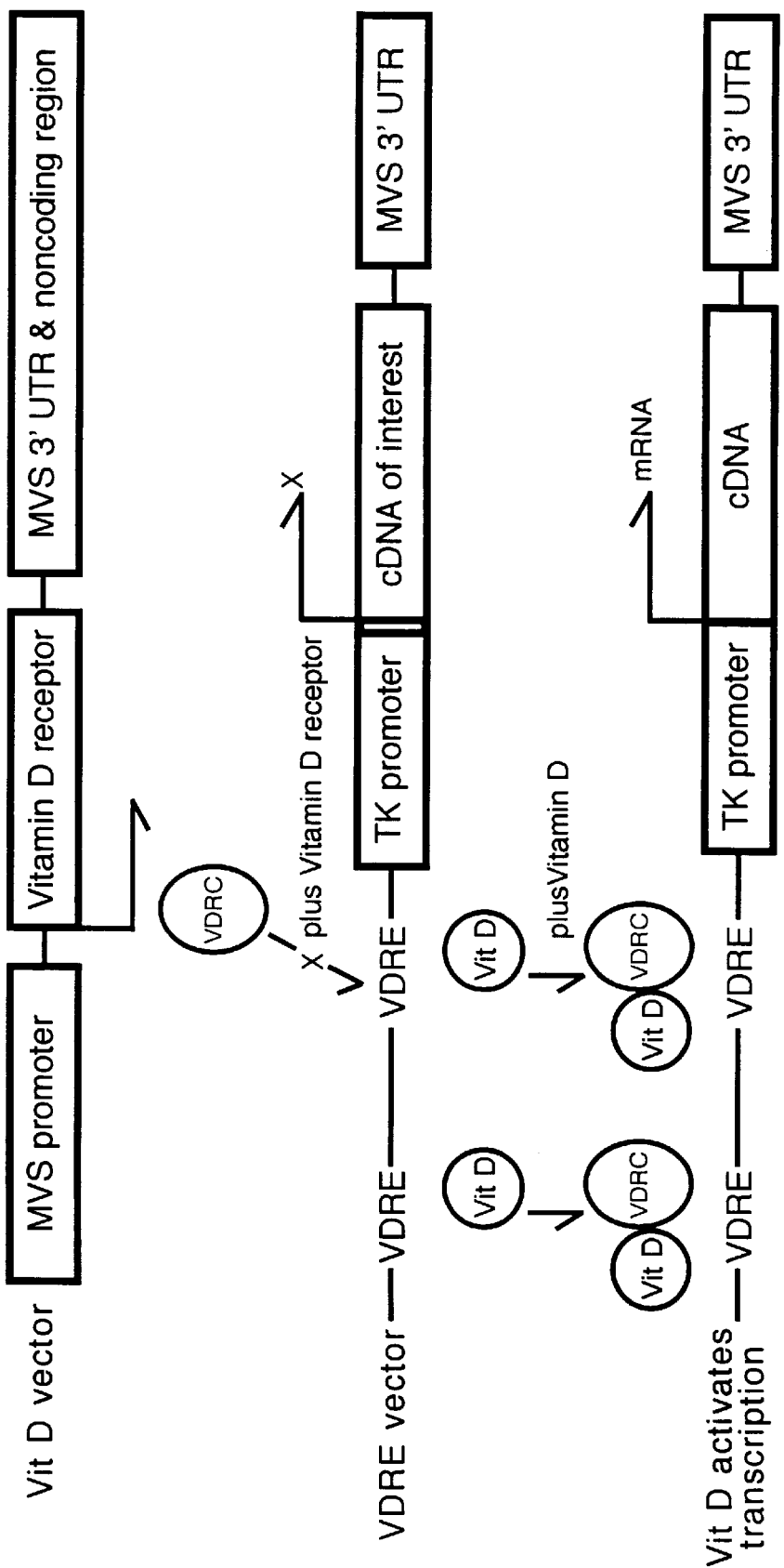
FIG. 13 is a schematic representation of a regulatable vector system using a chimeric receptor.

Under certain circumstances, it is desirable to control the vector's transcriptional activity over time and to switch gene transcription on and off. It may also be important that the regulation of the expression vector be controlled by natural inducer products that are neither considered toxic to humans nor are immunogenic. Two nonrestricting examples of different Vitamin D regulatory systems are shown in FIGS. 12 and 13.

The cellular concentration of Vitamin D receptor (VDR) in muscle can be increased through the expression vector by injecting a hybrid skeletal actin VDR gene that would be under control of the actin promoter and the 3'UTR stabilizing sequences. The target, SEQ. ID. No. 2, is constructed to contain synthesized multimers of the Vitamin D regulatory element (VDRE). This target is linked to a minimal Herpes Simplex Virus (HSV) thymidine kinase promoter. Transcriptional activity emanating from the TK promoter is regulated by the presence of VDR and coactivated by the ligand, Vitamin D. Any polypeptide sequence cloned in tandem to the HSV promoter, as a cDNA, is driven from the target vector when Vitamin D is introduced into the muscle cells. The hybrid actin VDR gene and the target vector are linked on the same plasmid or coinjected on separate plasmids. Premeasured levels of Vitamin D are administered by drinking a glass of milk or taking a Vitamin D pill. The levels are used to activate transcription of the target vector. Taking the ligand on every other day, will oscillate the promoter activity. Removal of the ligand, Vitamin D, from the diet down regulates or represses transcription from the target vector. One skilled in the art will recognize that other receptors and binding domains can be used.

Methods of Use

Treatment with Growth Hormone

Growth hormone is normally produced and secreted from the anterior pituitary and promotes linear growth in prepuberty children. Growth hormone acts on the liver and other tissues to stimulate the production of insulin like growth factor I. This factor is, in turn, responsible for the growth promoting effects of growth hormone. Further, this factor serves as an indicator of overall growth hormone secretion. Serum IGF-I concentration increases in response to endogenous and erogenous administered growth hormone. These concentrations are low in growth hormone deficiency. Insulin-like growth factors are one of the key factors that potentiate muscle development and muscle growth. Myoblasts naturally secrete IGF-I/IGF-II as well as its cognate binding proteins during the onset of fusion. This process coincides with the appearance of muscle specific gene products. In terminally differentiated muscle, signals propagated from passive stretch induced hypertrophy induce the expression of IGF genes. Many of the actions of IGFs on muscle result from interactions with the IGF-I receptor. The intramuscular injection of an expression vector containing the sequence for IGF-I (for example SK 733 IGF-I Sk2, i.e., pIG0100A or pIG0335) can be used to treat growth disorders. Vectors are designed to control the expression of IGF-I in a range of 100–400 ng/ml. Since intramuscular expression of vectors leads to expression of the product encoded by the nucleic acid cassette for several months, this method provides a long-term inexpensive way to increase systemic blood concentration of IGF-I in patients with growth hormone deficiency.

Treatment of Dystrophic Muscle Disease

Muscular dystrophies are among the most frequent of inherited genetic disorders. Muscular dystrophies are usually not immediately fatal but develop progressively. Molecular genetic analysis has identified mutations in at least a dozen genes that alone or in combination result in muscular dystrophic symptoms. Presently there is no effective cure for these diseases and therapy is devoted to management of acute symptoms. Expression of the non-mutated counterpart of these genes in the muscle cells of patients with muscular dystrophy alleviates some of the debilitating symptoms.

The expression vector of the present invention is ideally suited for the treatment of muscle disorders including almost all forms of muscular dystrophy. The present vector system will be able to express high levels of the following genes specifically in muscle tissue; the full length Duchenne's muscular dystrophy gene (dystrophin), the related sequence of the gene responsible for Becker's muscular dystrophy; myotonin protein kinase; alpha-subunit of $Na^+$ channels; the 50 kd-dystrophyn associated glycoprotein; myophosphorylase; phosphofructokinase; acid maltase; glycogen debranching enzyme; phosphoglycerate kinase; phosphoglycerol mutase; lactate dehydrogenase; and carnitine palmitoyl transferase. The appropriate gene for the particular afflicted individual can be determined through genetic screening as known in the art.

Administration of the vectors can be intravenously, through direct injection into the muscle or by any one of the methods described above. Dosages will depend on the severity of the disease and the amount of dosage is readily determinable by standard methods. The duration of treatment will extend through the course of the disease symptoms which can be continuously.

Treatment of Muscle Atrophy Due To Age

Growth hormone levels decline with increasing age. The levels in healthy men and women above age of 55 are approximately one third lower than the levels in men and women 18 to 33. This is associated with a decrease in the concentration of IGF-I. The decline in growth hormone and IGF-I production correlate with the decrease in muscle mass, termed senile muscle atrophy, and increase in adiposity that occur in healthy human subjects. Administering growth hormone three times a week to healthy 61 to 81 year old men who had serum levels below those of healthy younger men increased the serum IGF-I levels to within the range found in young healthy adults. This increase level led to increased muscle mass and strength and reduced body fat. The secretion of growth hormone is regulated by a stimulatory (growth hormone releasing hormone) and an inhibitory (somatostatin) hypothalamic hormone.

The convenient cloning sites in the expression vectors of the present invention are used to construct vectors containing human growth hormone CDNA sequence, the human growth hormone releasing hormone (GHRH), or IGF-I. This versatility is important since the GHRH, GH, and IGF-I, while having equivalent desired effects on muscle mass, may have different side effects or kinetics which will affect their efficacy. The expression of the growth factor releasing hormone might be more advantageous than the expression of either IGF-I or the growth hormone vectors transcripts. Since GHRH is reduced in the elderly it appears to be responsible for the lack of GH secretion rather than the anterior pituitary capability of synthesizing growth hormone, thus the increased expression of GHRH from muscle would increase GHRH levels in the systemic blood system and can allow for the natural diurnal secretion pattern of GH from the anterior pituitary. In this way, GHRH could act as the natural secretogogue, allowing for elevated secretion or release of GH from the hypothalamus of the elderly.

Thus, the application of vector systems described herein to express insulin-like growth factors through the injection of the SK 733 IGF-I Sk2 vector, vectors expressing HG, or GHRH into adult muscle of the elderly is a long-term inexpensive way to increase systemic blood concentration of IGF-I in the elderly.

Administration of the vectors can be intravenously, through direct injection into the muscle or by any one of the methods described above. Dosages will depend on the severity of the disease and the amount of dosage is readily determinable by standard methods. The duration of treatment will extend through the course of the disease symptoms which can be continuously.

Treatment of Human Muscle Atrophies Induced by Neurological Dysfunction

Insulin-like growth factors are also known neuro-trophic agents which maintain neuronal muscular synapses, neuron integrity, and neuronal cell life under neuro-degenerative conditions. Since the expression vector driven genes are relatively insensitive to the innervation state of the muscle, they provide a direct and rather broad application for remedying certain kinds of human muscle atrophies caused by spinal cord injuries and neuromuscular diseases caused by drugs, diabetes, Type I disease, Type II diabetes, genetic diseases such as CHACOT-marie-tooth disease or certain other diseases. Moreover, IGF-I secretion can induce neurite outgrowth. In this treatment, the product of the vector acts as a neurotrophic agent secreted from injected muscle and as a hypertrophic agent to maintain muscle integrity.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously.

Treatment of Atherosclerotic Cardiovascular Diseases

Atherosclerotic cardiovascular disease is a major cause of mortality in the United States and the world. The atherosclerotic plaque, the basic underlying lesion in atherosclerosis, contains cholesterol esters that are derived from circulating lipids. These circulating lipids are essential to the development of atherosclerosis. The plasma concentration of high density lipoprotein (HDL) is inversely related to the propensity for developing atherosclerosis. In the nascent state, HDL is secreted in the form of discoidal particles. These particles consist of a bilayer of phospholipids onto which the apolipoproteins (ApoA-I, ApoII and E) are embedded. HDL captures cholesterol esters by the action of an enzyme, lecithin-cholesterol acyltransferase. HDL is secreted from the liver, the small intestine and possibly other tissues.

The ApoA-I cDNA is 878 bp and encodes 267 amino acids, including the 24 amino acid propeptide. Increasing the circulating levels of HDL can influence or reverse cholesterol transport, and thus reduce the propensity for forming atherosclerotic plaques. The insertion of the human ApoA-I coding sequences into the expression vector serves as an expression vector for enhanced ApoA-I expression following injection of plasmid DNA into skeletal muscle. The expression vector ApoA-I hybrid gene is effective for long term expression, biosynthesis and secretion of HDL in an ectopic site, and thus increases the content of total secretable HDL in blood plasma.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously. Alternatively, treatment of atherosclerotic cardiovascular disease can also be treated by inserting the very low density lipoprotein (VLDL) receptor gene into the above-described vectors. VLDL has been described in Chan, Ser. No. 08/149,103 entitled "Human and Mouse Very Low Density Lipoprotein Receptors and Methods for Use of Such 0 Receptors," filed Nov. 08, 1993 hereby incorporated by reference (including drawings).

Treatment of Diabetes

Insulin plays a central role in the regulation of carbohydrate, fat and protein metabolism. With diabetics, treatment with insulin can result in insulin resistance in which insulin treatment will not result in adequate metabolic control. This resistance can occur in the presence of circulating insulin or insulin-receptor antibodies or insulin-receptor abnormalities or episodically in patients with previously typical insulin-dependent diabetes mellitus. Therapeutic options are limited with patients suffering from severe insulin resistance.

IGF-I can be used in the treatment of insulin resistance. Treatment with IGF-I using the vectors of the present invention will achieve glycemic control by reversing hyperglycemia and ketoacidosis. Treatment with IGF-I will also improve the degree of insulin sensitivity. The convenient cloning sites in the expression vectors of the present invention are used to construct vectors containing the IGF-I CDNA sequence. Expression of IGF-I provides insulin like metabolic effects. IGF-I shares sequence homology and biological properties with insulin.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously.

Treatment of Peripheral Neuropathies

Peripheral neuropathies are degenerative processes of sensory and motor nerves that often result from diabetes, Type I diabetes, Type II diabetes, genetic disease such as CHACOT-marie-tooth disease, AIDS, inflammation and side-effects from anti-cancer and anti-viral drugs. Current treatment is limited to pain management, with no treatment directed at the underlying cellular causes. Use of recombinant IGF-I has been suggested to restore some of the degenerative processes in peripheral neuropathies and to alleviate some of the associated dysfunction.

Administration of a vector encoding IGF-I to localized muscles afflicted with peripheral neuropathy by direct injection or hypospray will aid in the regeneration of neurons, decrease pain sensations, and increase mobility of the affected site. The distinct advantage of vector administration of IGF-I is increased levels at needed sites with reduced numbers of administrations. In the diabetic patient dosage schedules may allow for the combined effect of alleviation of symptoms of peripheral neuropathy and increased efficiency of insulin.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously.

Treatment of Osteoporosis

Osteoporosis is a common accelerated loss of bone mass that often accompanies aging. The decreased bone density associated with osteoporosis leads to an increased susceptibility to bone fractures. Treatment with IGF-I is associated with increased bone density. Administration of a vector encoding IGF-I to muscles by direct injection or hypospray will aid in the redeposition of bone and thereby decrease the risk of fractures.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously.

Treatment of Hemophilia

As described above vector constructs containing human Factor IX have been produced that effectively secrete Factor IX into the culture media of transfected tissue culture cells. Factor IX levels achievable in these tissue culture supernatant suggest that adequate Factor IX can be produced in muscle cells in vivo to achieve a therapeutic level of authentic Factor IX in individuals suffering from hemophilia B. Factor IX containing MVS constructs can be administered to hemophiliacs by either direct muscle injection or hypospray. Sufficient Factor IX can then be synthesized in vivo to restore clotting times to within normal ranges. By constructing a MVS vector that contains the factor VIII gene or an active portion of the gene treatment for hemophilia A can be achieved by a similar method.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously.

Treatment of Anemia

An additional embodiment of the present invention is a method for the treatment of anemia. The vectors of the present invention are well suited to express hematologic factors such as erythropoietin (EPO). Following direct injection or hypospray administration of a vector encoding EPO, muscle cells begin to secrete EPO into the circulation where it can increase the production of red blood cells. This therapy is particularity suited for the treatment of anemia associated with chronic systemic disease such as inflammation, renal disease, endocrine failure and liver failure. The EPO vector construct has particular advantages over the convention administration of recombinant EPO in that the frequency of administration for will be reduced from the current three times per day to approximately once per month, depending on the severity of anemia. The doing frequency can easily be adjusted so as to maintain the patients hematocrit between 0.33 and 0.38.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously.

Immune Responses

An additional embodiment of the present invention is a method for producing an immunological response. The expression vector systems of the present invention are well suited for directing the expression of an exogenous protein epitope in muscle and other tissues, and thus, for generating vaccines in humans and animals. Targeted sequences are inserted into the cassette of a vector for expression of protein epitopes for mediating protective immunization. For example, the constant regions of proteins of HIV subtypes, GP 120, GP 160 and/or GP 41 and for cell mediated immunity GP 24, reverse transcriptase, Cytomegalovirus, Respiratory Syncytial Virus, Influenza Virus, Hepatitis Virus (A,B,C,D), as well pneumococcus, meningococcus, streptococcus, staphylococcus, heat stable enterotoxins, heat labile enterotoxins, pneumocystitis, the pathogen of lyme disease, aspergillus, candida, and malaria. One skilled in the art will readily recognize that any other variety of proteins can be used to generate immunologic response and thus produce antibodies for vaccination. The expression vector is then injected into the human or animal allowing an immune response to occur. Significantly, the in vivo expression of these antigens in conjunction with class I and other immunoregulatory proteins can lead to improved immunity characterized by long term persistence with memory T-cells and cellular immune responses in addition to an antibody response.

Administration of the vectors can be intravenously, through direct injection or by any one of the methods described above. Dosages will depend on the severity of the disease and the amount of dosage is readily determinable by standard methods. The duration of treatment will extend through the course of the disease symptoms which can be continuously.

Transgenic Swine

An additional embodiment of the present invention is the 5 generation of improved domestic livestock. Specifically, introduction of the vector SK733IGF-I-3'SK2, or a vector expressing IGF-I of porcine, bovine or ovine derivation into oocytes of domestic swine by the method described above for the generation of transgenic mice will generate swine expressing IGF-I in myogenic tissue. These transgenic swine have the desired livestock characteristics of increased muscle mass and reduced fat.

In addition, by providing contiguous 3' NCR, IGF-I is buffered against outside genomic sequences and is thus more protected from position effects, when integrated into the genome. In addition, by providing natural terminating sequences, the additional regulatory sequences that mark the transcriptional domain of skeletal α-actin prevent read through transcription, improve tissue specificity, developmental timing and transcriptional activity. Presence of 3'NCR sequence allows for a single copy of the integrated vector to produce 40–50% of the transcriptional activity of the endogenous sequences.

Improvement of Livestock

An additional embodiment of the present invention is the improvement of livestock by injection of species-specific MSV-IGF-I constructs. Muscle injection of vectors encoding IGF-I by hypodermic or hypospray administration will promote increased muscle mass and reduced body fat in important livestock species such as cattle, sheep, swine, rabbits, deer, fish and birds such as turkeys, chickens, ducks, and geese. Administration of the vectors cal also be through any one of the methods described above.

One skilled in the art will readily appreciate that the present invention is well adapted to carry out the objects and obtain the ends and advantages mentioned as well as those inherent therein. The vector systems along with the methods, procedures treatments and vaccinations described herein are presently representative of preferred embodiments are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein within departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

SEQUENCE LISTING (1) GENERAL INFORMATION:

(iii) NUMBER OF SEQUENCES: 8

(2) INFORMATION FOR SEQ ID NO: 1:

(i) SEQUENCE CHARACTERISTICS:
      (A) LENGTH: 275 bases
      (B) TYPE: nucleic acid
      (C) STRANDEDNESS: single
      (D) TOPOLOGY: linear (ii) MOLECULE TYPE: cDNA (iii) SEQUENCE DESCRIPTION: SEQ ID NO: 1:

```
TAAACATGTT TACATGATCA CTTTGCCAAC CACACTCAGG ATGACAATCT TGTAGGTTCC      60

AGGCTGCTGA GGACCTGCAC CAGCCATGCA ACTTTCTATT TTGTAACAAT TTCTGGTTAC     120

TGTTGCTGCA AAGCCCATGT GACACAGTGT ATGTAAAGTG TACATAAATT AATTTATTTT     180

ACCTCGTTTT GTTTGTTTTT AAAACCAATG CCCTGTGGAA GGAAACATAA AACTTCAAGA     240

AGCATTAAAT CATCAGTCAT TCTGTCACAC CCCTA                                275
```

(2) INFORMATION FOR SEQ ID NO: 2:

(i) SEQUENCE CHARACTERISTICS:
        (A) LENGTH:           27 bases
        (B) TYPE:             nucleic acid
        (C) STRANDEDNESS:    single
        (D) TOPOLOGY:        linear (ii) MOLECULE TYPE:        cDNA (iii) SEQUENCE DESCRIPTION: SEQ ID NO: 2:

GGTGACTCAC CGGGTGAACG GGGCATT                                    27

(2) INFORMATION FOR SEQ ID NO: 3:

(i) SEQUENCE CHARACTERISTICS:
        (A) LENGTH:           14 bases
        (B) TYPE:             nucleic acid
        (C) STRANDEDNESS:    single
        (D) TOPOLOGY:        linear (ii) MOLECULE TYPE:        cDNA (iii) SEQUENCE DESCRIPTION: SEQ ID NO: 3:

GAGGACGTCC CCAG                                                          14

(2) INFORMATION FOR SEQ ID NO: 4:

(i) SEQUENCE CHARACTERISTICS:
        (A) LENGTH:           18 bases
        (B) TYPE:             nucleic acid
        (C) STRANDEDNESS:    single
        (D) TOPOLOGY:        linear (ii) MOLECULE TYPE:        cDNA (iii) SEQUENCE DESCRIPTION: SEQ ID NO: 4:

GTCATTTAGG GACAACAG                                                 18

(2) INFORMATION FOR SEQ ID NO: 5:

(i) SEQUENCE CHARACTERISTICS:
        (A) LENGTH:           10 bases
        (B) TYPE:             nucleic acid
        (C) STRANDEDNESS:    single
        (D) TOPOLOGY:        linear (ii) MOLECULE TYPE:        cDNA (iii) FEATURE:
        (A) OTHER INFORMATION:    /note= W = A or T (iv) SEQUENCE DESCRIPTION: SEQ ID NO: 5:

CCWWWWWWGG                                                                    10

(2) INFORMATION FOR SEQ ID NO: 6:

(i) SEQUENCE CHARACTERISTICS:
        (A) LENGTH:           1610 bases
        (B) TYPE:             nucleic acid
        (C) STRANDEDNESS:    single
        (D) TOPOLOGY:        linear (ii) MOLECULE TYPE:        cDNA (iv) SEQUENCE DESCRIPTION: SEQ ID NO: 6:

TCGAGGATCC GACCTTACCA CTTTCACAAT CTGCTAGCAA AGGTTATGCA GCGCGTGAAC    60

ATGATCATGG CAGAATCACC AGGCCTCATC ACCATCTGCC TTTTAGGATA TCTACTCAGT   120

```
GCTGAATGTA CAGTTTTTCT TGATCATGAA AACGCCAACA AAATTCTGAA TCGGCCAAAG      180

AGGTATAATT CAGGTAAATT GGAAGAGTTT GTTCAAGGGA ACCTTGAGAG AGAATGTATG      240

GAAGAAAAGT GTAGTTTTGA AGAAGCACGA GAAGTTTTTG AAAACACTGA AGAACAACT       300

GAATTTTGGA AGCAGTATGT TGATGGAGAT CAGTGTGAGT CCAATCCATG TTTAAATGGC      360

GGCAGTTGCA AGGATGACAT TAATTCCTAT GAATGTTGGT GTCCCTTTGG ATTTGAAGGA      420

AAGAACTGTG AATTAGATGT AACATGTAAC ATTAAGAATG CAGATGCGA GCAGTTTTGT       480

AAAAATAGTG CTGATAACAA GGTGGTTTGC TCCTGTACTG AGGGATATCG ACTTGCAGAA      540

AACCAGAAGT CCTGTGAACC AGCAGTGCCA TTTCCATGTG AAGAGTTTC TGTTTCACAA      600

ACTTCTAAGC TCACCCGTGC TGAGACTGTT TTTCCTGATG TGGACTATGT AAATTCTACT      660

GAAGCTGAAA CCATTTTGGA TAACATCACT CAAAGCACCC AATCATTTAA TGACTTCACT      720

CGGGTTGTTG GTGGAGAAGA TGCCAAACCA GGTCAATTCC CTTGGCAGGT TGTTTTGAAT      780

GGTAAAGTTG ATGCATTCTG TGGAGGCTCT ATCGTTAATG AAAAATGGAT TGTAACTGCT      840

GCCCACTGTG TTGAAACTGG TGTTAAAATT ACAGTTGTCG CAGGTGAACA TAATATTGAG      900

GAGACAGAAC ATACAGAGCA AAAGCGAAAT GTGATTCGAA TTATTCCTCA CCACAACTAC      960

AATGCAGCTA TTAATAAGTA CAACCATGAC ATTGCCCTTC TGGAACTGGA CGAACCCTTA     1020

GTGCTAAACA GCTACGTTAC ACCTATTTGC ATTGCTGACA AGGAATACAC GAACATCTTC     1080

CTCAAATTTG GATCTGGCTA TGTAAGTGGC TGGGGAAGAG TCTTCCACAA AGGGAGATCA     1140

GCTTTAGTTC TTCAGTACCT TAGAGTTCCA CTTGTTGACC GAGCCACATG TCTTCGATCT     1200

ACAAAGTTCA CCATCTATAA CAACATGTTC TGTGCTGGCT TCCATGAAGG AGGTAGAGAT     1260

TCATGTCAAG GAGATAGTGG GGGACCCCAT GTTACTGAAG TGGAAGGGAC CAGTTTCTTA     1320

ACTGGAATTA TTAGCTGGGG TGAAGAGTGT GCAATGAAAG GCAAATATGG AATATATACC     1380

AAGGTATCCC GGTATGTCAA CTGGATTAAG GAAAAAACAA AGCTCACTTA ATGAAAGATG     1440

GATTTCCAAG GTTAATTCAT TGGAATTGAA AATTAACAGG GCCTCTCACT AACTAATCAC     1500

TTTCCCATCT TTTGTTAGAT TTGAATATAT ACATTCTATG ATCATTGCTT TTTCTCTTTA     1560

CAGGGGAGAA TTTCATATTT TACCTGAGCT GAAGCTTGAT ATCGAATTCC                1610

(2) INFORMATION FOR SEQ ID NO: 7:

(i) SEQUENCE CHARACTERISTICS:
        (A) LENGTH:         6345 bases
        (B) TYPE:           nucleic acid
        (C) STRANDEDNESS:   double
        (D) TOPOLOGY:       linear (ii) MOLECULE TYPE:     cDNA (iv) SEQUENCE DESCRIPTION: SEQ ID NO: 7:

AGCTTATCGA TACCGTCGAC CTCGAGGGGG GGCCCGGTAC CCAGCTTTTG                  50

TCGAATAGCT ATGGCAGCTG AGCTCCCCC CCGGGCCATG GGTCGAAAAC

TTCCCTTTAG TGAGGGTTAA TTTCGAGCTT GGCGTAATCA TGGTCATAGC                 100

AAGGGAAATC ACTCCCAATT AAAGCTCGAA CCGCATTAGT ACCAGTATCG

TGTTTCCTGT GTGAAATTGT TATCCGCTCA CAATTCCACA ACATACGA                   150

ACAAAGGACA CACTTTAACA ATAGGCGAGT GTTAAGGTGT GTTGTATGCT

GCCGGAAGCA TAAAGTGTAA AGCCTGGGGT GCCTAATGAG TGAGCTAACT                 200

CGGCCTTCGT ATTTCACATT TCGGACCCCA CGGATTACTC ACTCGATTGA
```

```
CACATTAATT GCGTTGCGCT CACTGCCCGC TTTCCAGTCG GGAAACCTGT        250
GTGTAATTAA CGCAACGCGA GTGACGGGCG AAAGGTCAGC CCTTTGGACA
CGTGCCAGCT GCATTAATGA ATCGGCCAAC GCGCGGGGAG AGGCGGTTTG        300
GCACGGTCGA CGTAATTACT TAGCCGGTTG CGCGCCCCTC TCCGCCAAAC
CGTATTGGGC GCTCTTCCGC TTCCTCGCTC ACTGACTCGC TGCGCTCGGT        350
GCATAACCCG CGAGAAGGCG AAGGAGCGAG TGACTGAGCG ACGCGAGCCA
CGTTCGGCTG CGGCGAGCGG TATCAGCTCA CTCAAAGGCG GTAATACGGT        400
GCAAGCCGAC GCCGCTCGCC ATAGTCGAGT GAGTTTCCGC CATTATGCCA
TATCCACAGA ATCAGGGGAT AACGCAGGAA AGAACATGTG AGCAAAAGGC        450
ATAGGTGTCT TAGTCCCCTA TTGCGTCCTT TCTTGTACAC TCGTTTTCCG
CAGCAAAAGG CCAGGAACCG TAAAAAGGCC GCGTTGCTGG CGTTTTTCCA        500
GTCGTTTTCC GGTCCTTGGC ATTTTTCCGG CGCAACGACC GCAAAAAGGT
TAGGCTCCGC CCCCCTGACG AGCATCACAA AAATCGACGC TCAAGTCAGA        550
ATCCGAGGCG GGGGACTGC TCGTAGTGTT TTTAGCTGCG AGTTCAGTCT
GGTGGCGAAA CCCGACAGGA CTATAAAGAT ACCAGGCGTT TCCCCCTGGA        600
CCACCGCTTT GGGCTGTCCT GATATTTCTA TGGTCCGCAA AGGGGACCT
AGCTCCCTCG TGCGCTCTCC TGTTCCGACC CTGCCGCTTA CCGGATACCT        650
TCGAGGGAGC ACGCGAGAGG ACAAGGCTGG ACGGCGAAT GGCCTATGGA
GTCCGCCTTT CTCCCTTCGG GAAGCGTGGC GCTTTCTCAT AGCTCACGCT        700
CAGGCGGAAA GAGGGAAGCC CTTCGCACCG CGAAAGAGTA TCGAGTGCGA
GTAGGTATCT CAGTTCGGTG TAGGTCGTTC GCTCCAAGCT GGGCTGTGTG        750
CATCCATAGA GTCAAGCCAC ATCCAGCAAG CGAGGTTCGA CCCGACACAC
CACGAACCCC CCGTTCAGCC CGACCGCTGC GCCTTATCCG GTAACTATCG        800
GTGCTTGGGG GGCAAGTCGG GCTGGCGACG CGGAATAGGC CATTGATAGC
TCTTGAGTCC AACCCGGTAA GACACGACTT ATCGCCACTG GCAGCAGCCA        850
AGAACTCAGG TTGGGCCATT CTGTGCTGAA TAGCGGTGAC CGTCGTCGGT
CTGGTAACAG GATTAGCAGA GCGAGGTATG TAGGCGGTGC TACAGAGTTC        900
GACCATTGTC CTAATCGTCT CGCTCCATAC ATCCGCCACG ATGTCTCAAG
TTGAAGTGGT GGCCTAACTA CGGCTACACT AGAAGGACAG TATTTGGTAT        950
AACTTCACCA CCGGATTGAT GCCGATGTGA TCTTCCTGTC ATAAACCATA
CTGCGCTCTG CTGAAGCCAG TTACCTTCGG AAAAAGAGTT GGTAGCTCTT        1000
GACGCGAGAC GACTTCGGTC AATGGAAGCC TTTTTCTCAA CCATCGAGAA
GATCCGGCAA ACAAACCACC GCTGGTAGCG GTGGTTTTTT TGTTTGCAAG        1050
CTAGGCCGTT TGTTTGGTGG CGACCATCGC CACCAAAAAA ACAAACGTTC
CAGCAGATTA CGCGCAGAAA AAAAGGATCT CAAGAAGATC CTTTGATCTT        1100
GTCGTCTAAT GCGCGTCTTT TTTTCCTAGA GTTCTTCTAG GAAACTAGAA
TTCTACGGGG TCTGACGCTC AGTGGAACGA AAACTCACGT TAAGGGATTT        1150
AAGATGCCCC AGACTGCGAG TCACCTTGCT TTTGAGTGCA ATTCCCTAAA
TGGTCATGAG ATTATCAAAA AGGATCTTCA CCTAGATCCT TTTAAATTAA        1200
ACCAGTACTC TAATAGTTTT TCCTAGAAGT GGATCTAGGA AAATTTAATT
```

```
AAATGAAGTT TTAAATCAAT CTAAAGTATA TATGAGTAAA CTTGGTCTGA         1250

TTTACTTCAA AATTTAGTTA GATTTCATAT ATACTCATTT GAACCAGACT

CAGTTACCAA TGCTTAATCA GTGAGGCACC TATCTCAGCG ATCTGTCTAT         1300

GTCAATGGTT ACGAATTAGT CACTCCGTGG ATAGAGTCGC TAGACAGATA

TTCGTTCATC CATAGTTGCC TGACTCCCCG TCGTGTAGAT AACTACGATA         1350

AAGCAAGTAG GTATCAACGG ACTGAGGGGC AGCACATCTA TTGATGCTAT

CGGGAGGGCT TACCATCTGG CCCCAGTGCT GCAATGATAC CGCGAGACCC         1400

GCCCTCCCGA ATGGTAGACC GGGGTCACGA CGTTACTATG GCGCTCTGGG

ACGCTCACCG GCTCCAGATT TATCAGCAAT AAACCAGCCA GCCGGAAGGG         1450

TGCGAGTGGC CGAGGTCTAA ATAGTCGTTA TTTGGTCGGT CGGCCTTCCC

CCGAGCGCAG AAGTGGTCCT GCAACTTTAT CCGCCTCCAT CCAGTCTATT         1500

GGCTCGCGTC TTCACCAGGA CGTTGAAATA GGCGGAGGTA GGTCAGATAA

AATTGTTGCC GGGAAGCTAG AGTAAGTAGT TCGCCAGTTA ATAGTTTGCG         1550

TTAACAACGG CCCTTCGATC TCATTCATCA AGCGGTCAAT TATCAAACGC

CAACGTTGTT GCCATTGCTA CAGGCATCGT GGTGTCACGC TCGTCGTTTG         1600

GTTGCAACAA CGGTAACGAT GTCCGTAGCA CCACAGTGCG AGCAGCAAAC

GTATGGCTTC ATTCAGCTCC GGTTCCCAAC GATCAAGGCG AGTTACATGA         1650

CATACCGAAG TAAGTCGAGG CCAAGGGTTG CTAGTTCCGC TCAATGTACT

TCCCCCATGT TGTGCAAAAA AGCGGTTAGC TCCTTCGGTC CTCCGATCGT         1700

AGGGGGTACA ACACGTTTTT TCGCCAATCG AGGAAGCCAG GAGGCTAGCA

TGTCAGAAGT AAGTTGGCCG CAGTGTTATC ACTCATGGTT ATGGCAGCAC         1750

ACAGTCTTCA TTCAACCGGC GTCACAATAG TGAGTACCAA TACCGTCGTG

TGCATAATTC TCTTACTGTC ATGCCATCCG TAAGATGCTT TTCTGTGACT         1800

ACGTATTAAG AGAATGACAG TACGGTAGGC ATTCTACGAA AAGACACTGA

GGTGAGTACT CAACCAAGTC ATTCTGAGAA TAGTGTATGC GGCGACCGAG         1850

CCACTCATGA GTTGGTTCAG TAAGACTCTT ATCACATACG CCGCTGGCTC

TTGCTCTTGC CCGGCGTCAA TACGGGATAA TACCGCGCCA CATAGCAGAA         1900

AACGAGAACG GGCCGCAGTT ATGCCCTATT ATGGCGCGGT GTATCGTCTT

CTTTAAAAGT GCTCATCATT GGAAAACGTT CTTCGGGGCG AAAACTCTCA         1950

GAAATTTTCA CGAGTAGTAA CCTTTTGCAA GAAGCCCCGC TTTTGAGAGT

AGGATCTTAC CGCTGTTGAG ATCCAGTTCG ATGTAACCCA CTCGTGCACC         2000

TCCTAGAATG GCGACAACTC TAGGTCAAGC TACATTGGGT GAGCACGTGG

CAACTGATCT TCAGCATCTT TTACTTTCAC CAGCGTTTCT GGGTGAGCAA         2050

GTTGACTAGA AGTCGTAGAA AATGAAAGTG GTCGCAAAGA CCCACTCGTT

AAACAGGAAG GCAAAATGCC GCAAAAAAGG GAATAAGGGC GACACGGAAA         2100

TTTGTCCTTC CGTTTTACGG CGTTTTTTCC CTTATTCCCG CTGTGCCTTT

TGTTGAATAC TCATACTCTT CCTTTTTCAA TATTATTGAA GCATTTATCA         2150

ACAACTTATG AGTATGAGAA GGAAAAAGTT ATAATAACTT CGTAAATAGT

GGGTTATTGT CTCATGAGCG GATACATATT TGAATGTATT TAGAAAAATA         2200

CCCAATAACA GAGTACTCGC CTATGTATAA ACTTACATAA ATCTTTTTAT
```

```
AACAAATAGG GGTTCCGCGC ACATTTCCCC GAAAAGTGCC ACCTAAATTG         2250

TTGTTTATCC CCAAGGCGCG TGTAAAGGGG CTTTTCACGG TGGATTTAAC

TAAGCGTTAA TATTTGTTA AAATTCGCGT TAAATTTTG TTAAATCAGC           2300

ATTCGCAATT ATAAAACAAT TTTAAGCGCA ATTTAAAAAC AATTTAGTCG

TCATTTTTTA ACCAATAGGC CGAAATCGGC AAAATCCCTT ATAAATCAAA         2350

AGTAAAAAAT TGGTTATCCG GCTTTAGCCG TTTTAGGGAA TATTTAGTTT

AGAATAGACC GAGATAGGGT TGAGTGTTGT TCCAGTTTGG AACAAGAGTC         2400

TCTTATCTGG CTCTATCCCA ACTCACAACA AGGTCAAACC TTGTTCTCAG

CACTATTAAA GAACGTGGAC TCCAACGTCA AAGGGCGAAA AACCGTCTAT         2450

GTGATAATTT CTTGCACCTG AGGTTGCAGT TTCCCGCTTT TTGGCAGATA

CAGGGCGATG GCCCACTACG TGAACCATCA CCCTAATCAA GTTTTTTGGG         2500

GTCCCGCTAC CGGGTGATGC ACTTGGTAGT GGGATTAGTT CAAAAAACCC

GTCGAGGTGC CGTAAAGCAC TAAATCGGAA CCCTAAAGGG AGCCCCCGAT         2550

CAGCTCCACG GCATTTCGTG ATTTAGCCTT GGGATTTCCC TCGGGGCTA

TTAGAGCTTG ACGGGAAAG CCGGCGAACG TGGCGAGAAA GGAAGGGAAG         2600

AATCTCGAAC TGCCCCTTTC GGCCGCTTGC ACCGCTCTTT CCTTCCCTTC

AAAGCGAAAG GAGCGGGCGC TAGGGCGCTG GCAAGTGTAG CGGTCACGCT         2650

TTTCGCTTTC CTCGCCCGCG ATCCCGCGAC CGTTCACATC GCCAGTGCGA

GCGCGTAACC ACCACACCCG CCGCGCTTAA TGCGCCGCTA CAGGGCGCGT         2700

CGCGCATTGG TGGTGTGGGC GGCGCGAATT ACGCGGCGAT GTCCCGCGCA

CCCATTCGCC ATTCAGGCTG CGCAACTGTT GGGAAGGGCG ATCGGTGCGG         2750

GGGTAAGCGG TAAGTCCGAC GCGTTGACAA CCCTTCCCGC TAGCCACGCC

GCCTCTTCGC TATTACGCCA GCTGGCGAAA GGGGGATGTG CTGCAAGGCG         2800

CGGAGAAGCG ATAATGCGGT CGACCGCTTT CCCCCTACAC GACGTTCCGC

ATTAAGTTGG GTAACGCCAG GGTTTTCCCA GTCACGACGT TGTAAAACGA         2850

TAATTCAACC CATTGCGGTC CCAAAAGGGT CAGTGCTGCA ACATTTTGCT

CGGCCAGTGA ATTGTAATAC GACTCACTAT AGGGCGAATT GGAGCTCCAC         2900

GCCGGTCACT TAACATTATG CTGAGTGATA TCCCGCTTAA CCTCGAGGTG

CGCGGTGGCG GCCGCTCTAG AACTAGTGGA TCCTCTAGAG TCTGCCTGCC         2950

GCGCCACCGC CGGCGAGATC TTGATCACCT AGGAGATCTC AGACGGACGG

CCCTGCCTGG CACAGCCCGT ACCTGGCCGC ACGCTCCCTC ACAGGTGAAG         3000

GGGACGGACC GTGTCGGGCA TGGACCGGCG TGCGAGGGAG TGTCCACTTC

CTCGAAAACT CCGTCCCCGT AAGGAGCCCC GCTGCCCCCC GAGGCCTCCT         3050

GAGCTTTTGA GGCAGGGGCA TTCCTCGGGG CGACGGGGGG CTCCGGAGGA

CCCTCACGCC TCGCTGCGCT CCCGGCTCCC GCACGGCCCT GGGAGAGGCC         3100

GGGAGTGCGG AGCGACGCGA GGGCCGAGGG CGTGCCGGGA CCCTCTCCGG

CCCACCGCTT CGTCCTTAAC GGGCCCGGCG GTGCCGGGGG ATTATTTCGG         3150

GGGTGGCGAA GCAGGAATTG CCCGGGCCGC CACGGCCCCC TAATAAAGCC

CCCCGGCCCC GGGGGGGCCC GGCAGACGCT CCTTATACGG CCCGGCCTCG         3200

GGGGCCGGGG CCCCCCCGGG CCGTCTGCGA GGAATATGCC GGGCCGGAGC
```

```
CTCACCTGGG CCGCGGCCAG GAGCGCCTTC TTTGGGCAGC GCCGGGCCGG        3250
GAGTGGACCC GGCGCCGGTC CTCGCGGAAG AAACCCGTCG CGGCCCGGCC
GGCCGCGCCG GGCCCGACAC CCAAATATGG CGACGGCCGG GGCCGCATTC        3300
CCGGCGCGGC CCGGGCTGTG GGTTTATACC GCTGCCGGCC CCGGCGTAAG
CTGGGGGCCG GGCGGTGCTC CCGCCCGCCT CGATAAAAGG CTCCGGGGCC        3350
GACCCCCGGC CCGCCACGAG GGCGGGCGGA GCTATTTTCC GAGGCCCCGG
GGCGGCGGCC CACGAGCTAC CCGGAGGAGC GGGAGGCGTC TCTGCCAGCG        3400
CCGCCGCCGG GTGCTCGATG GGCCTCCTCG CCCTCCGCAG AGACGGTCGC
GCCCGACGCG CAGTCAGCAC AGGTAGGTGG GCACCGCGCC GTGCCGTGCC        3450
CGGGCTGCGC GTCAGTCGTG TCCATCCACC CGTGGCGCGG CACGGCACGG
GTGCCGTGCC GCCCGGCGCC CCTTCGCGGG GCCGTCGTGT GGGCCCTCCG        3500
CACGGCACGG CGGGCCGCGG GGAAGCGCCC CGGCAGCACA CCCGGGAGGC
TGGGCCCCGC CGTCACCCTG AGCCTCACGG CCCCGTGCCC CGCAGACAGC        3550
ACCCGGGGCG GCAGTGGGAC TCGGAGTGCC GGGGCACGGG GCGTCTGTCG
CAGCACCATG GGAAAAATCA GCAGTCTTCC AACCCAATTA TTTAAGTGCT        3600
GTCGTGGTAC CCTTTTTAGT CGTCAGAAGG TTGGGTTAAT AAATTCACGA
GCTTTTGTGA TTTCTTGAAG GTGAAGATGC ACACCATGTC CTCCTCGCAT        3650
CGAAAACACT AAAGAACTTC CACTTCTACG TGTGGTACAG GAGGAGCGTA
CTCTTCTACC TGGCGCTGTG CCTGCTCACC TTCACCAGCT CTGCCACGGC        3700
GAGAAGATGG ACCGCGACAC GGACGAGTGG AAGTGGTCGA CGGTGCCG
TGGACCGGAG ACGCTCTGCG GGGCTGAGCT GGTGGATGCT CTTCAGTTCG        3750
ACCTGGCCTC TGCGAGACGC CCCGACTCGA CCACCTACGA GAAGTCAAGC
TGTGTGGAGA CAGGGGCTTT TATTTCAACA AGCCCACAGG GTATGGCTCC        3800
ACACACCTCT GTCCCCGAAA ATAAAGTTGT TCGGGTGTCC CATACCGAGG
AGCAGTCGGA GGGCGCCTCA GACAGGCATC GTGGATGAGT GCTGCTTCCG        3850
TCGTCAGCCT CCCGCGGAGT CTGTCCGTAG CACCTACTCA CGACGAAGGC
GAGCTGTGAT CTAAGGAGGC TGGAGATGTA TTGCGCACCC CTCAAGCCTG        3900
CTCGACACTA GATTCCTCCG ACCTCTACAT AACGCGTGGG GAGTTCGGAC
CCAAGTCAGC TCGCTCTGTC CGTGCCCAGC GCCACACCGA CATGCCCAAG        3950
GGTTCAGTCG AGCGAGACAG GCACGGGTCG CGGTGTGGCT GTACGGGTTC
ACCCAGAAGG AAGTACATTT GAAGAACGCA AGTAGAGGGA GTGCAGGAAA        4000
TGGGTCTTCC TTCATGTAAA CTTCTTGCGT TCATCTCCCT CACGTCCTTT
CAAGAACTAC AGGATGTAGG AAGACCCTCC TGAGGAGTGA AGAGTGACAT        4050
GTTCTTGATG TCCTACATCC TTCTGGGAGG ACTCCTCACT TCTCACTGTA
GCCACCGCAG GATCCCCCGG GCTGCAGGAA TTCGATGGCC CATCCATTGT        4100
CGGTGGCGTC CTAGGGGGCC CGACGTCCTT AAGCTACCGG GTAGGTAACA
CCACCGTAAA TGCTTCTAAA CATGTTTACA TGATCACTTT GCCAACCACA        4150
GGTGGCATTT ACGAAGATTT GTACAAATGT ACTAGTGAAA CGGTTGGTGT
CTCAGGATGA CAATCTTGTA GGTTCCAGGC TGCTGAGGAC CTGCACCAGC        4200
GAGTCCTACT GTTAGAACAT CCAAGGTCCG ACGACTCCTG GACGTGGTCG
```

```
CATGCAACTT TCTATTTTGT AACAATTTCT GGTTACTGTT GCTGCAAAGC        4250
GTACGTTGAA AGATAAAACA TTGTTAAAGA CCAATGACAA CGACGTTTCG
TCCATGTGAC ACAGTGTATG TAAAGTGTAC ATAAATTAAT TTATTTTACC        4300
AGGTACACTG TGTCACATAC ATTTCACATG TATTTAATTA AATAAAATGG
TCGTTTTGTT TGTTTTTAAA ACCAATGCCC TGTGGAAGGA AACATAAAAC        4350
AGCAAAACAA ACAAAAATTT TGGTTACGGG ACACCTTCCT TTGTATTTTG
TTCAAGAAGC ATTAAATCAT CAGTCATTCT GTCACACCCC TAATGCAGTT        4400
AAGTTCTTCG TAATTTAGTA GTCAGTAAGA CAGTGTGGGG ATTACGTCAA
GTTTCTGTCA TCATTTCCCT GGGCTCTTCC ATCTCTCGCT GACCTGGGAC        4450
CAAAGACAGT AGTAAAGGGA CCCGAGAAGG TAGAGAGCGA CTGGACCCTG
TGGGTGCTGG GGCTGGGAGC AGGGGTTGGG GCTCTCCAGG GAGAGATGGC        4500
ACCCACGACC CCGACCCTCG TCCCCAACCC CGAGAGGTCC CTCTCTACCG
ATGGGGAGAG TGATGGGATA CTGCTGGGGG GGGGGACTC ACCCTGCTGT         4550
TACCCCTCTC ACTACCCTAT GACGACCCCC CCCCCCTGAG TGGGACGACA
GGGCTGCAGG AAGCCCATTG GTGCAGAGAG CAGCCTGGGA TGCCCATGAC        4600
CCCGACGTCC TTCGGGTAAC CACGTCTCTC GTCGGACCCT ACGGGTACTG
ACGGGCACCC ACTGCACCGT GTTTCTCCCA TGCCCAGTAG GGAAAGGGTT        4650
TGCCCGTGGG TGACGTGGCA CAAAGAGGGT ACGGGTCATC CCTTTCCCAA
ACGAGCGCCG TTCATTCTCA GCTTGTGAAG GATTTTGTTG GGCTCAGCCT        4700
TGCTCGCGGC AAGTAAGAGT CGAACACTTC CTAAAACAAC CCGAGTCGGA
GCCAGAGCAG TAGCCAGGCA TGCCTGTGCA GCTCCGAGCT GTGATGGACA        4750
CGGTCTCGTC ATCGGTCCGT ACGGACACGT CGAGGCTCGA CACTACCTGT
GAGGCAAGGC TGCAGCTGAG GCCAGGTGGT GGGCACAGGT TAAATTAAGA        4800
CTCCGTTCCG ACGTCGACTC CGGTCCACCA CCCGTGTCCA ATTTAATTCT
GCTTTCCACT CCACTTATGG AAAGCCCTCC TGCACTCACC CTGTCCCTGG        4850
CGAAAGGTGA GGTGAATACC TTTCGGGAGG ACGTGAGTGG GACAGGGACC
GGCTGGGGGC AGCCAGGGCC ACTTCCTCAC CCCACCTGAC ACACAAGGCT        4900
CCGACCCCCG TCGGTCCCGG TGAAGGAGTG GGGTGGACTG TGTGTTCCGA
TTGCCTGCAC AGCCAGGACC TCCTGTGGCC ACAGACTCTT ATAGATTCGC        4950
AACGGACGTG TCGGTCCTGG AGGACACCGG TGTCTGAGAA TATCTAAGCG
TGTGCCCTAG GAGACCAGGG GGCTTTCCCT GCCTGGCCTT CTGGCCCCGG        5000
ACACGGGATC CTCTGGTCCC CCGAAAGGGA CGGACCGGAA GACCGGGGCC
CGACACTGCA GGAGCTGCCC TATCTGCCTC CTCTTAGATG GTCCTGGCAG        5050
GCTGTGACGT CCTCGACGGG ATAGACGGAG GAGAATCTAC CAGGACCGTC
GAAGGCTGCA CTTGGCTTGG GGCTGATCCA TATTACCACT GCAGTAGGGA        5100
CTTCCGACGT GAACCGAACC CCGACTAGGT ATAATGGTGA CGTCATCCCT
CAGCACTGCT GGAAGAAAAG ATGATTTTCA ACTGAACTTA CTATCCAGGC        5150
GTCGTGACGA CCTTCTTTTC TACTAAAAGT TGACTTGAAT GATAGGTCCG
AGGTTATTGC TTTATTGTGA TGGTGCTAAG AGTGCGTTCT TTCTCACTGT        5200
TCCAATAACG AAATAACACT ACCACGATTC TCACGCAAGA AAGAGTGACA
```

```
AATGATTTTG CCCTCATGTG TGAATACACT TTCCAATAAC AGCACAGCCT    5250
TTACTAAAAC GGGAGTACAC ACTTATGTGA AAGGTTATTG TCGTGTCGGA
CCAAAGGGAA TTTCTGCAGG AAGAGACAGT ACCTGGTGTG GGAAGTCCCT    5300
GGTTTCCCTT AAAGACGTCC TTCTCTGTCA TGGACCACAC CCTTCAGGGA
GTGCAGCCCT ATGTGCTTCA AGCTGAATGG CTGGGACTGG CTGGGAGAGC    5350
CACGTCGGGA TACACGAAGT TCGACTTACC GACCCTGACC GACCCTCTCG
AGGATCACAT CCTTTCTTAA AAAGACAAAC AGAAGGTAGT GTGTGACCTT    5400
TCCTAGTGTA GGAAAGAATT TTTCTGTTTG TCTTCCATCA CACACTGGAA
GCTGTATTTA CTATTTACGC GTTGTTGTTC AGTGGCACAT ACCTCAACGG    5450
CGACATAAAT GATAAATGCG CAACAACAAG TCACCGTGTA TGGAGTTGCC
GGATATGGAG AGCTATTTCC CCAACCCTCG CTGCTGGACC CTGATCTGGG    5500
CCTATACCTC TCGATAAAGG GGTTGGGAGC GACGACCTGG GACTAGACCC
GTTTTCCTGT AGCTTAAGCG GTGCCAACTG CTTAAGTGAT TGTAGAATCA    5550
CAAAAGGACA TCGAATTCGC CACGGTTGAC GAATTCACTA ACATCTTAGT
GTAAGGCTGG AAAAGACCAC AGATCATTAA GTCCAACTGT CAGCCCCATC    5600
CATTCCGACC TTTTCTGGTG TCTAGTAATT CAGGTTGACA GTCGGGGTAG
CCCACCGCGC CCACTGTCAC TCAGTGCCAC ATCCACGCAT TTCTTGAACA    5650
GGGTGGCGCG GGTGACAGTG AGTCACGGTG TAGGTGCGTA AAGAACTTGT
TCTCCAGGGA CAGTGACTCC ACCCGTCACC AGCTGTGCTT CAGAGCAGGC    5700
AGAGGTCCCT GTCACTGAGG TGGGCAGTGG TCGACACGAA GTCTCGTCCG
AGGGTGACAG TCTCAGTGCC AGTTGCATCC TGCTGAAGAG CTTAACAGTG    5750
TCCCACTGTC AGAGTCACGG TCAACGTAGG ACGACTTCTC GAATTGTCAC
CAGTTTAACA ACGGACTGAT TGTTGATGT GGTTGCTGAA TCAGTACGTT    5800
GTCAAATTGT TGCCTGACTA AACAACTACA CCAACGACTT AGTCATGCAA
GAGATGTCAC TAAACTTTTT GGAGATTAAT TTCAGGATGG AACACATTCT    5850
CTCTACAGTG ATTTGAAAAA CCTCTAATTA AAGTCCTACC TTGTGTAAGA
TAACCCTGAA ACCAGCCTTT GATTTGGGCT TGGCATTTGC AGAATTTGCA    5900
ATTGGGACTT TGGTCGGAAA CTAAACCCGA ACCGTAAACG TCTTAAACGT
GGAAAAGATT GTTTGGGAAC AGATGAATGG AATTTCCACC AAACAGAAAA    5950
CCTTTTCTAA CAAACCCTTG TCTACTTACC TTAAAGGTGG TTTGTCTTTT
TTAACACTTA CACCAGTTTG AGTCTGGTCT TCGTTGGATA TTTCTTAAGA    6000
AATTGTGAAT GTGGTCAAAC TCAGACCAGA AGCAACCTAT AAAGAATTCT
ATCTCATCAT CCTCCCTGCT CTTGGACCAG TGCTGCTGAC AGGAGGTGGA    6050
TAGAGTAGTA GGAGGGACGA GAACCTGGTC ACGACGACTG TCCTCCACCT
GGATCATCAG GGTCAGCATC CTCAGCATCT AGGGATGTGC ACTATGTGTG    6100
CCTAGTAGTC CCAGTCGTAG GAGTCGTAGA TCCCTACACG TGATACACAC
ATGGTGACAC TTTAGAGAAC TGCTTTGATT CCCCAGGGCT TTCCCTCTCT    6150
TACCACTGTG AAATCTCTTG ACGAAACTAA GGGGTCCCGA AAGGGAGAGA
TCCATGCAGG GCTCACTATC AGCCCTGAAA GTCCAACTTT CTGAACTTCC    6200
AGGTACGTCC CGAGTGATAG TCGGGACTTT CAGGTTGAAA GACTTGAAGG
```

```
AGCACCGTCT GCTCCTGGTA GGCTGTTCCA TAGAGGCCAC AGGGACTGTA        6250

TCGTGGCAGA CGAGGACCAT CCGACAAGGT ATCTCCGGTG TCCCTGACAT

GCCAGGCATG ACCTTTTCCC AGCCGTGCTC TGAATCCAGC ACTGGTGGCT        6300

CGGTCCGTAC TGGAAAAGGG TCGGCACGAG ACTTAGGTCG TGACCACCGA

GGGAGGCAGC TCTGGTCCTG GGGTGCTGCA GTGAGCCAGG GAACA            6345

CCCTCCGTCG AGACCAGGAC CCCACGACGT CACTCGGTCC CTTGT (2) INFORMATION FOR SEQ ID NO: 8:

(i) SEQUENCE CHARACTERISTICS:
           (A) LENGTH:            5707 bases
           (B) TYPE:              nucleic acid
           (C) STRANDEDNESS:      double
           (D) TOPOLOGY:          linear (ii) MOLECULE TYPE:         cDNA (iv) SEQUENCE DESCRIPTION: SEQ ID NO: 8:

GGCCGCTCTA GAACTAGTGG ATCCTCTAGA GTCTGCCTGC CCCCTGCCTG          50

CCGGCGAGAT CTTGATCACC TAGGAGATCT CAGACGGACG GGGGACGGAC

GCACAGCCCG TACCTGGCCG CACGCTCCCT CACAGGTGAA GCTCGAAAAC         100

CGTGTCGGGC ATGGACCGGC GTGCGAGGGA GTGTCCACTT CGAGCTTTTG

TCCGTCCCCG TAAGGAGCCC CGCTGCCCCC CGAGGCCTCC TCCCTCACGC         150

AGGCAGGGGC ATTCCTCGGG GCGACGGGGG GCTCCGGAGG AGGGAGTGCG

CTCGCTGCGC TCCCGGCTCC CGCACGGCCC TGGGAGAGGC CCCCACCGCT         200

GAGCGACGCG AGGGCCGAGG GCGTGCCGGG ACCCTCTCCG GGGGTGGCGA

TCGTCCTTAA CGGGCCCGGC GGTGCCGGGG GATTATTTCG GCCCCGGCCC         250

AGCAGGAATT GCCCGGGCCG CCACGGCCCC CTAATAAAGC CGGGGCCGGG

CGGGGGGGCC CGGCAGACGC TCCTTATACG GCCCGGCCTC GCTCACCTGG         300

GCCCCCCCGG GCCGTCTGCG AGGAATATGC CGGGCCGGAG CGAGTGGACC

GCCGCGGCCA GGAGCGCCTT CTTTGGGCAG CGCCGGGCCG GGGCCGCGCC         350

CGGCGCCGGT CCTCGCGGAA GAAACCCGTC GCGGCCCGGC CCCGGCGCGG

GGGCCCGACA CCCAAATATG CGACGGCCG GGGCCGCATT CCTGGGGGCC         400

CCCGGGCTGT GGGTTTATAC GCTGCCGGC CCCGGCGTAA GGACCCCCGG

GGGCGGTGCT CCCGCCCGCC TCGATAAAAG GCTCCGGGGC CGGCGGCGGC         450

CCCGCCACGA GGGCGGGCGG AGCTATTTTC CGAGGCCCCG GCCGCCGCCG

CCACGAGCTA CCCGGAGGAG CGGGAGGCGT CTCTGCCAGC GGCCCGACGC         500

GGTGCTCGAT GGGCCTCCTC GCCCTCCGCA GAGACGGTCG CCGGGCTGCG

GCAGTCAGCA CAGGTAGGTG GGCACCGCGC CGTGCCGTGC CGTGCCGTGC         550

CGTCAGTCGT GTCCATCCAC CCGTGGCGCG GCACGGCACG GCACGGCACG

CGCCCGGCGC CCCTTCGCGG GGCCGTCGTG TGGGCCCTCC GTGGGCCCCG         600

GCGGGCCGCG GGGAAGCGCC CCGGCAGCAC ACCCGGGAGG CACCCGGGGC

CCGTCACCCT GAGCCTCACG GCCCCGTGCC CCGCAGACAG CCAGCACCAT         650

GGCAGTGGGA CTCGGAGTGC CGGGGCACGG GGCGTCTGTC GGTCGTGGTA

GGGAAAAATC AGCAGTCTTC CAACCCAATT ATTTAAGTGC TGCTTTTGTG         700

CCCTTTTTAG TCGTCAGAAG GTTGGGTTAA TAAATTCACG ACGAAAACAC
```

| | |
|---|---|
| ATTTCTTGAA GGTGAAGATG CACACCATGT CCTCCTCGCA TCTCTTCTAC | 750 |
| TAAAGAACTT CCACTTCTAC GTGTGGTACA GGAGGAGCGT AGAGAAGATG | |
| CTGGCGCTGT GCCTGCTCAC CTTCACCAGC TCTGCCACGG CTGGACCGGA | 800 |
| GACCGCGACA CGGACGAGTG GAAGTGGTCG AGACGGTGCC GACCTGGCCT | |
| GACGCTCTGC GGGGCTGAGC TGGTGGATGC TCTTCAGTTC GTGTGTGGAG | 850 |
| CTGCGAGACG CCCCGACTCG ACCACCTACG AGAAGTCAAG CACACACCTC | |
| ACAGGGCTT TTATTTCAAC AAGCCCACAG GGTATGGCTC CAGCAGTCGG | 900 |
| TGTCCCCGAA AATAAAGTTG TTCGGGTGTC CCATACCGAG GTCGTCAGCC | |
| AGGGCGCCTC AGACAGGCAT CGTGGATGAG TGCTGCTTCC GGAGCTGTGA | 950 |
| TCCCGCGGAG TCTGTCCGTA GCACCTACTC ACGACGAAGG CCTCGACACT | |
| TCTAAGGAGG CTGGAGATGT ATTGCGCACC CCTCAAGCCT GCCAAGTCAG | 1000 |
| AGATTCCTCC GACCTCTACA TAACGCGTGG GGAGTTCGGA CGGTTCAGTC | |
| CTCGCTCTGT CCGTGCCCAG CGCCACACCG ACATGCCCAA GACCCAGAAG | 1050 |
| GAGCGAGACA GGCACGGGTC GCGGTGTGGC TGTACGGGTT CTGGGTCTTC | |
| GAAGTACATT TGAAGAACGC AAGTAGAGGG AGTGCAGGAA ACAAGAACTA | 1100 |
| CTTCATGTAA ACTTCTTGCG TTCATCTCCC TCACGTCCTT TGTTCTTGAT | |
| CAGGATGTAG GAAGACCCTC CTGAGGAGTG AAGAGTGACA TGCCACCGCA | 1150 |
| GTCCTACATC CTTCTGGGAG GACTCCTCAC TTCTCACTGT ACGGTGGCGT | |
| GGATCCCCCG GGCTGCAGGA ATTCGATGGC CCATCCATTG TCCACCGTAA | 1200 |
| CCTAGGGGGC CCGACGTCCT TAAGCTACCG GGTAGGTAAC AGGTGGCATT | |
| ATGCTTCTAA ACATGTTTAC ATGATCACTT TGCCAACCAC ACTCAGGATG | 1250 |
| TACGAAGATT TGTACAAATG TACTAGTGAA ACGGTTGGTG TGAGTCCTAC | |
| ACAATCTTGT AGGTTCCAGG CTGCTGAGGA CCTGCACCAG CCATGCAACT | 1300 |
| TGTTAGAACA TCCAAGGTCC GACGACTCCT GGACGTGGTC GGTACGTTGA | |
| TTCTATTTTG TAACAATTTC TGGTTACTGT TGCTGCAAAG CTCCATGTGA | 1350 |
| AAGATAAAAC ATTGTTAAAG ACCAATGACA ACGACGTTTC GAGGTACACT | |
| CACAGTGTAT GTAAAGTGTA CATAAATTAA TTTATTTTAC CTCGTTTTGT | 1400 |
| GTGTCACATA CATTTCACAT GTATTTAATT AAATAAAATG GAGCAAAACA | |
| TTGTTTTTAA AACCAATGCC CTGTGGAAGG AAACATAAAA CTTCAAGAAG | 1450 |
| AACAAAAATT TTGGTTACGG GACACCTTCC TTTGTATTTT GAAGTTCTTC | |
| CATTAAATCA TCAGTCATTC TGTCACACCC CTAATGCAGT TGTTTCTGTC | 1500 |
| GTAATTTAGT AGTCAGTAAG ACAGTGTGGG GATTACGTCA ACAAAGACAG | |
| ATCATTTCCC TGGGCTCTTC CATCTCTCGC TGACCTGGGA CTGGGTGCTG | 1550 |
| TAGTAAAGGG ACCCGAGAAG GTAGAGAGCG ACTGGACCCT GACCCACGAC | |
| GGGCTGGGAG CAGGGGTTGG GGCTCTCCAG GGAGAGATGG CATGGGAGA | 1600 |
| CCCGACCCTC GTCCCCAACC CCGAGAGGTC CCTCTCTACC GTACCCCTCT | |
| GTGATGGGAT ACTGCTGGGG GGGGGGACT CACCCTGCTG TGGGCTGCAG | 1650 |
| CACTACCCTA TGACGACCCC CCCCCCTGA GTGGGACGAC ACCCGACGTC | |
| GAAGCCCATT GGTGCAGAGA GCAGCCTGGG ATGCCCATGA CACGGGCACC | 1700 |
| CTTCGGGTAA CCACGTCTCT CGTCGGACCC TACGGGTACT GTGCCCGTGG | |

```
CACTGCACCG TGTTTCTCCC ATGCCCAGTA GGGAAAGGGT TACGAGCGCC      1750
GTGACGTGGC ACAAAGAGGG TACGGGTCAT CCCTTTCCCA ATGCTCGCGG
GTTCATTCTC AGCTTGTGAA GGATTTTGTT GGGCTCAGCC TGCCAGAGCA      1800
CAAGTAAGAG TCGAACACTT CCTAAAACAA CCCGAGTCGG ACGGTCTCGT
GTAGCCAGGC ATGCCTGTGC AGCTCCGAGC TGTGATGGAC AGAGGCAAGG      1850
CATCGGTCCG TACGGACACG TCGAGGCTCG ACACTACCTG TCTCCGTTCC
CTGCAGCTGA GGCCAGGTGG TGGGCACAGG TTAAATTAAG AGCTTTCCAC      1900
GACGTCGACT CCGGTCCACC ACCCGTGTCC AATTTAATTC TCGAAAGGTG
TCCACTTATG GAAAGCCCTC CTGCACTCAC CCTGTCCCTG GGGCTGGGGG      1950
AGGTGAATAC CTTTCGGGAG GACGTGAGTG GGACAGGGAC CCCGACCCCC
CAGCCAGGGC CACTTCCTCA CCCCACCTGA CACACAAGGC TTTGCCTGCA      2000
GTCGGTCCCG GTGAAGGAGT GGGGTGGACT GTGTGTTCCG AAACGGACGT
CAGCCAGGAC CTCCTGTGGC CACAGACTCT TATAGATTCG CTGTGCCCTA      2050
GTCGGTCCTG GAGGACACCG GTGTCTGAGA ATATCTAAGC GACACGGGAT
GGAGACCAGG GGGCTTTCCC TGCCTGGCCT TCTGGCCCCG GCGACACTGC      2100
CCTCTGGTCC CCCGAAAGGG ACGGACCGGA AGACCGGGGC CGCTGTGACG
AGGAGCTGCC CTATCTGCCT CCTCTTAGAT GGTCCTGGCA GGAAGGCTGC      2150
TCCTCGACGG GATAGACGGA GGAGAATCTA CCAGGACCGT CCTTCCGACG
ACTTGGCTTG GGGCTGATCC ATATTACCAC TGCAGTAGGG ACAGCACTGC      2200
TGAACCGAAC CCCGACTAGG TATAATGGTG ACGTCATCCC TGTCGTGACG
TGGAAGAAAA GATGATTTTC AACTGAACTT ACTATCCAGG CAGGTTATTG      2250
ACCTTCTTTT CTACTAAAAG TTGACTTGAA TGATAGGTCC GTCCAATAAC
CTTTATTGTG ATGGTGCTAA GAGTGCGTTC TTTCTCACTG TAATGATTTT      2300
GAAATAACAC TACCACGATT CTCACGCAAG AAAGAGTGAC ATTACTAAAA
GCCCTCATGT GTGAATACAC TTTCCAATAA CAGCACAGCC TCCAAAGGGA      2350
CGGGAGTACA CACTTATGTG AAAGGTTATT GTCGTGTCGG AGGTTTCCCT
ATTTCTGCAG GAAGAGACAG TACCTGGTGT GGGAAGTCCC TGTGCAGCCC      2400
TAAAGACGTC CTTCTCTGTC ATGGACCACA CCCTTCAGGG ACACGTCGGG
TATGTGCTTC AAGCTGAATG GCTGGGACTG GCTGGGAGAG CAGGATCACA      2450
ATACACGAAG TTCGACTTAC CGACCCTGAC CGACCCTCTC GTCCTAGTGT
TCCTTTCTTA AAAAGACAAA CAGAAGGTAG TGTGTGACCT TGCTGTATTT      2500
AGGAAAGAAT TTTTCTGTTT GTCTTCCATC ACACACTGGA ACGACATAAA
ACTATTTACG CGTTGTTGTT CAGTGGCACA TACCTCAACG GGGATATGGA      2550
TGATAAATGC GCAACAACAA GTCACCGTGT ATGGAGTTGC CCCTATACCT
GAGCTATTTC CCCAACCCTC GCTGCTGGAC CCTGATCTGG GGTTTTCCTG      2600
CTCGATAAAG GGGTTGGGAG CGACGACCTG GGACTAGACC CCAAAAGGAC
TAGCTTAAGC GGTGCCAACT GCTTAAGTGA TTGTAGAATC AGTAAGGCTG      2650
ATCGAATTCG CCACGGTTGA CGAATTCACT AACATCTTAG TCATTCCGAC
GAAAAGACCA CAGATCATTA AGTCCAACTG TCAGCCCCAT CCCCACCGCG      2700
CTTTTCTGGT GTCTAGTAAT TCAGGTTGAC AGTCGGGGTA GGGGTGGCGC
```

-continued

```
CCCACTGTCA CTCAGTGCCA CATCCACGCA TTTCTTGAAC ATCTCCAGGG      2750

GGGTGACAGT GAGTCACGGT GTAGGTGCGT AAAGAACTTG TAGAGGTCCC

ACAGTGACTC CACCCGTCAC CAGCTGTGCT TCAGAGCAGG CAGGGTGACA      2800

TGTCACTGAG GTGGGCAGTG GTCGACACGA AGTCTCGTCC GTCCCACTGT

GTCTCAGTGC CAGTTGCATC CTGCTGAAGA GCTTAACAGT GCAGTTTAAC      2850

CAGAGTCACG GTCAACGTAG GACGACTTCT CGAATTGTCA CGTCAAATTG

AACGGACTGA TTTGTTGATG TGGTTGCTGA ATCAGTACGT TGAGATGTCA      2900

TTGCCTGACT AAACAACTAC ACCAACGACT TAGTCATGCA ACTCTACAGT

CTAAACTTTT TGGAGATTAA TTTCAGGATG GAACACATTC TTAACCCTGA      2950

GATTTGAAAA ACCTCTAATT AAAGTCCTAC CTTGTGTAAG AATTGGGACT

AACCAGCCTT TGATTTGGGC TTGGCATTTG CAGAATTTGC AGGAAAAGAT      3000

TTGGTCGGAA ACTAAACCCG AACCGTAAAC GTCTTAAACG TCCTTTTCTA

TGTTTGGGAA CAGATGAATG GAATTTCCAC CAAACAGAAA ATTAACACTT      3050

ACAAACCCTT GTCTACTTAC CTTAAAGGTG GTTTGTCTTT TAATTGTGAA

ACACCAGTTT GAGTCTGGTC TTCGTTGGAT ATTTCTTAAG AATCTCATCA      3100

TGTGGTCAAA CTCAGACCAG AAGCAACCTA TAAAGAATTC TTAGAGTAGT

TCCTCCCTGC TCTTGGACCA GTGCTGCTGA CAGGAGGTGG AGGATCATCA      3150

AGGAGGGACG AGAACCTGGT CACGACGACT GTCCTCCACC TCCTAGTAGT

GGGTCAGCAT CCTCAGCATC TAGGGATGTG CACTATGTGT GATGGTGACA      3200

CCCAGTCGTA GGAGTCGTAG ATCCCTACAC GTGATACACA CTACCACTGT

CTTTAGAGAA CTGCTTTGAT TCCCCAGGGC TTTCCCTCTC TTCCATGCAG      3250

GAAATCTCTT GACGAAACTA AGGGGTCCCG AAAGGGAGAG AAGGTACGTC

GGCTCACTAT CAGCCCTGAA AGTCCAACTT TCTGAACTTC CAGCACCGTC      3300

CCGAGTGATA GTCGGGACTT TCAGGTTGAA AGACTTGAAG GTCGTGGCAG

TGCTCCTGGT AGGCTGTTCC ATAGAGGCCA CAGGGACTGT AGCCAGGCAT      3350

ACGAGGACCA TCCGACAAGG TATCTCCGGT GTCCCTGACA TCGGTCCGTA

GACCTTTTCC CAGCCGTGCT CTGAATCCAG CACTGGTGGC TGGGAGGCAG      3400

CTGGAAAAGG GTCGGCACGA GACTTAGGTC GTGACCACCG ACCCTCCGTC

CTCTGGTCCT GGGGTGCTGC AGTGAGCCAG GGAACAAGCT TATCGATACC      3450

GAGACCAGGA CCCCACGACG TCACTCGGTC CCTTGTTCGA ATAGCTATGG

GTCGACCTCG AGGGGGGGCC CGGTACCCAG CTTTTGTTCC CTTTAGTGAG      3500

CAGCTGGAGC TCCCCCCCGG GCCATGGGTC GAAAACAAGG GAAATCACTC

GGTTAATTTC GAGCTTGGCG TAATCATGGT CATAGCTGTT TCCTGTGTGA      3550

CCAATTAAAG CTCGAACCGC ATTAGTACCA GTATCGACAA AGGACACACT

AATTGTTATC CGCTCACAAT TCCACACAAC ATACGAGCCG GAAGCATAAA      3600

TTAACAATAG GCGAGTGTTA AGGTGTGTTG TATGCTCGGC CTTCGTATTT

GTGTAAAGCC TGGGGTGCCT AATGAGTGAG CTAACTCACA TTAATTGCGT      3650

CACATTTCGG ACCCCACGGA TTACTCACTC GATTGAGTGT AATTAACGCA

TGCGCTCACT GCCCGCTTTC CAGTCGGGAA ACCTGTCGTG CCAGCTGCAT      3700

ACGCGAGTGA CGGGCGAAAG GTCAGCCCTT TGGACAGCAC GGTCGACGTA
```

```
TAATGAATCG GCCAACGCGC GGGGAGAGGC GGTTTGCGTA TTGGGCGCTC        3750

ATTACTTAGC CGGTTGCGCG CCCCTCTCCG CCAAACGCAT AACCCGCGAG

TTCCGCTTCC TCGCTCACTG ACTCGCTGCG CTCGGTCGTT CGGCTGCGGC        3800

AAGGCGAAGG AGCGAGTGAC TGAGCGACGC GAGCCAGCAA GCCGACGCCG

GAGCGGTATC AGCTCACTCA AAGGCGGTAA TACGGTTATC CACAGAATCA        3850

CTCGCCATAG TCGAGTGAGT TTCCGCCATT ATGCCAATAG GTGTCTTAGT

GGGGATAACG CAGGAAAGAA CATGTGAGCA AAAGGCCAGC AAAAGGCCAG        3900

CCCCTATTGC GTCCTTTCTT GTACACTCGT TTTCCGGTCG TTTTCCGGTC

GAACCGTAAA AAGGCCGCGT TGCTGGCGTT TTTCCATAGG CTCCGCCCCC        3950

CTTGGCATTT TTCCGGCGCA ACGACCGCAA AAAGGTATCC GAGGCGGGGG

CTGACGAGCA TCACAAAAAT CGACGCTCAA GTCAGAGGTG GCGAAACCCG        4000

GACTGCTCGT AGTGTTTTTA GCTGCGAGTT CAGTCTCCAC CGCTTTGGGC

ACAGGACTAT AAAGATACCA GGCGTTTCCC CCTGGAAGCT CCCTCGTGCG        4050

TGTCCTGATA TTTCTATGGT CCGCAAAGGG GGACCTTCGA GGGAGCACGC

CTCTCCTGTT CCGACCCTGC CGCTTACCGG ATACCTGTCC GCCTTTCTCC        4100

GAGAGGACAA GGCTGGGACG GCGAATGGCC TATGGACAGG CGGAAAGAGG

CTTCGGGAAG CGTGGCGCTT TCTCATAGCT CACGCTGTAG GTATCTCAGT        4150

GAAGCCCTTC GCACCGCGAA AGAGTATCGA GTGCGACATC CATAGAGTCA

TCGGTGTAGG TCGTTCGCTC CAAGCTGGGC TGTGTGCACG AACCCCCCGT        4200

AGCCACATCC AGCAAGCGAG GTTCGACCCG ACACACGTGC TTGGGGGGCA

TCAGCCCGAC CGCTGCGCCT TATCCGGTAA CTATCGTCTT GAGTCCAACC        4250

AGTCGGGCTG GCGACGCGGA ATAGGCCATT GATAGCAGAA CTCAGGTTGG

CGGTAAGACA CGACTTATCG CCACTGGCAG CAGCCACTGG TAACAGGATT        4300

GCCATTCTGT GCTGAATAGC GGTGACCGTC GTCGGTGACC ATTGTCCTAA

AGCAGAGCGA GGTATGTAGG CGGTGCTACA GAGTTCTTGA AGTGGTGGCC        4350

TCGTCTCGCT CCATACATCC GCCACGATGT CTCAAGAACT TCACCACCGG

TAACTACGGC TACACTAGAA GGACAGTATT TGGTATCTGC GCTCTGCTGA        4400

ATTGATGCCG ATGTGATCTT CCTGTCATAA ACCATAGACG CGAGACGACT

AGCCAGTTAC CTTCGGAAAA AGAGTTGGTA GCTCTTGATC CGGCAAACAA        4450

TCGGTCAATG GAAGCCTTTT TCTCAACCAT CGAGAACTAG GCCGTTTGTT

ACCACCGCTG GTAGCGGTGG TTTTTTTGTT TGCAAGCAGC AGATTACGCG        4500

TGGTGGCGAC CATCGCCACC AAAAAAACAA ACGTTCGTCG TCTAATGCGC

CAGAAAAAAA GGATCTCAAG AAGATCCTTT GATCTTTTCT ACGGGGTCTG        4550

GTCTTTTTTT CCTAGAGTTC TTCTAGGAAA CTAGAAAAGA TGCCCCAGAC

ACGCTCAGAA GAACTCGTCA AGAAGGCGAT AGAAGGCGAT GCGCTGCGAA        4600

TGCGAGTCTT CTTGAGCAGT TCTTCCGCTA TCTTCCGCTA CGCGACGCTT

TCGGGAGCGG CGATACCGTA AGCACGAGG AAGCGGTCAG CCCATTCGCC        4650

AGCCCTCGCC GCTATGGCAT TCGTGCTCC TTCGCCAGTC GGGTAAGCGG

GCCAAGCTCT TCAGCAATAT CACGGGTAGC CAACGCTATG TCCTGATAGC        4700

CGGTTCGAGA AGTCGTTATA GTGCCCATCG GTTGCGATAC AGGACTATCG
```

```
GGTCCGCCAC ACCCAGCCGG CCACAGTCGA TGAATCCAGA AAAGCGGCCA        4750

CCAGGCGGTG TGGGTCGGCC GGTGTCAGCT ACTTAGGTCT TTTCGCCGGT

TTTTCCACCA TGATATTCGG CAAGCAGGCA TCGCCATGGG TCACGACGAG        4800

AAAAGGTGGT ACTATAAGCC GTTCGTCCGT AGCGGTACCC AGTGCTGCTC

ATCCTCGCCG TCGGGCATGC GCGCCTTGAG CCTGGCGAAC AGTTCGGCTG        4850

TAGGAGCGGC AGCCCGTACG CGCGGAACTC GGACCGCTTG TCAAGCCGAC

GCGCGAGCCC CTGATGCTCT TCGTCCAGAT CATCCTGATC GACAAGACCG        4900

CGCGCTCGGG GACTACGAGA AGCAGGTCTA GTAGGACTAG CTGTTCTGGC

GCTTCCATCC GAGTACGTGC TCGCTCGATG CGATGTTTCG CTTGGTGGTC        4950

CGAAGGTAGG CTCATGCACG AGCGAGCTAC GCTACAAAGC GAACCACCAG

GAATGGGCAG GTAGCCGGAT CAAGCGTATG CAGCCGCCGC ATTGCATCAG        5000

CTTACCCGTC CATCGGCCTA GTTCGCATAC GTCGGCGGCG TAACGTAGTC

CCATGATGGA TACTTTCTCG GCAGGAGCAA GGTGAGATGA CAGGAGATCC        5050

GGTACTACCT ATGAAAGAGC CGTCCTCGTT CCACTCTACT GTCCTCTAGG

TGCCCCGGCA CTTCGCCCAA TAGCAGCCAG TCCCTTCCCG CTTCAGTGAC        5100

ACGGGGCCGT GAAGCGGGTT ATCGTCGGTC AGGGAAGGGC GAAGTCACTG

AACGTCGAGC ACAGCTGCGC AAGGAACGCC CGTCGTGGCC AGCCACGATA        5150

TTGCAGCTCG TGTCGACGCG TTCCTTGCGG GCAGCACCGG TCGGTGCTAT

GCCGCGCTGC CTCGTCCTGC AGTTCATTCA GGGCACCGGA CAGGTCGGTC        5200

CGGCGCGACG GAGCAGGACG TCAAGTAAGT CCCGTGGCCT GTCCAGCCAG

TTGACAAAAA GAACCGGGCG CCCCTGCGCT GACAGCCGGA ACACGGCGGC        5250

AACTGTTTTT CTTGGCCCGC GGGGACGCGA CTGTCGGCCT TGTGCCGCCG

ATCAGAGCAG CCGATTGTCT GTTGTGCCCA GTCATAGCCG AATAGCCTCT        5300

TAGTCTCGTC GGCTAACAGA CAACACGGGT CAGTATCGGC TTATCGGAGA

CCACCCAAGC GGCCGGAGAA CCTGCGTGCA ATCCATCTTG TTCAATCATG        5350

GGTGGGTTCG CCGGCCTCTT GGACGCACGT TAGGTAGAAC AAGTTAGTAC

CGAAACGATC CTCATCCTGT CTCTTGATCA GATCTTGATC CCCTGCGCCA        5400

GCTTTGCTAG GAGTAGGACA GAGAACTAGT CTAGAACTAG GGACGCGGT

TCAGATCCTT GGCGGCAAGA AAGCCATCCA GTTTACTTTG CAGGGCTTCC        5450

AGTCTAGGAA CCGCCGTTCT TTCGGTAGGT CAAATGAAAC GTCCCGAAGG

CAACCTTACC AGAGGGCGCC CCAGCTGGCA ATTCCGGTTC GCTTGCTGTC        5500

GTTGGAATGG TCTCCCGCGG GGTCGACCGT TAAGGCCAAG CGAACGACAG

CATAAAACCG CCCAGTCTAG CAACTGTTGG GAAGGGCGAT CGGTGCGGGC        5550

GTATTTTGGC GGGTCAGATC GTTGACAACC CTTCCCGCTA GCCACGCCCG

CTCTTCGCTA TTACGCCAGC TGGCGAAAGG GGGATGTGCT GCAAGGCGAT        5600

GAGAAGCGAT AATGCGGTCG ACCGCTTTCC CCCTACACGA CGTTCCGCTA

TAAGTTGGGT AACGCCAGGG TTTTCCCAGT CACGACGTTG TAAAACGACG        5650

ATTCAACCCA TTGCGGTCCC AAAAGGGTCA GTGCTGCAAC ATTTTGCTGC
```

```
GCCAGTGAAT TGTAATACGA CTCACTATAG GGCGAATTGG AGCTCCACCG         5700

CGGTCACTTA ACATTATGCT GAGTGATATC CCGCTTAACC TCGAGGTGGC

CGGTGGC                                                        5707

GCCACCG
```

We claim:

1. A vector for expression of a nucleic acid sequence in tissue, comprising:
   - a nucleic acid cassette encoding insulin-like growth factor I;
   - a 5' flanking region including necessary sequences for expression of said nucleic acid cassette, wherein said 5' flanking region is 5' to said nucleic acid cassette;
   - a linker connecting said 5' flanking region to a nucleic acid, said linker has said nucleic acid cassette inserted thereon; and
   - a 3' flanking region, including a 3' untranslated region, or a 3' non-coding region, or both a 3' untranslated region and a 3' non-coding region which stabilizes mRNA expressed from said nucleic acid cassette, wherein said 3' flanking region is 3' to said said nucleic acid cassette;
   wherein said vector is a plasmid designated as pIG0100A or pIG0335.

2. A cell transformed with the vector of claim 1.

3. The transformed cell of claim 2, wherein said cell is myogenic.

* * * * *